(12) United States Patent
Schinazi et al.

(10) Patent No.: US 11,969,427 B2
(45) Date of Patent: Apr. 30, 2024

(54) USE OF TREM-1 INHIBITORS FOR TREATMENT, ELIMINATION AND ERADICATION OF HIV-1 INFECTION

(71) Applicants: EMORY UNIVERSITY, Atlanta, GA (US); CHILDREN'S HEALTHCARE OF ATLANTA, INC., Atlanta, GA (US)

(72) Inventors: Raymond F Schinazi, Miami, FL (US); Christina Gavegnano, Decatur, GA (US)

(73) Assignee: Emory University, Atlanta, GA (US)

( * ) Notice: Subject to any disclaimer, the term of this patent is extended or adjusted under 35 U.S.C. 154(b) by 117 days.

(21) Appl. No.: 17/329,893

(22) Filed: May 25, 2021

(65) Prior Publication Data

US 2022/0040185 A1 Feb. 10, 2022
US 2022/0313696 A9 Oct. 6, 2022

Related U.S. Application Data

(63) Continuation of application No. 16/788,374, filed on Feb. 12, 2020, now Pat. No. 11,052,090, which is a continuation of application No. 15/741,665, filed as application No. PCT/US2016/040694 on Jul. 1, 2016, now Pat. No. 10,765,679.

(60) Provisional application No. 62/188,624, filed on Jul. 4, 2015.

(51) Int. Cl.
| | | |
|---|---|---|
| A61K 38/00 | (2006.01) | |
| A61K 31/519 | (2006.01) | |
| A61K 38/08 | (2019.01) | |
| A61K 38/10 | (2006.01) | |
| A61K 38/17 | (2006.01) | |
| A61K 45/06 | (2006.01) | |
| A61P 31/14 | (2006.01) | |
| A61P 31/18 | (2006.01) | |
| C07K 16/28 | (2006.01) | |

(52) U.S. Cl.
CPC ............ *A61K 31/519* (2013.01); *A61K 38/08* (2013.01); *A61K 38/10* (2013.01); *A61K 38/17* (2013.01); *A61K 38/1709* (2013.01); *A61K 45/06* (2013.01); *A61P 31/14* (2018.01); *A61P 31/18* (2018.01); *C12N 2740/16034* (2013.01); *Y02A 50/30* (2018.01)

(58) Field of Classification Search
CPC ..... A61K 2300/00; A61K 38/17; A61P 31/18; A61P 31/14; C12N 2740/16034
See application file for complete search history.

*Primary Examiner* — Barry A Chestnut
(74) *Attorney, Agent, or Firm* — David S. Bradin; Maynard Nexsen PC

(57) ABSTRACT

Compounds, compositions, and methods of treatment and prevention of HIV, including HIV-1 and HIV-2, Dengue, and Chikungunya infection are disclosed. The compounds are TREM-1 inhibitors. Combinations of these TREM-1 inhibitors and additional antiretroviral compounds, such as NRTI, NNRTI, integrase inhibitors, entry inhibitors, protease inhibitors, JAK inhibitors, macrophage depleting agents, and the like, are also disclosed. In one embodiment, the combinations include a combination of adenine, cytosine, thymidine, and guanine nucleoside antiviral agents, optionally in further combination with at least one additional antiviral agent that works via a different mechanism than a nucleoside analog. This combination has the potential to eliminate the presence of HIV, Dengue, or Chikungunya virus in an infected patient.

16 Claims, 9 Drawing Sheets

Specification includes a Sequence Listing.

Figure 1. Extracellular TNF-α production is significantly increased in HIV-infected primary human macrophages.

Figure 2: Anti-HIV-1/2 potency and toxicity of Jakafi and tofacitinib in primary human PBM cells and macrophages.

| Compound | Anti-HIV-1 EC$_{50}$ in acutely infected human PBM cells (µM) | Anti-HIV-1 EC$_{90}$ in acutely infected human PBM cells (µM) | Anti-HIV-2 EC$_{50}$ in acutely infected human PBM cells (µM) | Anti-HIV-2 EC$_{90}$ in acutely infected human PBM cells (µM) | Anti-HIV-1 EC$_{50}$ in acutely infected human Mφ (µM) |
|---|---|---|---|---|---|
| Ruxolitinib (Jakafi) 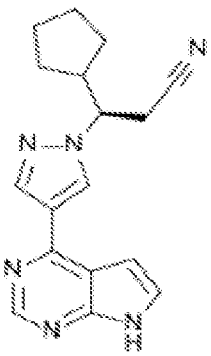 | 0.1 ± 0.02 (> 100) | 4.7 ± 0.07 (11) | 0.02 ± 0.01 (> 100) | 0.4 ± 0.2 (> 100) | 0.3 ± 0.1 (> 100) |
| Tofacitinib 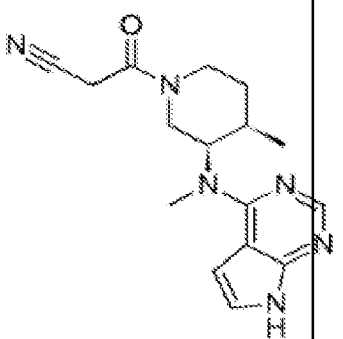 | 0.8 ± 0.3 (62) | 17.1 ± 15.1 (3) | 0.07 ± 0.006 (> 100) | 1.8 ± 1.1 (28) | 0.2 ± 0.08 (> 100) |
| AZT 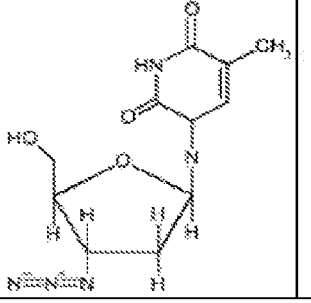 | 0.02 ± 0.008 (> 100) | 0.13 ± 0.03 (> 100) | 0.001 ± 0.0008 (> 100) | 0.01 ± 0.01 (> 100) | 0.01 ± 0.02 (> 100) |

Figure 2 cont'd.

| Compound | Anti-HIV-1 EC$_{90}$ in acutely infected human Mφ (μM) | IC$_{50}$ in PHA+IL-2 stimulated human PBM cells (μM) | IC$_{50}$ in PHA stimulated human PBM cells (μM) | IC$_{50}$ in human Mφ (μM) |
|---|---|---|---|---|
| Ruxolitinib (Jakafi) | 3.1 ± 1.8 (48) | > 50 | > 50 | > 100 |
| Tofacitinib | 2.9 ± 1.4 (17) | > 50 | > 50 | 49.2 |
| AZT | 0.07 ± 0.12 (> 100) | > 50 | > 50 | > 100 |

\* Indicates significant difference versus BaL-infected cells for respective marker, One-Way ANOVA
\*\* Indicates significant difference versus uninfected cells for respective marker, One-Way ANOVA

SEQUENCE LISTING

<160> NUMBER OF SEQ ID NOS: 13

<210> SEQ ID NO 1
<211> LENGTH: 12

```
<212> TYPE: PRT
<213> ORGANISM: Homo sapiens

<400> SEQUENCE: 1

Ser Ala Val Asp Arg Arg Ala Pro Ala Gly Arg Arg
1               5                   10

<210> SEQ ID NO 2
<211> LENGTH: 14
<212> TYPE: PRT
<213> ORGANISM: Homo sapiens

<400> SEQUENCE: 2

Cys Met Val Asp Gly Ala Arg Gly Pro Gln Ile Leu His Arg
1               5                   10

<210> SEQ ID NO 3
<211> LENGTH: 17
<212> TYPE: PRT
<213> ORGANISM: Homo sapiens

<400> SEQUENCE: 3

Leu Gln Glu Glu Asp Ala Gly Glu Tyr Gly Cys Met Val Asp Gly Ala
1               5                   10                  15

Arg

<210> SEQ ID NO 4
<211> LENGTH: 6
<212> TYPE: PRT
<213> ORGANISM: Homo sapiens

<400> SEQUENCE: 4

Leu Gln Glu Glu Asp Ala
1               5

<210> SEQ ID NO 5
<211> LENGTH: 6
<212> TYPE: PRT
<213> ORGANISM: Homo sapiens

<400> SEQUENCE: 5

Glu Asp Ala Gly Glu Tyr
1               5

<210> SEQ ID NO 6
<211> LENGTH: 6
<212> TYPE: PRT
<213> ORGANISM: Homo sapiens

<400> SEQUENCE: 6

Gly Glu Tyr Gly Cys Met
1               5

<210> SEQ ID NO 7
<211> LENGTH: 12
<212> TYPE: PRT
<213> ORGANISM: Homo sapiens

<400> SEQUENCE: 7

Leu Gln Glu Glu Asp Ala Gly Glu Tyr Gly Cys Met
1               5                   10

<210> SEQ ID NO 8
<211> LENGTH: 17
```

```
<212> TYPE: DNA
<213> ORGANISM: Homo sapiens

<400> SEQUENCE: 8
tgcccgccat catccta                                                17

<210> SEQ ID NO 9
<211> LENGTH: 21
<212> TYPE: DNA
<213> ORGANISM: Homo sapiens

<400> SEQUENCE: 9
tcctcatcgc cctcccatcc c                                           21

<210> SEQ ID NO 10
<211> LENGTH: 23
<212> TYPE: DNA
<213> ORGANISM: Homo sapiens

<400> SEQUENCE: 10
cgtctgttat gtaaaggatg cgt                                         23

<210> SEQ ID NO 11
<211> LENGTH: 17
<212> TYPE: DNA
<213> ORGANISM: Homo sapiens

<400> SEQUENCE: 11
gcgcggctac agcttca                                                17

<210> SEQ ID NO 12
<211> LENGTH: 18
<212> TYPE: DNA
<213> ORGANISM: Homo sapiens

<400> SEQUENCE: 12
caccacggcc gagcggga                                               18

<210> SEQ ID NO 13
<211> LENGTH: 22
<212> TYPE: DNA
<213> ORGANISM: Homo sapiens

<400> SEQUENCE: 13
tctccttaat gtcacgcacg at                                          22
```

USE OF TREM-1 INHIBITORS FOR TREATMENT, ELIMINATION AND ERADICATION OF HIV-1 INFECTION

CROSS REFERENCE TO RELATED APPLICATIONS

This application is a continuation application of U.S. Utility application Ser. No. 16/788,374, filed on Feb. 12, 2020, which is a continuation of U.S. Utility application Ser. No. 15/741,665, filed Jan. 3, 2018, which claims priority under 35 U.S.C. § 371 to PCT/US2016/040694, filed on Jul. 1, 2016, which in turn claims priority to U.S. Provisional Application Ser. No. 61/188,624, filed Jul. 4, 2015. The contents of each of these application is incorporated by reference in their entirety for all purposes.

BACKGROUND OF THE INVENTION

In 1983, the etiological cause of AIDS was determined to be the human immunodeficiency virus (HIV-1). In 1985, it was reported that the synthetic nucleoside 3'-azido-3'-deoxythymidine (AZT) inhibited the replication of human immunodeficiency virus. Since then, a number of other synthetic nucleosides, including 2',3'-dideoxyinosine (DDI), 2',3'-dideoxycytidine (DDC), 3'-deoxy-2',3'-didehydrothymidine (D4T), ((1S,4R)-4-[2-amino-6-(cyclopropylamino)-9H-purin-9-yl]-2-cyclopentene-1-methanol sulfate (ABC), cis-2-hydroxymethyl-5-(5-fluorocytosin-1-yl)-1,3-oxathiolane ((−)-FTC), and (−)-cis-2-hydroxymethyl-5-(cytosin-1-yl)-1,3-oxathiolane (3TC), have been proven to be effective against HIV-1. After cellular phosphorylation to the 5'-triphosphate by cellular kinases, these synthetic nucleosides are incorporated into a growing strand of viral DNA, causing chain termination due to the absence of the 3'-hydroxyl group. They can also inhibit the viral enzyme reverse transcriptase.

Drug-resistant variants of HIV-1 can emerge after prolonged treatment with an antiviral agent. Drug resistance most typically occurs by mutation of a gene that encodes for an enzyme used in viral replication, and most typically in the case of HIV-1, reverse transcriptase, protease, or DNA polymerase. Recently, it has been demonstrated that the efficacy of a drug against HIV-1 infection can be prolonged, augmented, or restored by administering the compound in combination or alternation with a second, and perhaps third, antiviral compound that induces a different mutation from that caused by the principle drug. Alternatively, the pharmacokinetics, biodistribution, or other parameter of the drug can be altered by such combination or alternation therapy. In general, combination therapy is typically preferred over alternation therapy because it induces multiple simultaneous pressures on the virus. However, drug resistance can still emerge, and no effective cure has yet been identified, such that a patient can ultimately stop treatment.

Treatment for AIDS using attachment and fusion inhibitors as well as other antiviral drugs has been somewhat effective. Current clinical treatments for HIV-1 infections include triple drug combinations called Highly Active Antiretroviral Therapy ("HAART"). HAART typically involves various combinations of nucleoside reverse transcriptase inhibitors, non-nucleoside reverse transcriptase inhibitors, and HIV-1 protease inhibitors. In compliant patients, HAART is effective in reducing mortality and progression of HIV-1 infection to AIDS. However, these multidrug therapies do not eliminate HIV-1 and long-term treatment often results in multidrug resistance. Also, many of these drugs are highly toxic and/or require complicated dosing schedules that reduce compliance and limit efficacy. There is, therefore, a continuing need for the development of additional drugs for the prevention and treatment of HIV-1 infection and AIDS.

It would be useful to have combination therapy that minimizes the virological failure of patients taking conventional antiretroviral therapy. It would also be useful to provide a therapy that can provide a cure for HIV/AIDS, by destroying the virus altogether in all its reservoirs.

It would also be useful to have a combination therapy that can inhibit the detrimental hyper-inflammatory events caused by HIV-1 that are not currently addressed by existing antiviral agents.

It would further be useful clinically to have a combination therapy that can selectively and potently inhibit pro-inflammatory events in monocytes/macrophages, a primary HIV-1 target cell and viral reservoir, which is currently unmet by existing antivirals.

It would also be useful to have a combination therapy that can selectively inhibit HIV-1 infection, activation, and cell death in HIV-target cells in the brain/central nervous system (CNS) as well as other viral reservoirs, which is a currently unmet need with existing antiretroviral agents.

The present invention provides such therapy, as well as methods of treatment using the therapy.

SUMMARY OF THE INVENTION

Antiretroviral TREM-1 inhibitors, compositions including such inhibitors, and methods for their use in treating HIV-1 and HIV-2 infections, as well as other viruses that rely on cellular activation to replicate in host cells, such as Dengue, Influenza, West Nile, and Chikingunya virus infections, are provided.

The TREM-1 inhibitors can be administered in combination therapy, for example, using JAK inhibitors, HAART, macrophage depletion agents including but not limited to those of bisphosphonate classes, such as alendronate, Ibandronate, and clodronate, and other immunomodulator based agents such as dasatinib or imatinib, or PI3K/Akt inhibitors.

It is believed that this therapy, particularly when administered at an early stage in the development of HIV-1 infection, has the possibility of eliminating HIV-1 infection in a person. While not wishing to be bound to a particular theory, it is believed that the TREM-1 inhibitors function in a way that is not likely to provoke resistance (i.e., does not involve the selective pressure that traditionally confers resistance, including direct inhibition of viral enzymes, or introduction of modified bases in a way that would provoke enzymatic or viral mutations, as a direct function of alteration/inhibition of the viral replication cycle). Instead, TREM-1 inhibitors can confer inhibition of pro-HIV events such as inhibition of IL-6, TNF-α, IL-1α/β, and monocyte and macrophage activation such as $CD14^+/CD16^+$ monocytes, and sCD163 production. Inhibition of these events results in inhibition of a pro-HIV environment, wherein the milieu of reduced monocyte/macrophage activation conferred by TREM-1 inhibitors results in a microenvironment that is not supportive of productive viral replication.

Further, due to this mechanism, which indirectly confers a microenvironment non-supportive of productive viral replication, when the TREM-1 inhibitors are combined with different nucleosides containing all the possible bases (ACTG), optionally in the presence of additional agents, the combination minimizes the ability of the virus to adapt its reverse transcriptase and develop resistance to any class of nucleoside antiviral nucleosides (i.e., adenine, cytosine, thymidine, or guanine), because it would be susceptible to at least one of the other nucleoside antiviral agents that are present, and/or the additional non-NRTI therapeutic agent. Furthermore, hitting the same target such as the active site of the HIV-1 polymerase with different bases allows complete and thorough chain termination of all the possible growing viral DNA chains. The use of an NNRTI in addition to the four different nucleosides (ACTG analogs) can be even more effective, since NNRTI bind to the HIV-polymerase and cause the enzyme to change conformation preventing chain elogation by natural nucleosides interacting in the active site of the enzyme.

In any of these embodiments, additional therapeutic agents can be used in combination with these agents, particularly including agents with a different mode of attack. Such agents include but are not limited to: antivirals, such as cytokines, e.g., rIFN alpha, rIFN beta, rIFN gamma; amphotericin B as a lipid-binding molecule with anti-HIV activity; a specific viral mutagenic agent (e.g., ribavirin), an HIV-1 VIF inhibitor, and an inhibitor of glycoprotein processing. Representative anti-TNF-α therapies include, but are not limited to, Infliximab (Remicade), adalimumab (Humira), certolizumab pegol (Cimzia), and golimumab (Simponi), alone or with a circulating receptor fusion protein such as etanercept (Enbrel).

When administered in combination, the agents can be administered in a single or in multiple dosage forms. In some embodiments, some of the antiviral agents are orally administered, whereas other antiviral agents are administered by injection, which can occur at around the same time, or at different times.

The compounds can be used in different ways to treat or prevent HIV, and, in one embodiment, to cure an HIV infection. The invention encompasses combinations of the two types of antiviral agents, or pharmaceutically acceptable derivatives thereof, that are synergistic, i.e., better than either agent or therapy alone.

In one embodiment, a combination of a TREM-1 inhibitor as described herein, a macrophage depleting agent (e.g., clodronate-loaded liposomes or bisphosphonate class agents loaded in either liposomes or various nanoparticle formulations, gadolinium chloride (GdCl)), plus HAART therapy is used.

In another embodiment, a combination of a histone deacetylase inhibitor (HDAC inhibitor) or interleukin 7 (IL-7) and HAART and a TREM-1 inhibitor is used.

In another embodiment, the TREM-1 inhibitors are administered to a patient before, during, or after administration of a vaccine or an immunomodulatory agent, such as Jak inhibitors, PI3K inhibitors, or dasatinib/imatinib.

Combinations of these approaches can also be used.

The antiviral combinations described herein provide means of treatment which can not only reduce the effective dose of the individual drugs required for antiviral activity, thereby reducing toxicity, but can also improve their absolute antiviral effect, as a result of attacking the virus through multiple mechanisms. That is, various combinations described herein are useful because their synergistic actions permit the use of less drug, and/or increase the efficacy of the drugs when used together in the same amount as when used alone.

The use of TREM-1 inhibitors, alone or in combination, provides a means for circumventing the development of viral resistance, thereby providing the clinician with a more efficacious treatment.

The disclosed TREM-1 inhibitors, used alone or in combination or in alternation therapies, are useful in the prevention and treatment of HIV-1 infections and other related conditions such as AIDS-related complex (ARC), persistent generalized lymphadenopathy (PGL), AIDS-related neurological conditions, anti-HIV antibody positive and HIV-positive conditions, Kaposi's sarcoma, thrombocytopenia purpurea and opportunistic infections. In addition, these compounds or formulations can be used prophylactically to prevent or retard the progression of clinical illness in individuals who are anti-HIV antibody or HIV-antigen positive or who have been exposed to HIV. The therapy can be also used to treat other viral infections, such as HIV-2, Dengue and Chikungunya virus.

HIV-2 presents with significant similarities to HIV-1 relative to immunomodulatory events that are key to productive viral replication. These events are similar within HIV-1 and HIV-2, wherein pro-inflammatory cytokines, upregulation of activation markers, trafficking across and within the blood-brain-barrier of infected cells, and systemic hyperactivation across and within various microenvironments exists for both viruses.

As discussed herein, TREM-1 inhibitors can be useful for both treatment, prophylaxis, and eradication of both HIV-1 and HIV-2. For Chikungunya virus, the pathology of this virus is hyper-inflammatory cytokines, including IL-6, TNF-α, CRP, IL-1α/β, and others. Chikungunya virus results in a severe rheumatoid arthritis pathology systemically, and it would be useful for a drug to inhibit these events specifically and potently, as do TREM-1 inhibitors. Monocytes/macrophages are a major target cell of Chikungunya virus, and TREM-1 inhibitors inhibit the above described pro-inflammatory cytokines produced by monocytes/macrophages specifically. Inhibition of these cytokines can treat Chikungunya virus infection. Inhibition of these cytokines can eradicate Chikungunya virus infection, or be used herein to provide prophylaxis for Chikungunya virus infection.

Dengue virus is known to infect megakaryocytes (as well as other cells such as hepatocytes) and any modulation in these cells to reduce inflammation could be beneficial.

BRIEF DESCRIPTION OF THE FIGURES

FIG. 2 is a chart showing the potency and toxicity of JAK inhibitors Tofacitinib or Jakafi versus FDA approved control AZT in acutely infected resting macrophages (MØ), as well as in peripheral blood mononuclear (PBM) cells. Median effective antiviral concentration ($EC_{50}$) data (potency) is shown in terms of μM concentration of the compounds. The $IC_{50}$ values (toxicity) (μM) are also shown in PBM, MØ cells, CEM cells, and Vero cells.

Figure 4A:
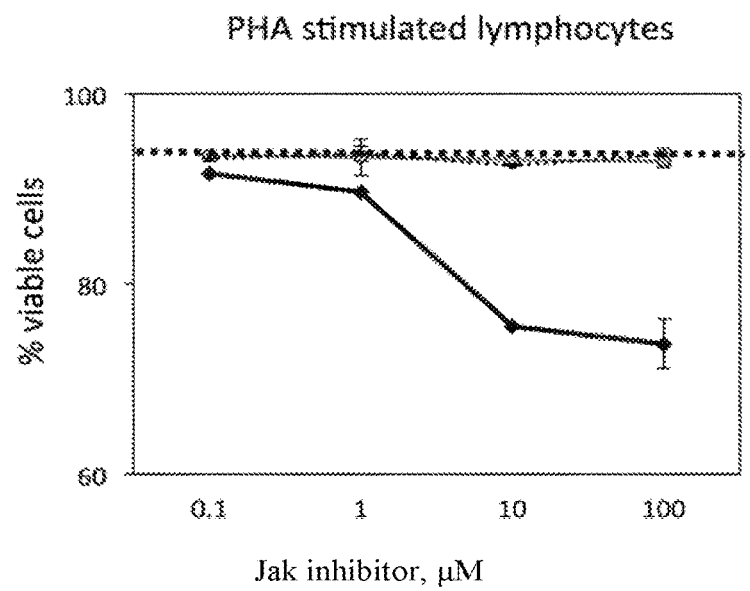
FIGS. 4A-D are charts showing the effect of Jak inhibitors on the proliferation and viability of PHA or PHA+IL-2 stimulated primary human, in terms of cell count×$10^{-6}$ vs. concentration of Jak inhibitor (μM). For PHA stimulated lymphocytes, viability and proliferation were not significantly different than that of cells exposed to media alone for all concentrations of either ruxolitinib or tofacitinib (FIG.
Figure 4B:
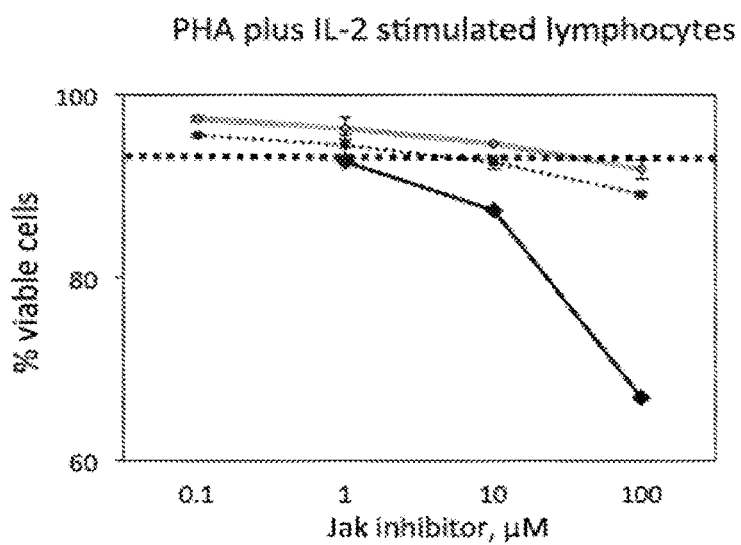
Figure 4C:
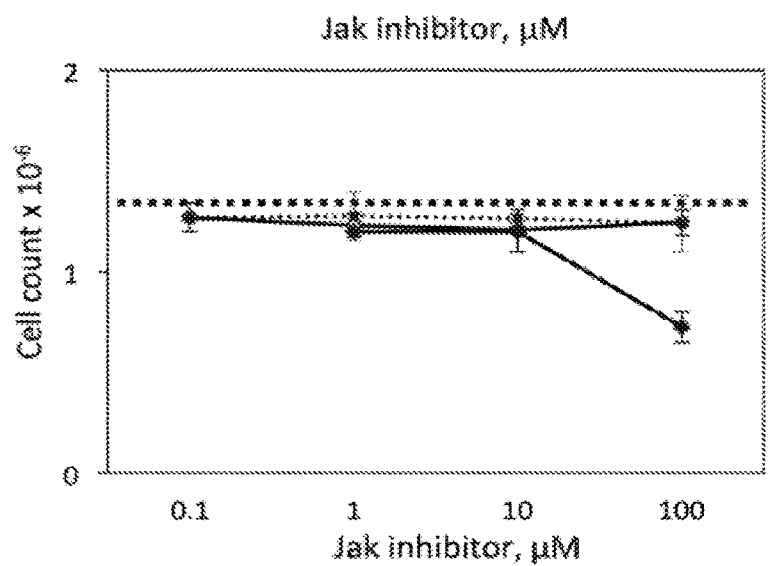
Figure 4D:
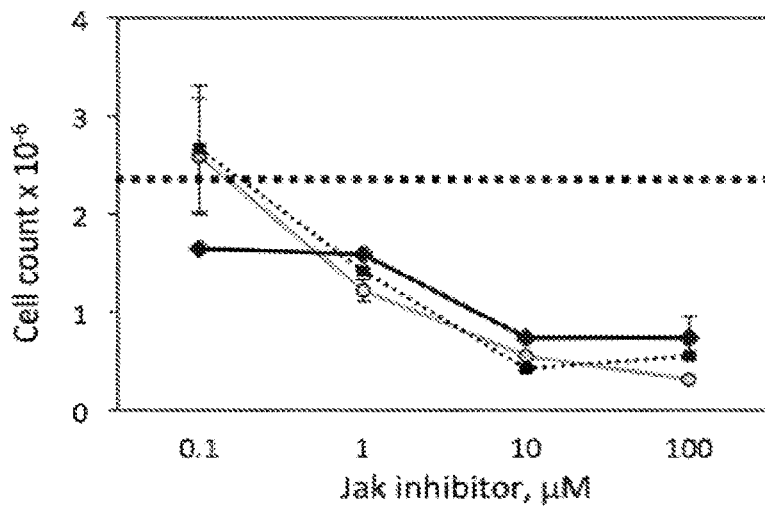

4A, FIG. 4C). For PHA+IL-2 stimulated lymphocytes, viability was not significantly different than that of cells exposed to media alone for all concentrations of either ruxolitinib (dotted line with squares) or tofacitinib (light gray line with diamonds) (FIG. 4B), however proliferation was significantly inhibited by 1 μM of ruxolitinib or tofacitinib (FIG. 4D).

Figure 5A:
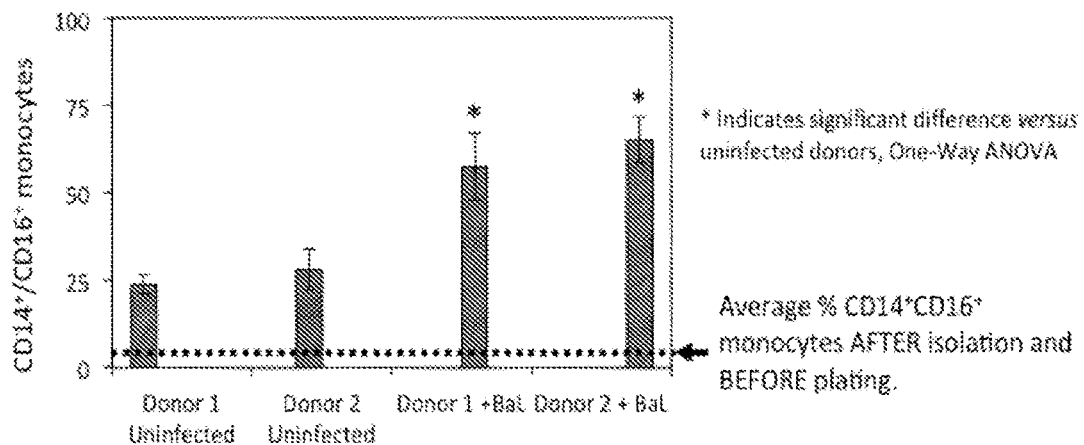
Figure 5B:
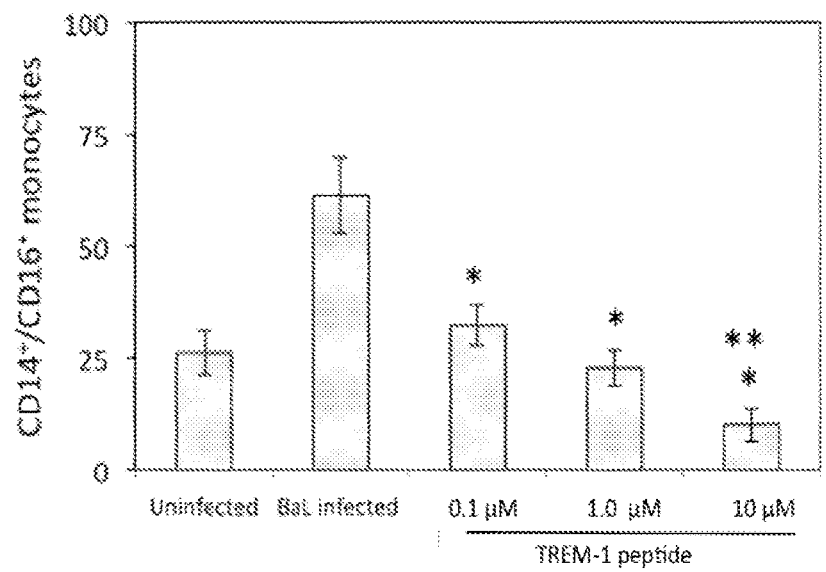
Figure 6A:
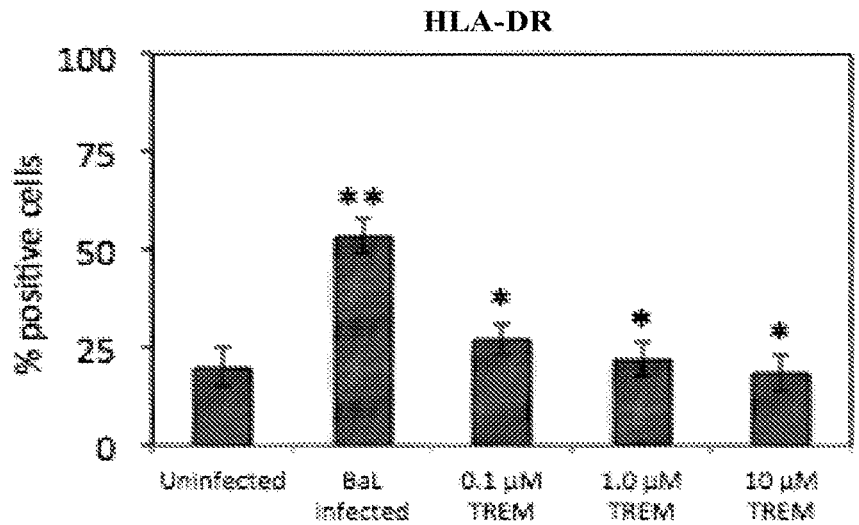
Figure 6B:
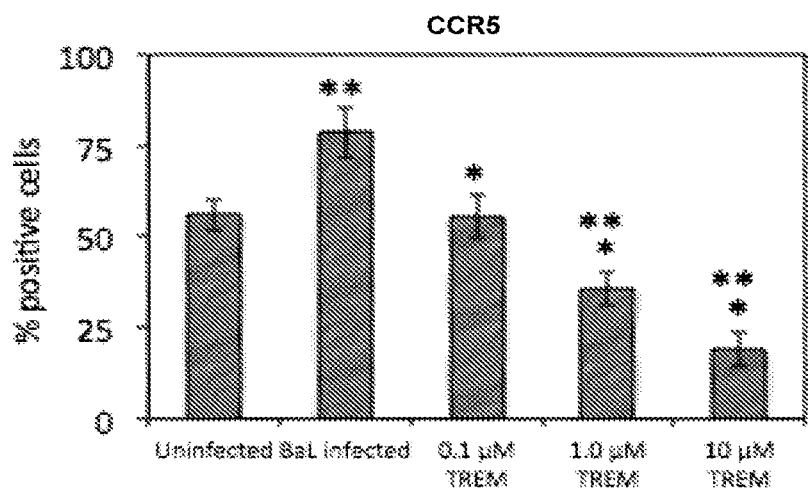
Figure 6C:
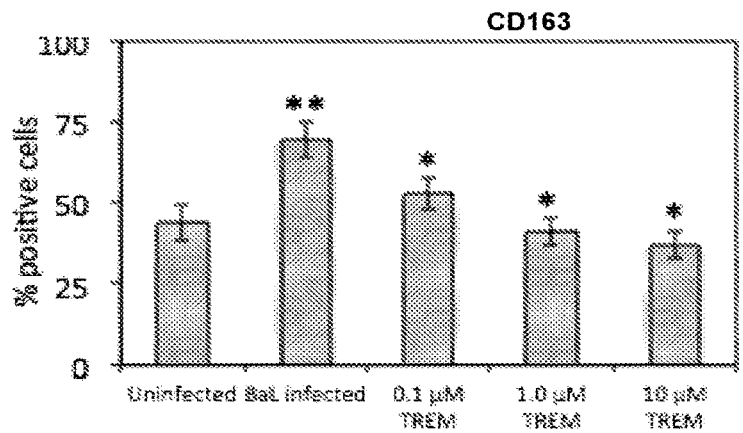
Figure 6D:
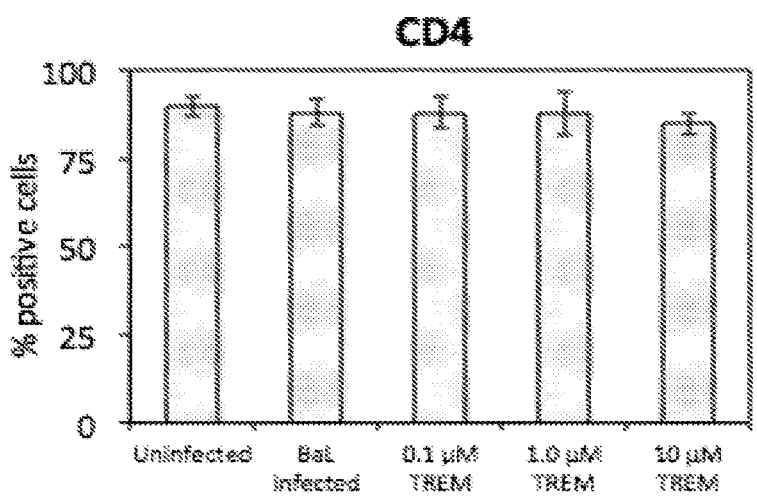

FIGS. 5A and 5B are charts showing the results of exposure of primary human monocytes to replication competent M-R5 HIV-1 BaL for 5 days prior to quantification of HIV-induced activation (CD14$^+$/CD16$^+$ monocytes; tandem two color FACS). FIG. 5A shows that HIV infection is associated with an increase in the number of activated monocytes. FIG. 5B shows that following administration of TREM-1 peptide, the number of activated monocytes was lower. The assay represents three independent donors conducted with duplicates. Data are mean and standard deviations, * indicates significant reduction versus BaL infected, no drug control (one-way ANOVA).

FIGS. 6A-6D are charts showing the percentage of positive cells (%) in the presence or absence of various concentrations of TREM-1 peptide (M). Following treatment of primary human macrophages with replication competent M-R5 HIV-1 BaL for 5 days, the TREM-1 peptide significantly reduced HIV-induced activation in primary human macrophages, as shown with HIV-1 induced activation markers HLA-DR (FIG. 6A), CCR5 (FIG. 6B), and CD163 (FIG. 6C); * one way ANOVA). TREM-1 peptide does not reduce CD4 expression (FIG. 6D), demonstrating that CD4 receptor expression-mediated innate and adaptive immunity is not altered. HIV-1 BaL significantly increases activation markers CD163, CCR5, and CD163 versus no virus control (**; one-way ANOVA). Data are mean and standard deviation for three independent donors conducted in duplicates.

DETAILED DESCRIPTION OF THE INVENTION

The present invention is directed to compounds, compositions and methods for treating viral infections, such as HIV infections, including HIV-1 and HIV-2 infections, as well as other viruses that rely on cellular activation to replicate in host cells, such as Dengue, Influenza, West Nile, and Chikingunya virus infections. In one embodiment, the compounds are TREM-1 inhibitors, which can be administered alone, or in combination or alternation with JAK inhibitors, such as heteroaryl substituted pyrrolo[2,3-b]pyridines and heteroaryl substituted pyrrolo[2,3-b]pyrimidines that modulate the activity of Janus kinases (JAK inhibitors), HAART therapy, or other anti-HIV therapies.

The various embodiments of the invention are described in more detail below, and will be better understood with reference to the following non-limiting definitions.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used herein, any "R" group(s) such as, without limitation, $R^1$, $R^{1a}$, $R^{1b}$, $R^c$, and Rid represent substituents that can be attached to the indicated atom. A non-limiting list of R groups include, but are not limited to, hydrogen, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxy, alkoxy, aryloxy, acyl, ester, mercapto, cyano, halogen, thiocarbonyl, O-carbamyl, N-carbamyl, O-thiocarbamyl, N-thiocarbamyl, C-amido, N-amido, S-sulfonamido, N-sulfonamide, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. An R group may be substituted or unsubstituted. If two "R" groups are covalently bonded to the same atom or to adjacent atoms, then they may be "taken together" as defined herein to form a cycloalkyl, cycloalkenyl, cycloalkynyl, aryl, heteroaryl or heteroalicyclyl group. For example, without limitation, if R' and R" of an NR'R" group are indicated to be "taken together", it means that they are covalently bonded to one another at their terminal atoms to form a ring that includes the nitrogen:

Whenever a group is described as being "optionally substituted" that group may be unsubstituted or substituted with one or more of the indicated substituents. Likewise, when a group is described as being "unsubstituted or substituted" if substituted, the substituent may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, ester, mercapto, alkylthio, arylthio, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. Each of these substituents can be further substituted.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

As used herein, the term "alkyl" can be straight or branched hydrocarbon chains that comprise a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group can also be a lower alkyl having 1 to 6 carbon atoms. The alkyl group of the compounds may be designated as "$C_1$-$C_6$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. By way of example only, "$C_1$-$C_6$ alkyl" indicates that there are one to six carbon atoms in the alkyl chain. Typical alkyl groups include, but are in no way limited to, methyl, ethyl, propyl, isopropyl, butyl, isobutyl, tertiary butyl, pentyl, hexyl, and the like. The alkyl group may be substituted or unsubstituted.

As used herein, "alkenyl" refers to an alkyl group that contains in the straight or branched hydrocarbon chain one or more double bonds. An alkenyl group may be unsubstituted or substituted.

As used herein, "alkynyl" refers to an alkyl group that contains in the straight or branched hydrocarbon chain one or more triple bonds. An alkynyl group may be unsubstituted or substituted.

As used herein, the term "alkoxy" includes O-alkyl groups wherein "alkyl" is defined above. As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, and the like.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "cycloalkynyl" refers to a mono- or multi-cyclic hydrocarbon ring system that contains one or more triple bonds in at least one ring. Pf there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group is a $C_{6-14}$ aryl group, a $C_{6-10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms, that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted.

As used herein, "heteroalicyclic" or "heteroalicyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatoms are independently selected from oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides, cyclic carbamates, and the like. When composed of two or more rings, the rings may be joined together in a fused fashion. Additionally, any nitrogens in a heteroalicyclic may be quaternized. Heteroalicyclyl or heteroalicyclic groups may be unsubstituted or substituted. Examples of such "heteroalicyclic" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, A-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, 3,4-methylenedioxyphenyl).

An "aralkyl" is an aryl group connected, as a substituent, via a lower alkylene group. The lower alkylene and aryl group of an aralkyl may be substituted or unsubstituted. Examples include but are not limited to benzyl, substituted benzyl, 2-phenylalkyl, 3-phenylalkyl, and naphtylalkyl.

A "heteroaralkyl" is heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, and imidazolylalkyl, and their substituted as well as benzo-fused analogs.

A "(heteroalicyclyl)alkyl" is a heterocyclic or a heteroalicyclylic group connected, as a substituent, via a lower alkylene group. The lower alkylene and heterocyclic or a heterocyclyl of a (heteroalicyclyl)alkyl may be substituted or unsubstituted. Examples include but are not limited tetrahydro-2H-pyran-4-yl)methyl, (piperidin-4-yl)ethyl, (piperidin-4-yl)propyl, (tetrahydro-2H-thiopyran-4-yl)methyl, and (1,3-thiazinan-4-yl)methyl.

"Lower alkylene groups" are straight-chained tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group may be substituted or unsubstituted.

As used herein, "alkoxy" refers to the formula —OR wherein R is an alkyl, alkenyl, alkynyl, cycloalkyl, cycloalkenyl, cycloalkynyl, aryl, heteroaryl, heteroalicyclyl, aralkyl, or (heteroalicyclyl)alkyl is defined as above. Examples of include methoxy, ethoxy, n-propoxy, 1-methylethoxy (isopropoxy), n-butoxy, iso-butoxy, sec-butoxy, tert-butoxy, phenoxy and the like. An alkoxy may be substituted or unsubstituted.

As used herein, "acyl" refers to a hydrogen, alkyl, alkenyl, alkynyl, or aryl connected, as substituents, via a carbonyl group. Examples include formyl, acetyl, propanoyl, benzoyl, and acryl. An acyl may be substituted or unsubstituted.

As used herein, "hydroxyalkyl" refers to an alkyl group in which one or more of the hydrogen atoms are replaced by hydroxy group. Examples of hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by halogen (e.g., mono-haloalkyl, di-haloalkyl and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

As used herein, "haloalkoxy" refers to an alkoxy group in which one or more of the hydrogen atoms are replaced by halogen (e.g., mono-haloalkoxy, di-haloalkoxy and tri-haloalkoxy). Such groups include but are not limited to, chloromethoxy, fluoromethoxy, difluoromethoxy, trifluoromethoxy and 1-chloro-2-fluoromethoxy, 2-fluoroisobutoxy. A haloalkoxy may be substituted or unsubstituted.

A "sulfenyl" group refers to an "—SR" group in which R is hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. A sulfenyl may be substituted or unsubstituted.

A "sulfinyl" group refers to an "—S(=O)—R" group in which R is the same as defined with respect to sulfenyl. A sulfinyl may be substituted or unsubstituted.

A "sulfonyl" group refers to an "$SO_2R$" group in which R is the same as defined with respect to sulfenyl. A sulfonyl may be substituted or unsubstituted.

An "O-carboxy" group refers to a "RC(=O)O—" group in which R is hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined herein. An O-carboxy may be substituted or unsubstituted.

The terms "ester" and "C-carboxy" refer to a "—C(=O)OR" group in which R is the same as defined with respect to O-carboxy. An ester and C-carboxy may be substituted or unsubstituted.

A "thiocarbonyl" group refers to a "—C(=S)R" group in which R is the same as defined with respect to O-carboxy. A thiocarbonyl may be substituted or unsubstituted.

A "trihalomethanesulfonyl" group refers to an "$X_3CSO_2$—" group wherein X is a halogen.

A "trihalomethanesulfonamido" group refers to an "$X_3CS(O)_2RN$—" group wherein X is a halogen and R defined with respect to O-carboxy.

The term "amino" as used herein refers to a —$NH_2$ group.

As used herein, the term "hydroxy" refers to a —OH group.

A "cyano" group refers to a "—CN" group.

The term "azido" as used herein refers to a —$N_3$ group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "carbonyl" group refers to a C=O group.

An "S-sulfonamido" group refers to a "—$SO_1NR_AR_B$" group in which $R_A$ and $R_B$ are the same as R defined with respect to O-carboxy. An S-sulfonamido may be substituted or unsubstituted.

An "N-sulfonamido" group refers to a "$R_BSO_2N(R_A)$—" group in which $R_A$ and $R_B$ are the same as R defined with respect to O-carboxy. A N-sulfonamido may be substituted or unsubstituted.

An "O-carbamyl" group refers to a "—OC(=O)$NR_AR_B$" group in which $R_A$ and $R_B$ are the same as R defined with respect to O-carboxy. An 0-carbamyl may be substituted or unsubstituted.

An "N-carbamyl" group refers to an "$R_BOC(=O)NR_A$—" group in which $R_A$ and $R_B$ are the same as R defined with respect to O-carboxy. An N-carbamyl may be substituted or unsubstituted.

An "O-thiocarbamyl" group refers to a "—OC(=S)—$NR_AR_B$" group in which $R_A$ and $R_B$ are the same as R defined with respect to O-carboxy. An 0-thiocarbamyl may be substituted or unsubstituted.

An "N-thiocarbamyl" group refers to an "$R_BOC(=S)NR_A$—" group in which $R_A$ and $R_B$ are the same as R defined with respect to O-carboxy. An N-thiocarbamyl may be substituted or unsubstituted.

A "C-amido" group refers to a "—C(=O)$NR_AR_B$" group in which $R_A$ and $R_B$ are the same as R defined with respect to O-carboxy. A C-amido can be substituted or unsubstituted.

An "N-amido" group refers to a "$R_BC(=O)NR_A$—" group in which $R_A$ and $R_B$ are the same as R defined with respect to O-carboxy. An N-amido can be substituted or unsubstituted.

As used herein, "organylcarbonyl" refers to a group of the formula —C(=O)R' wherein R' can be alkyl, alkenyl, alkynyl, cycloalkyl, cycloalkenyl, cycloalkynyl, aryl, heteroaryl, heteroalicyclyl, aralkyl, or (heteroalicyclyl)alkyl. An organylcarbonyl can be substituted or unsubstituted.

The term "alkoxycarbonyl" as used herein refers to a group of the formula —C(=O)OR', wherein R' is the same as defined with respect to organylcarbonyl. An alkoxycarbonyl can be substituted or unsubstituted.

As used herein, "organylaminocarbonyl" refers to a group of the formula C(=O)NR'R" wherein R' and R" are independently selected from the same substituents as defined with respect to organylcarbonyl. An organylaminocarbonyl can be substituted or unsubstituted.

As used herein, the term "levulinoyl" refers to a —C(=O)$CH_2CH_2$C(=O)$CH_3$ group.

The term "halogen atom," as used herein, means any one of the radio-stable atoms of column 7 of the Periodic Table of the Elements, i.e., fluorine, chlorine, bromine, or iodine, with fluorine and chlorine being preferred.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the term "nucleoside" refers to a compound composed of any pentose or modified pentose moiety attached to a specific portion of a heterocyclic base, tautomer, or derivative thereof such as the 9-position of a purine, 1-position of a pyrimidine, or an equivalent position of a heterocyclic base derivative. Examples include, but are not limited to, a ribonucleoside comprising a ribose moiety and a deoxyribonucleoside comprising a deoxyribose moiety, and in some instances, the nucleoside is a nucleoside drug analog. As used herein, the term "nucleoside drug analog" refers to a compound composed of a nucleoside that has therapeutic activity, such as antiviral, antineoplastic, anti-parasitic and/or antibacterial activity.

As used herein, the term "nucleotide" refers to a nucleoside having a phosphate ester substituted on the 5'-position or an equivalent position of a nucleoside derivative.

As used herein, the term "heterocyclic base" refers to a purine, a pyrimidine and derivatives thereof. The term "purine" refers to a substituted purine, its tautomers and analogs thereof. Similarly, the term "pyrimidine" refers to a substituted pyrimidine, its tautomers and analogs thereof. Examples of purines include, but are not limited to, purine, adenine, guanine, hypoxanthine, xanthine, theobromine, caffeine, uric acid and isoguanine. Examples of pyrimidines include, but are not limited to, cytosine, thymine, uracil, and derivatives thereof. An example of an analog of a purine is 1,2,4-triazole-3-carboxamide.

Other non-limiting examples of heterocyclic bases include diaminopurine, 8-oxo-$N^6$-methyladenine, 7-deazaxanthine, 7-deazaguanine, $N^4,N^4$-ethanocytosin, $N^6,N^6$-ethano-2,6-diaminopurine, 5-methylcytosine, 5-fluorouracil, 5-bromouracil, pseudoisocytosine, isocytosine, isoguanine, and other heterocyclic bases described in U.S. Pat. Nos. 5,432,272 and 7,125,855, which are incorporated herein by reference for the limited purpose of disclosing additional heterocyclic bases.

The term "—O-linked amino acid" refers to an amino acid that is attached to the indicated moiety via its main-chain carboxyl function group. When the amino acid is attached, the hydrogen that is part of the —OH portion of the carboxyl function group is not present and the amino acid is attached via the remaining oxygen. An —O-linked amino acid can be protected at any nitrogen group that is present on the amino acid. For example, an —O-linked amino acid can contain an amide or a carbamate group. Suitable amino acid protecting groups include, but are not limited to, carbobenzyloxy (Cbz), p-methoxybenzyl carbonyl (Moz or MeOZ), tert-butyloxycarbonyl (BOC), 9-fluorenylmethyloxycarbonyl (FMOC), benzyl (Bn), p-methoxybenzyl (PMB), 3,4-dimethoxybenzyl (DMPM), and tosyl (Ts) groups. The term "—N-linked amino acid" refers to an amino acid that is attached to the indicated moiety via its main-chain amino or mono-substituted amino group. When the amino acid is attached in an —N-linked amino acid, one of the hydrogens that is part of the main-chain amino or mono-substituted amino group is not present and the amino acid is attached via the nitrogen. An —N-linked amino acid can be protected at any hydroxyl or carboxyl group that is present on the amino acid. For example, an —N-linked amino acid can contain an ester or an ether group. Suitable amino acid protecting groups include, but are not limited to, methyl esters, ethyl esters, propyl esters, benzyl esters, tert-butyl esters, silyl esters, orthoesters, and oxazoline. As used herein, the term "amino acid" refers to any amino acid (both standard and non-standard amino acids), including, but limited to, α-amino acids β-amino acids, γ-amino acids and δ-amino acids. Examples of suitable amino acids, include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine.

The terms "derivative," "variant," or other similar terms refer to a compound that is an analog of the other compound.

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W Greene and P. G. M. Wuts, Protective Groups in Organic Synthesis, 3. Ed. John Wiley & Sons (1999), and in J. F. W. McOmie, Protective Groups in Organic Chemistry Plenum Press (1973), both of which are hereby incorporated by reference for the limited purpose of disclosing suitable protecting groups The protecting group moiety may be chosen in such a way, that they are stable to certain reaction conditions and readily removed at a convenient stage using methodology known from the art. A non-limiting list of protecting groups include benzyl, substituted benzyl; alkylcarbonyls (e g., t-butoxycarbonyl (BOC)); arylalkylcarbonyls (e.g., benzyloxycarbonyl, benzoyl), substituted methyl ether (e.g. methoxymethyl ether); substituted ethyl ether, a substituted benzyl ether; tetrahydropyranyl ether; silyl ethers (e.g., trimethylsilyl, tnethylsilyl, tnisopropylsilyl, t-butyldimethylsilyl, or t-butyldiphenylsilyl), esters (e.g. benzoate ester), carbonates (e g. methoxymethylcarbonate), sulfonates (e g tosylate, mesylate), acyclic ketal (e g dimethyl acetal); cyclic ketals (e.g., 1,3-dioxane or 1,3-dioxolanes); acyclic acetal; cyclic acetal, acyclic hemiacetal, cyclic hemiacetal, and cyclic dithioketals (e.g., 1,3-dithiane or 1,3-dithiolane).

"Leaving group" as used herein refers to any atom or moiety that is capable of being displaced by another atom or moiety in a chemical reaction. More specifically, in some embodiments, "leaving group" refers to the atom or moiety that is displaced in a nucleophilic substitution reaction hi some embodiments, "leaving groups" are any atoms or moieties that are conjugate bases of strong acids Examples of suitable leaving groups include, but are not limited to, tosylates and halogens Non-limiting characteristics and examples of leaving groups can be found, for example in Organic Chemistry, 2d ed, Francis Carey (1992), pages 328-331, Introduction to Organic Chemistry, 2d ed., Andrew Streitwieser and Clayton Heathcock (1981), pages 169-171; and Organic Chemistry, $5^{th}$ed., John McMurry (2000), pages 398 and 408; all of which are incorporated herein by reference for the limited purpose of disclosing characteristics and examples of leaving groups.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 1972 11:942-944).

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. Examples of prodrugs include compounds that have one or more biologically labile groups attached to the parent drug (e.g., a compound of Formula I and/or a compound of Formula II). For example, one or more biologically labile groups can be attached to a functional group of the parent drug (for example, by attaching one or more biologically labile groups to a phosphate). When more than one biologically labile groups is attached, the biologically labile groups can be the same or different. The biologically labile group(s) can be linked (for example, through a covalent bond), to an oxygen or a heteroatom, such as a phosphorus of a monophosphate, diphosphate, triphosphate, and/or a stabilized phosphate analog containing carbon, nitrogen or sulfur (referred to hereinafter in the present paragraph as "phosphate"). In instances where the prodrug is form by attaching one or more biologically labile groups to the phosphate, removal of the biologically labile group in the host produces a phosphate. The removal of the biologically labile group(s) that forms the prodrug can be accomplished by a variety of methods, including, but not limited to, oxidation, reduction, amination, deamination, hydroxylation, dehydroxylation, hydrolysis, dehydrolysis, alkylation, dealkylation, acylation, deacylation, phosphorylation, dephosphorylation, hydration and/or dehydration. An example, without limitation, of a prodrug would be a compound which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might comprise a short peptide (polyaminoacid) bonded to an acid group where the peptide is metabolized or cleaved to reveal the active moiety. Additional examples of prodrug moieties include the following: R*,R*C(=O)OCH$_2$—, R*C(=O)SCH$_2$CH$_2$—, R*C(=O)SCHR'NH—, phenyl-O—, N-linked amino acids, O-linked amino acids, peptides, carbohydrates, and lipids, wherein each R is independently selected from an alkyl, an alkenyl, an alkynyl, an aryl, an aralkyl, acyl, sulfonate ester, a lipid, an —N-linked amino acid, an —O-linked amino acid, a peptide and a cholesterol. The prodrug can be a carbonate. The carbonate can be a cyclic carbonate. The cyclic carbonate can contain a carbonyl group between two hydroxyl groups that results in the formation of a five or six membered ring. Conventional procedures for the selection and preparation of suitable prodrug derivatives are described, for example, in Design of Prodrugs, (ed. H. Bundgaard, Elsevier, 1985), which is hereby incorporated herein by reference for the limited purpose of describing procedures and preparation of suitable prodrug derivatives.

The term "pro-drug ester" refers to derivatives of the compounds disclosed herein formed by the addition of any of several ester-forming groups that are hydrolyzed under physiological conditions. Examples of pro-drug ester groups include pivaloyloxymethyl, acetoxymethyl, phthalidyl, indanyl and methoxymethyl, as well as other such groups known in the art, including a (5-R-2-oxo-1,3-dioxolen-4-yl) methyl group. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14-21 (1987) (providing examples of esters useful as prodrugs for compounds containing carboxyl groups). Each of the above-mentioned references is herein incorporated by reference for the limited purpose of disclosing ester-forming groups that can form prodrug esters.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, phosphoric acid and the like. Pharmaceutical salts can also be obtained by reacting a compound with an organic acid such as aliphatic or aromatic carboxylic or sulfonic acids, for example acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine, lysine, and the like.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis. The term aryl, as used herein, and unless otherwise specified, refers to phenyl, biphenyl, or naphthyl, and preferably phenyl. The aryl group can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

The term purine or pyrimidine base includes, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 2,6-diaminopurine, 2-chloro-2-aminopurine, inosine, and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, acyl groups such as acetyl and propionyl, methanesulfonyl, and p-toluenesulfonyl.

The term acyl refers to a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group. Acyl can also include a natural or synthetic amino acid moiety.

As used herein, the term "substantially free of" or "substantially in the absence of" refers to a nucleoside composition that includes at least 95% to 98%, or more preferably, 99% to 100%, of the designated enantiomer of that nucleoside.

Similarly, the term "isolated" refers to a nucleoside composition that includes at least 85 or 90% by weight, preferably 95% to 98% by weight, and even more preferably 99% to 100% by weight, of the nucleoside, the remainder comprising other chemical species or enantiomers.

The term "host," as used herein, refers to a unicellular or multicellular organism in which the virus can replicate, including cell lines and animals, and preferably a human. Alternatively, the host can be carrying a part of the viral genome, whose replication or function can be altered by the compounds of the present invention. The term host specifically refers to infected cells, cells transfected with all or part of the viral genome and animals, in particular, primates (including chimpanzees) and humans. Relative to abnormal cellular proliferation, the term "host" refers to unicellular or multicellular organism in which abnormal cellular proliferation can be mimicked. The term host specifically refers to cells that abnormally proliferate, either from natural or unnatural causes (for example, from genetic mutation or genetic engineering, respectively), and animals, in particular, primates (including chimpanzees) and humans. In most animal applications of the present invention, the host is a human patient. Veterinary applications, in certain indications, however, are clearly anticipated by the present invention (such as bovine viral diarrhea virus in cattle, hog cholera virus in pigs, and border disease virus in sheep).

The term "halo", as used herein, unless otherwise indicated, includes fluoro, chloro, bromo or iodo.

The compounds of this invention may contain double bonds. When such bonds are present, the compounds of the invention exist as cis and trans configurations and as mixtures thereof.

Unless otherwise indicated, the alkyl and alkenyl groups referred to herein, as well as the alkyl moieties of other groups referred to herein (e.g., alkoxy), may be linear or branched, and they may also be cyclic (e.g., cyclopropyl, cyclobutyl, cyclopentyl, cyclohexyl or cycloheptyl) or be linear or branched and contain cyclic moieties. Unless otherwise indicated, halogen includes fluorine, chlorine, bromine, and iodine.

$(C_2-C_9)$Heterocycloalkyl when used herein refers to pyrrolidinyl, tetrahydrofuranyl, dihydrofuranyl, tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, chromanyl, etc. One of ordinary skill in the art will understand that the connection of said $(C_2-C_9)$ heterocycloalkyl rings is through a carbon or a $sp^3$ hybridized nitrogen heteroatom.

$(C_2-C_9)$Heteroaryl when used herein refers to furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, benzoxazinyl; etc. One of ordinary skill in the art will understand that the connection of said $(C_2-C_9)$heterocycloalkyl rings is through a carbon atom or a $sp^3$ hybridized nitrogen heteroatom.

$(C_6-C_{10})$aryl when used herein refers to phenyl or naphthyl.

As used herein, the term antiviral nucleoside agent refers to antiviral nucleosides that have anti-HIV activity. The agents can be active against other viral infections as well, so long as they are active against HIV.

The term "antiviral thymidine nucleosides" refers to thymidine analogues with anti-HIV activity, including but not limited to, AZT (zidovudine) and D4T (2',3'-didehydro-3'deoxythymidine (stravudine), and 1-□-D-Dioxolane)thymine (DOT) or their prodrugs.

The term "antiviral guanine nucleosides" refers to guanine analogues with anti-HIV activity, including but not limited to, HBG [9-(4-hydroxybutyl)guanine], lobucavir ([1R(1alpha,2beta,3alpha)]-9-[2,3-bis(hydroxymethyl)cyclobutyl]guanine), abacavir ((1S,4R)-4-[2-amino-6-(cyclopropylamino)-9H-purin-9-yl]-2-cyclopentene-1-methanol sulfate (salt), a prodrug of a G-carbocyclic nucleoside) and additional antiviral guanine nucleosides disclosed in U.S. Pat. No. 5,994,321

The term "antiviral cytosine nucleosides" refers to cytosine analogues with anti-HIV activity, including but not limited to, (−)-2',3'-dideoxy-3'-thiacytidine (3TC) and its 5-fluoro analog [(−)-FTC, Emtricitabine], 2',3'-dideoxycytidine (DDC), Racivir, beta-D-2',3'-didehydro-2',3'-dideoxy-5-fluorocytidine (DFC, D-d4FC, RVT, Dexelvucitabine) and its enantiomer L-D4FC, and apricitabine (APC, AVX754, BCH-10618).

The term "antiviral adenine nucleosides" refers to adenine analogues with anti-HIV activity, including, but not limited to 2',3'-dideoxy-adenosine (ddAdo), 2',3'-dideoxyinosine (DDI), 9-(2-phosphonylmethoxyethyl)adenine (PMEA), 9-R-2-phosphonomethoxypropyl adenine (PMPA, Tenofovir) (K65R is resistant to PMPA), Tenofovir disoproxil fumarate (9-[(R)-2[[bis[[isopropoxycarbonyl)oxy]-methoxy]-phosphinyl]methoxy]propyl]adenine fumarate, TDF), bis(isopropyloxymethylcarbonyl)PMPA [bis(poc) PMPA], GS-9148 (Gilead Sciences) as well as those disclosed in Balzarini, J.; De Clercq, E. Acyclic purine nucleoside phosphonates as retrovirus inhibitors. In: Jeffries D J, De Clercq E., editors. Antiviral chemotherapy. New York, N.Y: John Wiley & Sons, Inc.; 1995. pp. 41-45, the contents of which are hereby incorporated by reference.

The term AZT is used interchangeably with the term zidovudine throughout. Similarly, abbreviated and common names for other antiviral agents are used interchangeably throughout.

As used herein, the term DAPD ((2R,4R)-2-amino-9-[(2-hydroxymethyl)-I, 3-dioxolan-4-yl]adenine) is also intended to include a related form of DAPD known as APD [(−)-β-D-2-aminopurine dioxolane], as well as all optically active forms of DAPD, including optically active forms and racemic forms and its phosphate prodrugs as well as dioxolane-G and the 6-methoxy or 6-chloro derivatives.

As used herein, the term "pharmaceutically acceptable salts" refers to pharmaceutically acceptable salts which, upon administration to the recipient, are capable of providing directly or indirectly, a nucleoside antiviral agent, or that exhibit activity themselves.

As used herein, the term "prodrug," in connection with nucleoside antiviral agents, refers to the 5' and N-acylated, alkylated, or phosphorylated (including mono, di, and triphosphate esters as well as stabilized phosphates and phospholipid) derivatives of nucleoside antiviral agents. In one embodiment, the acyl group is a carboxylic acid ester in which the non-carbonyl moiety of the ester group is selected from straight, branched, or cyclic alkyl, alkoxyalkyl including methoxymethyl, aralkyl including benzyl, aryloxyalkyl including phenoxymethyl, aryl including phenyl optionally substituted by halogen, alkyl, alkyl or alkoxy, sulfonate esters such as alkyl or aralkyl sulphonyl including methanesulfonyl, trityl or monomethoxytrityl, substituted benzyl, trialkylsilyl, or diphenylmethylsilyl. Aryl groups in the esters optimally comprise a phenyl group. The alkyl group can be straight, branched or cyclic and is preferably $C_{1-18}$.

As used herein, the term "resistant virus" refers to a virus that exhibits a three, and more typically, five or greater fold increase in $EC_{50}$ compared to naive virus in a constant cell line, including, but not limited to peripheral blood mononuclear (PBM) cells, or MT2 or MT4 cells.

As used herein, the term "substantially pure" or "substantially in the form of one optical isomer" refers to a composition that includes at least 95% to 98%, or more, preferably 99% to 100%, of a single enantiomer of the JAK inhibitors described herein, and, optionally, to similar concentrations of a single enantiomer of a nucleoside. In a preferred embodiment, the JAK inhibitors are administered in substantially pure form.

I. TREM-1 Inhibitors

TREM-1 is a triggering receptor expressed in myeloid cells. TREM-1 inhibitors may be any compound, chemical, antibody, or peptide, naturally occurring or synthetic, that directly or indirectly decreases the activity of TREM-1. Functionally conservative variations of known TREM-1 inhibitors are also intended to be covered by this description. This includes, for example only, deuterated variations of known inhibitors, inhibitors comprising non-naturally occurring amino-acids, functional variations of peptide inhibitors involving a different sequence of amino acids, inhibitors created by codon variations which code for the same amino-acid sequence of a known inhibitor or functional variation thereof, versions of peptides described herein in which one or more of the amino acids can be, individually, D or L isomers. The invention also includes combinations of L-isoforms with D-isoforms.

Common TREM-1 inhibitors include peptides which may be derived from TREM-1, or TREM-like-transcript-1 ("TLT-1"). Any peptide which competitively binds TREM-1 ligands, thereby reducing TREM-1 expression is a TREM-1 inhibitor. These peptides may be referred to as "decoy receptors."

Patent application EP 2555789A1 discloses peptides that inhibit TREM-1 activity. Examples of such peptides are listed below in Table 1:

TABLE 1

| Polypeptide Name | Sequence | Sequence ID |
| --- | --- | --- |
| TLT-1-CDR2 | SAVDRRAPAGRR | SEQ ID NO 1 |
| TLT-1-CDR3 | CMVDGARGPQILHR | SEQ ID NO 2 |
| LR17 | LQEEDAGEYGCMVDGAR | SEQ ID NO 3 |
| LR6-1 | LQEEDA | SEQ ID NO 4 |
| LR6-2 | EDAGEY | SEQ ID NO 5 |
| LR6-3 | GEYGCM | SEQ ID NO 6 |
| LR12 | LQEEDAGEYGCM | SEQ ID NO 7 |

LR17 is a known, naturally occurring direct inhibitor of TREM-1 which functions by binding and trapping TREM-1 ligand. LR12 is a 12 amino-acid peptide derived from LR17. LR12 is composed of the N-terminal 12 amino-acids from LR17. Research suggests that LR12 is an equivalent TREM-1 inhibitor when compared to LR17.

The F-c portion of human IgG (AdTREM-1Ig) is a soluble inhibitor of TREM-1 function.

LR6-1, LR6-2 and LR6-3 are all 6 amino-acids peptides derived from LR17. These peptides are known to protect mice against polymicrobrias sepsis and may function in the same manner as LR12. Patent application WO 2014 037565 A2 discloses additional peptides derived from TREM-1 and TLT-1 which are known to directly inhibit TREM-1 and decrease TREM-1 associated inflammatory responses.

Additional examples of TREM-1 inhibitors include those disclosed by patent application WO 2015 018936 A1. These include, but are not limited to, antibodies directed to TREM-1 and/or sTREM-1 or TREM-1 and/or sTREM-1 ligand, small molecules inhibiting the function, activity or expression of TREM-1, peptides inhibiting the function, activity or expression of TREM-1, siRNAs directed to TREM-1, shRNAs directed to TREM-1, antisense oligonucleotide directed to TREM-1, ribozymes directed to TREM-1 and aptamers which bind to and inhibit TREM-1.

PCT WO 2011 047097 A2 discloses inhibition of TREM-1 by variant peptides biding to the transmembrane region of the DAP-12 subunit. As described in the published, but later abandoned U.S. patent publications 20090081199 and 20030165875, fusion proteins between human IgG1 constant region and the extracellular domain of mouse TREM-1 or that of human TREM-1 can be used, as a decoy receptor, to inhibit TREM-1. These, and all other, TREM-1 and TLT-1 derived peptides can be stabilized by micelles to increase their effectiveness.

Another TREM-1 inhibitor is TLT-1, as disclosed in Washington, et al., "A TREM family member, TLT-1, is found exclusively in the alpha-granules of megakaryocytes and platelets," Blood. 2004 Aug. 15; 104(4):1042-7.

Additional TREM-1 inhibitors include MicroRNA 294, which has been shown to target TREM-1 by dual-luciferase assay activity.

Additionally, the signaling chain homo-oligomerization (SCHOOL) model of immune signaling can be used to design ligand-independent peptide-based TREM-1 inhibitors.

Naturally-occurring TREM-1 inhibitors include curcumin and diferuloylmethane, a yellow pigment present in turmeric. Inhibition of TREM-1 by curcumin is oxidant independent. Accordingly, curcumin and synthetic curcumin analogs, such as those described in U.S. Publication Nos. 20150087937, 20150072984, 20150011494, 20130190256; 20130156705, 20130296527, 20130224229, 20110229555; and 20030153512; U.S. Pat. Nos. 7,947,687, 8,609,723, and PCT WO 2003105751.

In peripheral blood mononuclear cells, human cathelicidin LL-37 suppresses synergistic responses to TREM-1 and TLR4 stimulation, partly through the inhibition of TREM-1 expression on monocytes.

Treatment of cells with NF-kappaB inhibitors has been shown to abolish the expression of message of TREM-1 induced by LPS and P. aeruginosa. In contrast, the expression of TREM-1 was increased after stimulation with LPS or P. aeruginosa in cells that had gene of PU.1 silenced. Additionally, over-expression of PU. 1 led to inhibition of TREM-1 induction in response to LPS and P. aeruginosa. These data suggest that both these transcription factors are involved in the expression of TREM-1. NF-kappaB functions as a positive regulator whereas PU.1 is a negative regulator of the TREM-1 gene.

Antibodies have been shown to inhibit TREM-1 as well. Representative antibodies are described, for example, in U.S. Publication No. 20130309239 and U.S. Pat. No. 9,000,127.

Each of the peptides described herein can be delivered using nanoparticles.

Each of the peptides described herein can optionally be deuterated at one or more positions.

Each of the peptides described herein can optionally include D-amino acids, and/or tails, such as polylysine tails, to stabilize the peptides. These tails are typically at the C-terminal end of the peptide. The C-terminal modifications can include retention signals, while the N-terminal end can include targeting signals. Common retention signals include the amino acid sequences -KDEL (Lys-Asp-Glu-Leu) and -HDEL (His-Asp-Glu-Leu) at the C-terminus. These tails keep the protein in the endoplasmic reticulum and prevent it from entering the secretory pathway.

Other C-terminal modifications include post-translational modifications, most commonly by adding a lipid anchor to the C-terminus. The lipid anchor allows the protein to be inserted into a membrane without having a transmembrane domain.

Another form of C-terminal modification is prenylation. During prenylation, a farnesyl- or geranylgeranyl-isoprenoid membrane anchor is added to a cysteine residue near the C-terminus. Small, membrane-bound G proteins are often modified this way.

Another form of C-terminal modification is the addition of a phosphoglycan, glycosylphosphatidylinositol (GPI), as a membrane anchor. The GPI anchor is attached to the C-terminus after proteolytic cleavage of a C-terminal propeptide.

II. JAK Inhibitors

In one embodiment, the TREM-1 inhibitors are administered in combination or alternation with JAK inhibitors. Representative JAK inhibitors include those disclosed in U.S. Pat. No. 7,598,257, an example of which is Ruxolitinib (Jakafi, Incyte), which has the structure shown below:

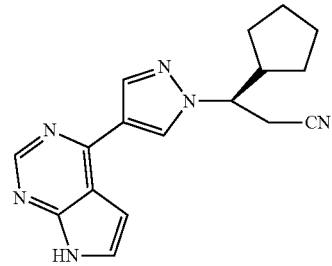 [SMILES: N#CC[C@H](C1CCCC1)n1cc(-c2ncnc3[nH]ccc23)cn1]

Representative JAK inhibitors also include those disclosed in U.S. Pat. Nos. Re 41,783; 7,842,699; 7,803,805; 7,687,507; 7,601,727; 7,569,569; 7,192,963; 7,091,208; 6,890,929, 6,696,567; 6,962,993; 6,635,762; 6,627,754; and 6,610,847, an example of which is Tofacitinib, which has the structure shown below:

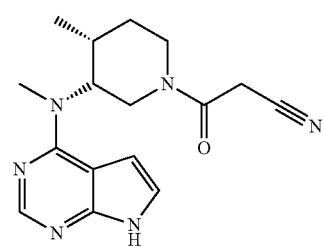

Tofacitinib (Pfizer), and which has the chemical name 3-{(3R,4R)-4 methyl-3-[methyl-(7H-pyrrolo[2,3-d]pyrimidin-4-yl)-amino]-piperidin-1-yl}-3-oxo-propionitrile.

In one embodiment, the compounds have the formula:

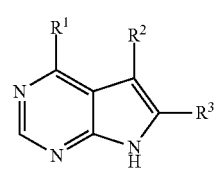

Formula A wherein:
or the pharmaceutically acceptable salt or prodrug thereof, wherein
$R^1$ is a group of the formula

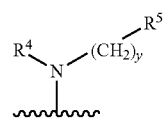

wherein y is 0, 1 or 2;
$R^4$ is selected from the group consisting of hydrogen, $(C_1-C_6)$alkyl, $(C_1-C_6)$alkylsulfonyl, $(C_2-C_6)$alkenyl, $(C_2-C_6)$alkynyl wherein the alkyl, alkenyl and alkynyl groups are optionally substituted by deuterium, hydroxy, amino, trifluoromethyl, $(C_1-C_4)$alkoxy, $(C_1-C_6)$acyloxy, $(C_1-C_6)$alkylamino, $((C_1-C_6)$alkyl$)_2$amino, cyano, nitro, $(C_2-C_6)$alkenyl, $(C_2-C_6)$alkynyl or $(C_1-C_6)$acylamino; or
$R^4$ is $(C_3-C_{10})$cycloalkyl wherein the cycloalkyl group is optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl)$_2$amino, cyano, cyano$(C_1-C_6)$alkyl, trifluoromethyl$(C_1-C_6)$alkyl, nitro, nitro$(C_1-C_6)$alkyl or $(C_1-C_6)$acylamino;

$R^5$ is $(C_2-C_9)$heterocycloalkyl wherein the heterocycloalkyl groups must be substituted by one to five carboxy, cyano, amino, deuterium, hydroxy, $(C_1-C_6)$alkyl, $(C_1-C_6)$alkoxy, halo, $(C_1-C_6)$acyl, $(C_1-C_6)$alkylamino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$ alkynyl, $(C_1-C_6)$alkylamino, amino$(C_1-C_6)$alkyl, hydroxy$(C_1-C_6)$alkyl, $(C_1-C_6)$alkoxy$(C_1-C_6)$alkyl, $(C_1-C_6)$acyloxy $(C_1-C_6)$alkyl, nitro, cyano$(C_1-C_6)$alkyl, halo$(C_1-C_6)$alkyl, nitro$(C_1-C_6)$alkyl, trifluoromethyl, trifluoromethyl $(C_1-C_6)$alkyl, $(C_1-C_6)$acylamino, $(C_1-C_6)$acylamino $(C_1-C_6)$alkyl, $(C_1-C_6)$alkoxy$(C_1-C_6)$acylamino, amino $(C_1-C_6)$acyl, amino$(C_1-C_6)$acyl$(C_1-C_6)$alkyl, $(C_1-C_6)$alkylamino$(C_1-C_6)$acyl, $((C_1-C_6)$alkyl)$_2$amino$(C_1-C_6)$acyl, $R^{15}R^{16}N$—CO—O—, $R^{15}R^{16}N$—CO—$(C_1-C_6)$alkyl, $(C_1-C_6)$alkyl-S(O)$_m$, $R^{15}R^{16}NS(O)_m$, $R^{15}R^{16}NS(O)_m(C_1-C_6)$alkyl, $R^{15}S(O)_mR^{16}N$, $R^{15}S(O)_mR^{16}(C_1-C_6)$alkyl wherein m is 0, 1 or 2 and $R^{15}$ and $R^{16}$ are each independently selected from hydrogen or $(C_1-C_6)$alkyl; or a group of the formula

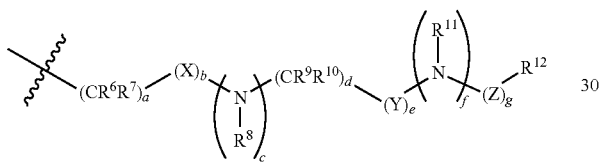

wherein a is 0, 1, 2, 3 or 4;
b, c, e, f and g are each independently 0 or 1;
d is 0, 1, 2, or 3;
X is $S(O)_n$ wherein n is 0, 1 or 2; oxygen, carbonyl or —C(=N-cyano)-;
Y is $S(O)_n$ wherein n is 0, 1 or 2; or carbonyl; and
Z is carbonyl, C(O)O—, C(O)NR— or $S(O)_n$ wherein n is 0, 1 or 2;
$R^6$, $R^7$, $R^8$, $R^9$, $R^{10}$ and $R^{11}$ are each independently selected from the group consisting of hydrogen or $(C_1-C_6)$alkyl optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl)$_2$amino, cyano, cyano$(C_1-C_6)$alkyl, trifluoromethyl$(C_1-C_6)$alkyl, nitro, nitro$(C_1-C_6)$alkyl or $(C_1-C_6)$acylamino;
$R^{12}$ is carboxy, cyano, amino, oxo, deuterium, hydroxy, trifluoromethyl, $(C_1-C_6)$alkyl, trifluoromethyl$(C_1-C_6)$alkyl, $(C_1-C_6)$alkoxy, halo, $(C_1-C_6)$acyl, $(C_1-C_6)$alkylamino, $((C_1-C_6)$alkyl)$_2$amino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$ alkynyl, $(C_1-C_6)$alkylamino, hydroxy$(C_1-C_6)$alkyl, $(C_1-C_6)$alkoxy$(C_1-C_6)$alkyl, $(C_1-C_6)$acyloxy$(C_1-C_6)$alkyl, nitro, cyano$(C_1-C_6)$alkyl, halo$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$alkyl, $(C_1-C_6)$alkylamino$(C_1-C_6)$acyl, $((C_1-C_6)$alkyl)$_2$amino$(C_1-C_6)$acyl, $R^{15}R^{16}N$—CO—O—, $R^{15}R^{16}N$—CO—$(C_1-C_6)$alkyl, $R^{15}C(O)NH$, $R^{15}OC(O)NH$, $R^{15}NHC(O)NH$, $(C_1-C_6)$alkyl-S(O)$_m$, $(C_1-C_6)$alkyl-S(O)$_m$—$(C_1-C_6)$alkyl, $R^{15}R^{16}NS(O)_m$, $R^{15}R^{16}NS(O)_m(C_1-C_6)$alkyl, $R S(O)_mR^{16}N(C_1-C_6)$alkyl wherein m is 0, 1 or 2 and $R^{15}$ and $R^{16}$ are each independently selected from hydrogen or $(C_1-C_6)$alkyl;

$R^2$ and $R^3$ are each independently selected from the group consisting of hydrogen, deuterium, amino, halo, hydroxy, nitro, carboxy, $(C_2-C_6)$alkenyl, $(C_2-C_6)$alkynyl, trifluoromethyl, trifluoromethoxy, $(C_1-C_6)$alkyl, $(C_1-C_6)$alkoxy, $(C_3-C_{10})$cycloalkyl wherein the alkyl, alkoxy or cycloalkyl groups are optionally substituted by one to three groups selected from halo, hydroxy, carboxy, amino $(C_1-C_6)$alkylthio, $(C_1-C_6)$alkylamino, $((C_1-C_6)$alkyl)$_2$amino, $(C_5-C_9)$heteroaryl, $(C_2-C_9)$heterocycloalkyl, $(C_3-C_9)$cycloalkyl or $(C_6-C_{10})$aryl; or $R^2$ and $R^3$ are each independently $(C_3-C_{10})$cycloalkyl, $(C_3-C_{10})$cycloalkoxy, $(C_1-C_6)$alkylamino, $((C_1-C_6)$alkyl)$_2$amino, $(C_6-C_{10})$arylamino, $(C_1-C_6)$alkylthio, $(C_6-C_{10})$arylthio, $(C_1-C_6)$alkylsulfinyl, $(C_6-C_{10})$arylsulfinyl, $(C_1-C_6)$alkylsulfonyl, $(C_6-C_{10})$arylsulfonyl, $(C_1-C_6)$acyl, $(C_1-C_6)$alkoxy-CO—NH—, $(C_1-C_6)$alkylamino-CO—, $(C_5-C_9)$heteroaryl, $(C_2-C_9)$heterocycloalkyl or $(C_6-C_{10})$aryl wherein the heteroaryl, heterocycloalkyl and aryl groups are optionally substituted by one to three halo, $(C_1-C_6)$alkyl, $(C_1-C_6)$alkyl-CO—NH—, $(C_1-C_6)$alkoxy-CO—NH—, $(C_1-C_6)$alkyl-CO—NH—$(C_1-C_6)$alkyl, $(C_1-C_6)$alkoxy-CO—NH—$(C_1-C_6)$alkyl, $(C_1-C_6)$alkoxy-CO—NH—$(C_1-C_6)$alkoxy, carboxy, carboxy$(C_1-C_6)$alkyl, carboxy $(C_1-C_6)$alkoxy, benzyloxycarbonyl$(C_1-C_6)$alkoxy, $(C_1-C_6)$alkoxycarbonyl$(C_1-C_6)$alkoxy, $(C_6-C_{10})$aryl, amino, amino$(C_1-C_6)$alkyl, $(C_1-C_6)$alkoxycarbonylamino, $(C_6-C_{10})$aryl$(C_1-C_6)$alkoxycarbonylamino, $(C_1-C_6)$alkylamino, $((C_1-C_6)$alkyl)$_2$amino, $(C_1-C_6)$alkylamino$(C_1-C_6)$alkyl, $((C_1-C_6)$alkyl)$_2$amino$(C_1-C_6)$alkyl, hydroxy, $(C_1-C_6)$alkoxy, carboxy, carboxy$(C_1-C_6)$alkyl, $(C_1-C_6)$alkoxycarbonyl, $(C_1-C_6)$alkoxycarbonyl$(C_1-C_6)$alkyl, $(C_1-C_6)$alkoxy-CO—NH—, $(C_1-C_6)$alkyl-CO—NH—, cyano, $(C_5-C_9)$heterocycloalkyl, amino-CO—NH—, $(C_1-C_6)$alkylamino-CO—NH—, $((C_1-C_6)$alkyl)$_2$amino-CO—NH—, $(C_6-C_{10})$arylamino-CO—NH—, $(C_5-C_9)$heteroarylamino-CO—NH—, $(C_1-C_6)$alkylamino-CO—NH—$(C_1-C_6)$alkyl, $((C_1-C_6)$alkyl)$_2$amino-CO—NH—$(C_1-C_6)$alkyl, $(C_6-C_{10})$arylamino-CO—NH—$(C_1-C_6)$alkyl, $(C_5-C_9)$heteroarylamino-CO—NH—$(C_1-C_6)$alkyl, $(C_1-C_6)$alkylsulfonyl, $(C_1-C_6)$alkylsulfonylamino, $(C_1-C_6)$alkylsulfonylamino$(C_1-C_6)$alkyl, $(C_6-C_{10})$arylsulfonyl, $(C_6-C_{10})$arylsulfonylamino, $(C_6-C_{10})$arylsulfonylamino$(C_1-C_6)$alkyl, $(C_1-C_6)$alkylsulfonylamino, $(C_1-C_6)$alkylsulfonylamino$(C_1-C_6)$alkyl, $(C_5-C_9)$heteroaryl or $(C_2-C_9)$heterocycloalkyl.

The JAK inhibitors also include compounds of Formula B:

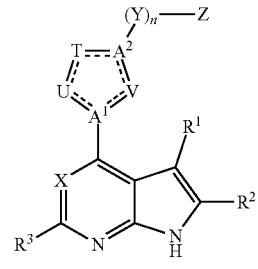

including pharmaceutically acceptable salt forms or prodrugs thereof, wherein:

$A^1$ and $A^2$ are independently selected from C and N;

T, U, and V are independently selected from O, S, N, $CR^5$, and $NR^6$;

wherein the 5-membered ring formed by $A^1$, $A^2$, U, T, and V is aromatic;

X is N or $CR^4$;

Y is $C_{1-8}$ alkylene, $C_{2-8}$ alkenylene, $C_{2-8}$ alkynylene, $(CR^{11}R^{12})_p$—$(C_{3-10}$ cycloalkylene)-$(CR^{11}R^{12})_q$, $(CR^{11}R^{12})_p$-(arylene)-$(CR^{11}R^{12})_q$, $(CR^{11}R^{12})_p$—$(C_{1-10}$ heterocycloalkylene)-$(CR^{11}R^{12})_q$, $(CR^{11}R^{12})_p$-(heteroarylene)-$(CR^{11}R^{12})_q$, $(CR^{11}R^{12})_pO(CR^{11}R^{12})_q$, $(CR^{11}R^{12})_pS(CR^{11}R^{12})_q$, $(CR^{11}R^{12})_pC(O)(CR^{11}R^{12})_q$, $(CR^{11}R^{12})_pC(O)NR_c(CR^{11}R^{12})_q$, $(CR^{11}R^{12})_pC(O)O(CR^{11}R^{12})_q$, $(CR^{11}R^{12})_pOC(O)(CR^{11}R^{12})_q$, $(CR^{11}R^{12})_pOC(O)NR^c(CR^{11}R^{12})_q$, $(CR^{11}R^{12})_pNR^c(CR^{11}R^{12})_q$, $(CR^{11}R^{12})_pNR^cC(O)NR^d(CR^{11}R^{12})_q$, $(CR^{11}R^{12})_pS(O)(CR^{11}R^{12})_q$, $(CR^{11}R^{12})_pS(O)NR^c(CR^{11}R^{12})_q$, $(CR^{11}R^{12})_pS(O)_2(CR^{11}R^{12})_q$, or $(CR^{11}R^{12})_pS(O)_2NR^c(CR^{11}R^{12})_q$, wherein said $C_{1-8}$ alkylene, $C_{2-8}$ alkenylene, $C_{2-8}$ alkynylene, cycloalkylene, arylene, heterocycloalkylene, or heteroarylene, is optionally substituted with 1, 2, or 3 substituents independently selected from -$D^1$-$D^2$-$D^3$-$D^4$;

Z is H, halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, ≡C—$R^1$, =N—$R^1$, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, $C(=NOH)R^b$, $C(=NO(C_{1-6}alkyl)R^b$, and $S(O)_2NR^cR^d$, wherein said $C_{1-8}$ alkyl, $C_{2-8}$ alkenyl, or $C_{2-8}$ alkynyl, is optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $N_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, $C(=NOH)R^b$, $C(=NO(C_{1-6}$ alkyl))$R^b$, and $S(O)_2NR^cR^d$;

wherein when Z is H, n is 1;

or the —$(Y)_n$—Z moiety is taken together with i) $A^2$ to which the moiety is attached, ii) $R^5$ or $R^6$ of either T or V, and iii) the C or N atom to which the $R^5$ or $R^6$ of either T or V is attached to form a 4- to 20-membered aryl, cycloalkyl, heteroaryl, or heterocycloalkyl ring fused to the 5-membered ring formed by $A^1$ $A^2$, U, T, and V, wherein said 4- to 20-membered aryl, cycloalkyl, heteroaryl, or heterocycloalkyl ring is optionally substituted by 1, 2, 3, 4, or 5 substituents independently selected from —$(W)_m$-Q;

W is $C_{1-8}$ alkylenyl, $C_{2-8}$ alkenylenyl, $C_{2-8}$ alkynylenyl, O, S, C(O), $C(O)NR^{c'}$, C(O)O, OC(O), $OC(O)NR^c$, $NR^{c'}$, $NR^{c'}C(O)NR^{d'}$, S(O), $S(O)NR^{c'}$, $S(O)_2$, or $S(O)_2NR^{c'}$;

Q is H, halo, CN, $NO_2$, $C_{1-8}$ alkyl, $C_{2-8}$ alkenyl, $C_{2-8}$ alkynyl, $C_{1-8}$ haloalkyl, halosulfanyl, aryl, cycloalkyl, heteroaryl, or heterocycloalkyl, wherein said $C_{1-8}$ alkyl, $C_{2-8}$ alkenyl, $C_{2-8}$ alkynyl, $C_{1-8}$ haloalkyl, aryl, cycloalkyl, heteroaryl, or heterocycloalkyl is optionally substituted with 1, 2, 3 or 4 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^2$, CN, $NO_2$, $OR^{a'}$, $SR^{a'}$, $C(O)R^{b'}$, $C(O)NR^{c'}R^{d'}$, $C(O)OR^{a'}$, $OC(O)R^{b'}$, $OC(O)NR^{c'}R^{d'}$, $NR^{c'}R^{d'}$, $NR^{c'}C(O)R^{b'}$, $NR^{c'}C(O)NR^{c'}R^{d'}$, $NR^{c'}C(O)OR^{a'}$, $S(O)R^{b'}$, $S(O)NR^{c'}R^{d'}$, $S(O)_2R^{b'}$, $NR^{c'}S(O)_2R^{b'}$, and $S(O)_2NR^{c'}R^{d'}$;

$Cy^1$ and $Cy^2$ are independently selected from aryl, heteroaryl, cycloalkyl, and heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, CN, $NO_2$, $OR^{a''}$, $SR^{a''}$, $C(O)R^{b'''}$, $C(O)NR^{c'}R^{d''}$, $C(O)OR^{a''}$, $OC(O)R^{b''}$, $OC(O)NR^{c'}R^{d''}$, $NR^{c'}$, $R^{d''}$, $NR^{c'}C(O)R^{b''}$, $NR^{c''}C(O)OR^{a''}$, $NR^{c''}S(O)R^{b''}$, $NR^{c''}S(O)_2R^{b''}$, $S(O)R^{b'''}$, $S(O)NR^{c''}R^{d''}$, $S(O)_2R^{b''}$, and $S(O)_2NR^{c''}R^{d''}$;

$R^1$, $R^2$, $R^3$, and $R^4$ are independently selected from H, halo, $C_{1-4}$ alkyl, $C_{2-4}$ alkenyl, $C_{2-4}$ alkynyl, $C_{1-4}$ haloalkyl, halosulfanyl, aryl, cycloalkyl, heteroaryl, heterocycloalkyl, CN, $NO_2$, $OR^7$, $SR^7$, $C(O)R^8$, $C(O)NR^9R^{10}$, $C(O)OR^7OC(O)R^8$, $OC(O)NR^9R^{10}$, $NR^9R^{10}$, $NR^9C(O)R^8$, $NR^cC(O)OR^7$, $S(O)R^8$, $S(O)NR^9R^{10}$, $S(O)_2R^8$, $NR^9S(O)_2R^8$, and $S(O)_2NR^9R^{10}$;

$R^5$ is H, halo, $C_{1-4}$ alkyl, $C_{2-4}$ alkenyl, $C_{2-4}$ alkynyl, $C_{1-4}$ haloalkyl, halosulfanyl, CN, $NO_2$, $OR^7$, $SR^7$, $C(O)R^8$, $C(O)NR^9R^{10}$, $C(O)OR^7$, $OC(O)R^8$, $OC(O)NR^9R^{10}$, $NR^9R^{10}$, $NR^9C(O)R^8$, $NR^9C(O)OR^7$, $S(O)R^8$, $S(O)NR^9R^{10}$, $S(O)_2R^8$, $NR^9S(O)_2R^8$, or $S(O)_2NR^9R^{10}$;

$R^6$ is H, $C_{1-4}$ alkyl, $C_{2-4}$ alkenyl, $C_{2-4}$ alkynyl, $C_{1-4}$ haloalkyl, $OR^7$, $C(O)R^8$, $C(O)NR^9R^{10}$, $C(O)OR^7$, $S(O)R^8$, $S(O)NR^9R^{10}$, $S(O)_2R^8$, or $S(O)_2NR^9R^{10}$;

$R^7$ is H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl;

$R^8$ is H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl;

$R^9$ and $R^{10}$ are independently selected from H, $C_{1-10}$ alkyl, $C_{1-6}$ haloalkyl, $C_{2-6}$ alkenyl, $C_{2-6}$ alkynyl, $C_{1-6}$ alkylcarbonyl, arylcarbonyl, $C_{1-6}$ alkyl sulfonyl, arylsulfonyl, aryl, heteroaryl, cycloalkyl, heterocycloalkyl, arylalkyl, heteroarylalkyl, cycloalkylalkyl and heterocycloalkylalkyl;

or $R^9$ and $R^{10}$ together with the N atom to which they are attached form a 4-, 5-, 6- or 7-membered heterocycloalkyl group;

$R^{11}$ and $R^{12}$ are independently selected from H and -$E^1$-$E^2$-$E^3$-$E^4$;

$D^1$ and $E^1$ are independently absent or independently selected from $C_{1-6}$ alkylene, $C_{2-6}$ alkenylene, $C_{2-6}$ alkynylene, arylene, cycloalkylene, heteroarylene, and heterocycloalkylene, wherein each of the $C_{1-6}$ alkylene, $C_{2-6}$ alkenylene, $C_{2-6}$ alkynylene, arylene, cycloalkylene, heteroarylene, and heterocycloalkylene is optionally substituted by 1, 2 or 3 substituents independently selected from halo, CN, $NO_2$, $N_3$, SCN, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, amino, $C_{1-6}$ alkylamino, and $C_{2-8}$ dialkylamino;

$D^2$ and $E^2$ are independently absent or independently selected from $C_{1-6}$ alkylene, $C_{2-6}$ alkenylene, $C_{2-6}$ alkynylene, $(C_{1-6}$ alkylene)$_r$-O—$(C_{1-6}$ alkylene)$_s$, $(C_{1-6}$ alkylene)$_r$-S—$(C_{1-6}$ alkylene)$_s$, $(C_{1-6}$ alkylene)$_r$-$NR^c$—$(C_{1-6}$ alkylene)$_s$, $(C_{1-6}$ alkylene)$_r$-CO—$(C_{1-6}$ alkylene)$_s$, $(C_{1-6}$ alkylene)$_r$-COO—$(C_{1-6}$ alkylene)$_s$, $(C_{1-6}$ alkylene)$_r$-$CONR^c$—$(C_{1-6}$ alkylene)$_s$, $(C_{1-6}$ alkylene)$_r$-SO—$(C_{1-6}$ alkylene)$_s$, $(C_{1-6}$ alkylene)$_r$-$SO_2$—$(C_{1-6}$ alkylene)$_s$, $(C_{1-6}$ alkylene)$_r$-$SONR^c$—$(C_{1-6}$ alkylene)$_s$, and (C$_{1-6}$ alkylene)$_r$-NR$^c$CONR$^f$—(C$_{1-6}$ alkylene)$_s$, wherein each of the C$_{1-6}$ alkylene, C$_{2-6}$ alkenylene, and C$_{2-6}$ alkynylene is optionally substituted by 1, 2 or 3 substituents independently selected from halo, CN, NO$_2$, N$_3$, SCN, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, amino, C$_{1-6}$ alkylamino, and C$_{2-8}$ dialkyl amino;

D$^3$ and E$^3$ are independently absent or independently selected from C$_{1-6}$ alkylene, C$_{2-6}$ alkenylene, C$_{2-6}$ alkynylene, arylene, cycloalkylene, heteroarylene, and heterocycloalkylene, wherein each of the C$_{1-6}$ alkylene, C$_{2-6}$ alkenylene, C$_{2-6}$ alkynylene, arylene, cycloalkylene, heteroarylene, and heterocycloalkylene is optionally substituted by 1, 2 or 3 substituents independently selected from halo, CN, NO$_2$, N$_3$, SCN, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, amino, C$_{1-6}$ alkylamino, and C$_{2-8}$ dialkylamino;

E$^4$ and E$^4$ are independently selected from H, halo, C$_{1-4}$ alkyl, C$_{2-4}$ alkenyl, C$_{2-4}$ alkynyl, C$_{1-4}$ haloalkyl, halosulfanyl, C$_{1-4}$ hydroxyalkyl, C$_{1-4}$ cyanoalkyl, Cy$^1$, CN, NO$_2$, OR$^a$, SR$^a$, C(O)R$^b$, C(O)NR$^c$R$^a$, C(O)OR$^a$, OC(O)R$^b$OC(O)NR$^c$R$^d$ NR$^c$R$^d$, NR$^c$C(O)R$^b$, NR$^c$C(O)NR$^c$R$^d$, NR$^c$C(O)OR$^a$, C(=NR$^i$)NR$^c$R$^d$, NR$^c$C(=NR$^i$)NR$^c$R$^d$, S(O)R$^b$, S(O)NR$^c$R$^d$, S(O)$_2$R$^b$, NR$^c$S(O)$_2$R$^b$, C(=NOH)R$^b$, C(=NO(C$_{1-6}$ alkyl)R$^b$, and S(O)$_2$NR$^c$R$^d$, wherein said C$_{1-8}$ alkyl, C$_{2-8}$ alkenyl, or C$_{2-8}$ alkynyl, is optionally substituted with 1, 2, 3, 4, 5, or 6 substituents independently selected from halo, C$_{1-4}$ alkyl, C$_{2-4}$ alkenyl, C$_{2-4}$ alkynyl, C$_{1-4}$ haloalkyl, halosulfanyl, C$_{1-4}$ hydroxyalkyl, C$_{1-4}$ cyanoalkyl, Cy$^1$, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^i$)NR$^c$R$^d$, NR$^c$C(=NR$^i$)NR$^c$R$^d$, S(O)R$^b$, S(O)NR$^c$R$^d$, S(O)$_2$R$^b$, NR$^c$S(O)$_2$R$^b$, C(=NOH)R$^b$, C(=NO(C$_{1-6}$ alkyl))R$^b$, and S(O)$_2$NR$^c$R$^d$;

R$^a$ is H, Cy$^1$, —(C$_{1-6}$ alkyl)-Cy$^1$, C$_{1-6}$ alkyl, C$_{1-6}$ haloalkyl, C$_{2-6}$ alkenyl, C$_{2-6}$ alkynyl, wherein said C$_{1-6}$ alkyl, C$_{1-6}$ haloalkyl, C$_{2-6}$ alkenyl, or C$_{2-6}$ alkynyl is optionally substituted with 1, 2, or 3 substituents independently selected from OH, CN, amino, halo, C$_{1-6}$ alkyl, C$_{1-6}$ haloalkyl, halosulfanyl, aryl, arylalkyl, heteroaryl, heteroarylalkyl, cycloalkylalkyl and heterocycloalkyl;

R$^b$ is H, Cy$^1$, —(C$_{1-6}$ alkyl)-Cy$^1$, C$_{1-6}$ alkyl, C$_{1-6}$ haloalkyl, C$_{2-6}$ alkenyl, C$_{2-6}$ alkynyl, wherein said C$_{1-6}$ alkyl, C$_{1-61-6}$ haloalkyl, C$_{2-6}$ alkenyl, or C$_{2-6}$ alkynyl is optionally substituted with 1, 2, or 3 substituents independently selected from OH, CN, amino, halo, C$_{1-6}$ alkyl, C$_{1-6}$ haloalkyl, C$_{1-6}$ haloalkyl, halosulfanyl, aryl, arylalkyl, heteroaryl, heteroarylalkyl, cycloalkyl and heterocycloalkyl;

R$^{a'}$ and R$^{a''}$ are independently selected from H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl and heterocycloalkylalkyl, wherein said C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, C$_{1-6}$ alkyl, C$_{1-6}$ haloalkyl, halosulfanyl, aryl, arylalkyl, heteroaryl, heteroarylalkyl, cycloalkyl and heterocycloalkyl;

R$^{b'}$ and R$^{b''}$ are independently selected from H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl and heterocycloalkylalkyl, wherein said C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, C$_{1-6}$ alkyl, C$_{1-6}$ haloalkyl, C$_{1-6}$ haloalkyl, halosulfanyl, aryl, arylalkyl, heteroaryl, heteroarylalkyl, cycloalkyl and heterocycloalkyl;

R$^c$ and R$^d$ are independently selected from H, Cy$^1$, —(C$_{1-6}$ alkyl)-Cy$^1$, C$_{1-10}$ alkyl, C$_{1-6}$ haloalkyl, C$_{2-6}$ alkenyl, C$_{2-6}$ alkynyl, wherein said C$_{1-10}$ alkyl, C$_{1-6}$ haloalkyl, C$_{2-6}$ alkenyl, or C$_{2-6}$ alkynyl, is optionally substituted with 1, 2, or 3 substituents independently selected from Cy$^1$, —(C$_{1-6}$ alkyl)-Cy$^1$, OH, CN, amino, halo, C$_{1-6}$ alkyl, C$_{1-6}$ haloalkyl, C$_{1-6}$ haloalkyl, and halosulfanyl;

or R$^c$ and R$^d$ together with the N atom to which they are attached form a 4-, 5-, 6- or 7-membered heterocycloalkyl group optionally substituted with 1, 2, or 3 substituents independently selected from Cy$^1$, —(C$_{1-6}$ alkyl)-Cy$^1$, OH, CN, amino, halo, C$_{1-6}$ alkyl, C$_{1-6}$ haloalkyl, C$_{1-6}$ haloalkyl, and halosulfanyl;

R$^{c'}$ and R$^{d'}$ are independently selected from H, C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl and heterocycloalkylalkyl, wherein said C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, C$_{1-6}$ alkyl, C$_{1-6}$ haloalkyl, C$_{1-6}$ haloalkyl, halosulfanyl, aryl, arylalkyl, heteroaryl, heteroarylalkyl, cycloalkyl and heterocycloalkyl;

or R$^{c'}$ and R$^{d'}$ together with the N atom to which they are attached form a 4-, 5-, 6- or 7-membered heterocycloalkyl group optionally substituted with 1, 2, or 3 substituents independently selected from OH, CN, amino, halo, C$_{1-6}$ alkyl, C$_{1-6}$ haloalkyl, C$_{1-6}$ haloalkyl, halosulfanyl, aryl, arylalkyl, heteroaryl, heteroarylalkyl, cycloalkyl and heterocycloalkyl;

R$^{c''}$ and R$^{d''}$ are independently selected from H, C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl and heterocycloalkylalkyl, wherein said C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, C$_{1-6}$ alkyl, C$_{1-6}$ haloalkyl, halosulfanyl, C$_{1-6}$ haloalkyl, aryl, arylalkyl, heteroaryl, heteroarylalkyl, cycloalkyl and heterocycloalkyl;

or R$^{c'''}$ and R$^{d'''}$ together with the N atom to which they are attached form a 4-, 5-, 6- or 7-membered heterocycloalkyl group optionally substituted with 1, 2, or 3 substituents independently selected from OH, CN, amino, halo, C$_{1-6}$ alkyl, C$_{1-6}$ haloalkyl, C$_{1-6}$ haloalkyl, halosulfanyl, aryl, arylalkyl, heteroaryl, heteroarylalkyl, cycloalkyl and heterocycloalkyl;

R$^i$ is H, CN, NO$_2$, or C$_{1-6}$ alkyl;

R$^e$ and R$^f$ are independently selected from H and C$_{1-6}$ alkyl;

R$^i$ is H, CN, or NO$_2$;

m is 0 or 1;

n is 0 or 1;

p is 0, 1, 2, 3, 4, 5, or 6;

q is 0, 1, 2, 3, 4, 5 or 6;

r is 0 or 1; and s is 0 or 1.

Additional JAK inhibitors include CEP-701 (Lestaurtinib, Cephalon Technology), a JAK 2 FL3 kinase, AZD1480 (Astra Zeneca), a JAK 2 inhibitor, LY3009104/INCB28050 (Eli Lilly, Incyte) and Baracitanib, a JAK 1/2 inhibitor, Pacritinib/SB1518 (S*BIO), a JAK 2 inhibitor, VX-509 (Vertex), a JAK 3 inhibitor, GLPG0634 (Galapagos), a JAK 1 inhibitor, INC424 (Novartis), a JAK inhibitor, R-348 (Rigel), a JAK 3 inhibitor, CYT387 (YM Bioscience), a JAK1/2 inhibitor, TG 10138, a JAK 2 inhibitor, AEG 3482 (Axon), a JAK inhibitor, and pharmaceutically-acceptable salts and prodrugs thereof.

Lestaurtinib has the following formula:

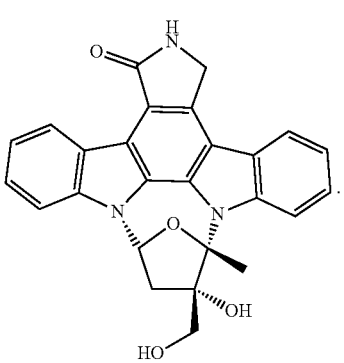

AEG 3482 has the following formula:

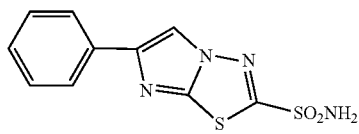 [SMILES: NS(=O)(=O)c1nn2cc(-c3ccccc3)nc2s1]

TG 10138 has the following formula:

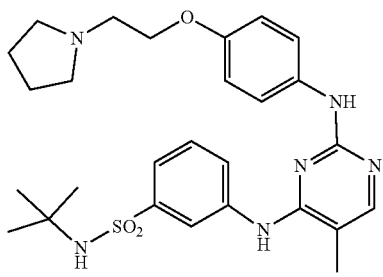 [SMILES: Cc1cnc(Nc2ccc(OCCN3CCCC3)cc2)nc1Nc1cccc(S(=O)(=O)NC(C)(C)C)c1]

CYT387 has the following formula:

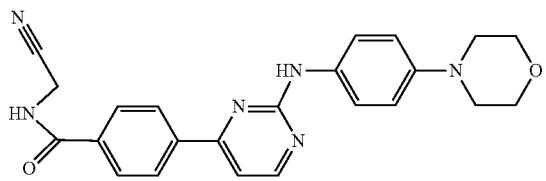 [SMILES: N#CCNC(=O)c1ccc(-c2ccnc(Nc3ccc(N4CCOCC4)cc3)n2)cc1]

AZD1480 has the following formula:

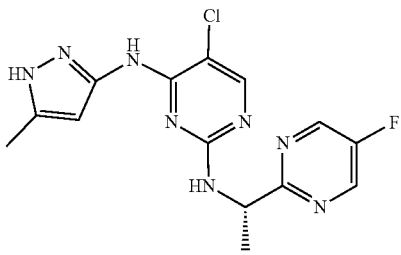 [SMILES: Cc1cc(Nc2nc(N[C@@H](C)c3ncc(F)cn3)ncc2Cl)n[nH]1]

LY3009104 is believed to be (R)-3-(4-(7H-pyrrolo[2,3-d]pyrimidin-4-yl)-1H-pyrazol-1-yl-3-cyclopentyl-propanenitrile Pacritinib has the following formula:

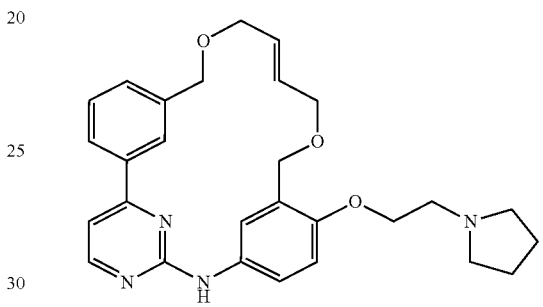

The compounds include those described in U.S. Publication Nos. 20110020469; 20110118255; 20100311743; 20100310675; 20100280026; 20100160287; 20100081657; 20100081645; 20090181938; 20080032963; 20070259869; and 20070249031.

The compounds also include those described in U.S. Publication Nos. 20110251215; 20110224157; 20110223210; 20110207754; 20110136781; 20110086835; 20110086810; 20110082159; 20100190804; 20100022522; 20090318405; 20090286778; 20090233903; 20090215766; 20090197869; 20090181959; 20080312259; 20080312258; 20080188500; and 20080167287; 20080039457.

The compounds also include those described in U.S. Publication Nos. 20100311693; 20080021013; 20060128780; 20040186157; and 20030162775.

The compounds also include those described in U.S. Publication Nos. 20110245256; 20100009978; 20090098137; and 20080261973.

The compounds also include those described in U.S. Publication No. 20110092499. Representative compounds include:

7-iodo-N-(4-morpholinophenyl)thieno[3,2-d]pyrimidin-2-amine
7-(4-aminophenyl)-N-(4-morpholinophenyl)thieno[3,2-d]pyrimidin-2-amine
N-(4-(2-(4-morpholinophenylamino)thieno[3,2-d]pyrimidin-7-yl)phenyl)acrylamide
7-(3-aminophenyl)-N-(4-morpholinophenyl)thieno[3,2-d]pyrimidin-2-amine
N-(3-(2-(4-morpholinophenylamino)thieno[3,2-d]pyrimidin-7-yl)phen-yl)acrylamide
N-(4-morpholinophenyl)thieno[3,2-d]pyrimidin-2-amine
methyl 2-(4-morpholinophenylamino)thieno[3,2-d]pyrimidine-7-carboxylate
N-(4-morpholinophenyl)-5H-pyrrolo[3,2-d]pyrimidin-2-amine 7-(4-amino-3-methoxyphenyl)-N-(4-morpholinophenyl)thieno[3,2-d]pyrimidin-2-amine
4-(2-(4-morpholinophenylamino)thieno[3,2-d]pyrimidin-7-yl)benzenesulfonamide
N,N-dimethyl-3-(2-(4-morpholinophenylamino)thieno[3,2-d]pyrimidin-7-yl)benzenesulfonamide
1-ethyl-3-(2-methoxy-4-(2-(4-morpholinophenylamino)thieno[3,2-d]pyrimidin-7-yl)phenyl)urea
N-(4-(2-(4-morpholinophenylamino)thieno[3,2-d]pyrimidin-7-yl)phenyl)methanesulfonamide
2-methoxy-4-(2-(4-morpholinophenylamino)thieno[3,2-d]pyrimidin-7-yl)phenol
2-cyano-N-(3-(2-(4-morpholinophenylamino)thieno[3,2-d]pyrimidin-7-yl)phenyl)acetamide
N-(cyanomethyl)-2-(4-morpholinophenylamino)thieno[3,2-d]pyrimidine-7-carboxamide
N-(3-(2-(4-morpholinophenylamino)thieno[3,2-d]pyrimidin-7-yl)phenyl)methanesulfonamide
1-ethyl-3-(4-(2-(4-morpholinophenylamino)thieno[3,2-d]pyrimidin-7-yl)-2-(trifluoromethoxy)phenyl)urea
N-(3-nitrophenyl)-7-phenylthieno[3,2-d]pyrimidin-2-amine
7-iodo-N-(3-nitrophenyl)thieno[3,2-d]pyrimidin-2-amine
N1-(7-(2-ethylphenyl)thieno[3,2-d]pyrimidin-2-yl)benzene-1,3-diamine
N-tert-butyl-3-(2-(4-morpholinophenylamino)thieno[3,2-d]pyrimidin-7-yl)benzenesulfonamide
N1-(7-iodothieno[3,2-d]pyrimidin-2-yl)benzene-1,3-diamine
7-(4-amino-3-(trifluoromethoxy)phenyl)-N-(4-morpholinophenyl)thieno[3,2-d]pyrimidin-2-amine
7-(2-ethylphenyl)-N-(4-morpholinophenyl)thieno[3,2-d]pyrimidin-2-amine
N-(3-(2-(4-morpholinophenylamino)thieno[3,2-d]pyrimidin-7-yl)phenyl-)acetamide
N-(cyanomethyl)-N-(3-(2-(4-morpholinophenylamino)thieno[3,2-d]pyrimidin-7-yl)phenyl)methanesulfonamide
N-(cyanomethyl)-N-(4-(2-(4-morpholinophenylamino)thieno[3,2-d]pyrimidin-7-yl)phenyl)methanesulfonamide
N-(3-(5-methyl-2-(4-morpholinophenylamino)-5H-pyrrolo[3,2-d]pyrimidin-7-y-1)phenyl)methanesulfonamide
4-(5-methyl-2-(4-morpholinophenylamino)-5H-pyrrolo[3,2-d]pyrimidin-7-yl)benzenesulfonamide
N-(4-(5-methyl-2-(4-morpholinophenylamino)-5H-pyrrolo[3,2-d]pyrimidin-7-y-1)phenyl)methanesulfonamide
7-iodo-N-(4-morpholinophenyl)-5H-pyrrolo[3,2-d]pyrimidin-2-amine
7-(2-isopropylphenyl)-N-(4-morpholinophenyl)thieno[3,2-d]pyrimidin-2-amine
7-bromo-N-(4-morpholinophenyl)thieno[3,2-d]pyrimidin-2-amine
N7-(2-isopropylphenyl)-N2-(4-morpholinophenyl)thieno[3,2-d]pyrimidine-2,7-diamine
N7-(4-isopropylphenyl)-N2-(4-morpholinophenyl)thieno[3,2-d]pyrimidine-2,7-diamine
7-(5-amino-2-methylphenyl)-N-(4-morpholinophenyl)thieno[3,2-d]pyrimidin-2-amine
N-(cyanomethyl)-4-(2-(4-morpholinophenylamino)thieno[3,2-d]pyrimidin-7-yl)benzamide
7-iodo-N-(3-morpholinophenyl)thieno[3,2-d]pyrimidin-2-amine
7-(4-amino-3-nitrophenyl)-N-(4-morpholinophenyl)thieno[3,2-d]pyrimidin-2-amine
7-(2-methoxypyridin-3-yl)-N-(4-morpholinophenyl)thieno[3,2-d]pyrimidin-2-amine
(3-(7-iodothieno[3,2-d]pyrimidin-2-ylamino)phenyl)methanol
N-tert-butyl-3-(2-(3-morpholinophenylamino)thieno[3,2-d]pyrimidin-7-yl)benzenesulfonamide
N-tert-butyl-3-(2-(3-(hydroxymethyl)phenylamino)thieno[3,2-d]pyrimidin-7-yl)benzenesulfonamide
N-(4-morpholinophenyl)-7-(4-nitrophenylthio)-5H-pyrrolo[3,2-d]pyrimidin-2-amine
N-tert-butyl-3-(2-(3,4,5-trimethoxyphenylamino)thieno[3,2-d]pyrimidin-7-yl)benzenesulfonamide
7-(4-amino-3-nitrophenyl)-N-(3,4-dimethoxyphenyl)thieno[3,2-d]pyrimidin-2-amine
N-(3,4-dimethoxyphenyl)-7-(2-methoxypyridin-3-yl)thieno[3,2-d]pyrimidin-2-amine
N-tert-butyl-3-(2-(3,4-dimethoxyphenylamino)thieno[3,2-d]pyrimidin-7-yl)benzenesulfonamide
7-(2-aminopyrimidin-5-yl)-N-(3,4-dimethoxyphenyl)thieno[3,2-d]pyrimidin-2-amine
N-(3,4-dimethoxyphenyl)-7-(2,6-dimethoxypyridin-3-yl)thieno[3,2-d]pyrimidin-2-amine
N-(3,4-dimethoxyphenyl)-7-(2,4-dimethoxypyrimidin-5-yl)thieno[3,2-d]pyrimidin-2-amine
7-iodo-N-(4-(morpholinomethyl)phenyl)thieno[3,2-d]pyrimidin-2-amine
N-tert-butyl-3-(2-(4-(morpholinomethyl)phenylamino)thieno[3,2-d]pyrimidin-7-yl)benzenesulfonamide
2-cyano-N-(4-methyl-3-(2-(4-morpholinophenylamino)thieno[3,2-d]pyrimidin-7-yl)phenyl)acetamide
ethyl 3-(2-(4-morpholinophenylamino)thieno[3,2-d]pyrimidin-7-yl)benzoate
7-bromo-N-(4-(2-(pyrrolidin-1-yl)ethoxy)phenyl)thieno[3,2-d]pyrimidin-2-amine
N-(3-(2-(4-(2-(pyrrolidin-1-yl)ethoxy)phenylamino)thieno[3,2-d]pyrimidin-7-yl)phenyl)acetamide
N-(cyanomethyl)-3-(2-(4-morpholinophenylamino)thieno[3,2-d]pyrimidin-7-yl)benzamide
N-tert-butyl-3-(2-(4-morpholinophenylamino)thieno[3,2-d]pyrimidin-7-yl)benzamide
N-tert-butyl-3-(2-(4-(1-ethylpiperidin-4-yloxy)phenylamino)thieno[3,2-d]pyrimidin-7-yl)benzenesulfonamide
tert-butyl-4-(2-(4-(morpholinomethyl)phenylamino)thieno[3,2-d]pyrimidin-7-yl)-1H-pyrazole-1-carboxylate
7-bromo-N-(4-((4-ethylpiperazin-1-yl)methyl)phenyl)thieno[3,2-d]pyrimidin-2-amine
N-tert-butyl-3-(2-(4-((4-ethylpiperazin-1-yl)methyl)phenylamino)thieno[3,2-d]pyrimidin-7-yl)benzenesulfonamide
N-(4-((4-ethylpiperazin-1-yl)methyl)phenyl)-7-(1H-pyrazol-4-yl)thieno[3,2-d]pyrimidin-2-amine
N-(cyanomethyl)-3-(2-(4-(morpholinomethyl)phenylamino)thieno[3,2-d]pyrimidin-7-yl)benzamide
N-tert-butyl-3-(2-(4-(2-(pyrrolidin-1-yl)ethoxy)phenylamino)thieno[3,2-d]-pyrimidin-7-yl)benzenesulfonamide
tert-butyl pyrrolidin-1-yl)ethoxy)phenylamino)thieno[3,2-d]pyrimidin-7-yl)benzylcarbamate
3-(2-(4-(2-(pyrrolidin-1-yl)ethoxy)phenylamino)thieno[3,2-d]pyrimidin-7-yl)benzenesulfonamide
7-(3-chloro-4-fluorophenyl)-N-(4-(2-(pyrrolidin-1-yl)ethoxy)phenyl)thieno-[3,2-d]pyrimidin-2-amine
tert-butyl 4-(2-(4-(1-ethylpiperidin-4-yloxy)phenylamino)thieno[3,2-d]pyrimidin-7-yl-)-1H-pyrazole-1-carboxylate
7-(benzo[d][1,3]dioxol-5-yl)-N-(4-(morpholinomethyl)phenyl)thieno[3,2-d]p-yrimidin-2-amine
tert-butyl 5-(2-(4-(morpholinomethyl)phenylamino)thieno[3,2-d]pyrimidin-7-yl)-1H-indole-1-carboxylate
7-(2-aminopyrimidin-5-yl)-N-(4-(morpholinomethyl)phenyl)thieno[3,2-d]pyrimidin-2-amine tert-butyl 4-(2-(4-(morpholinomethyl)phenylamino)thieno[3,2-d]pyrimidin-7-yl)-5,6-di-hydropyridine-1(2H)-carboxylate tert-butyl morpholinomethyl)phenylamino)thieno[3,2-d]pyrimidin-7-yl)benzylcarbamate N-(3-(2-(4-(morpholinomethyl)phenylamino)thieno[3,2-d]pyrimidin-7-yl)-phenyl)acetamide N-(4-(2-(4-(morpholinomethyl)phenylamino)thieno[3,2-d]pyrimidin-7-yl)phenyl)acetamide N-(3-(2-(4-(morpholinomethyl)phenylamino)thieno[3,2-d]pyrimidin-7-yl)phenyl)methanesulfonamide 7-(4-(4-methylpiperazin-1-yl)phenyl)-N-(4-(morpholinomethyl)phenyl)thieno-[3,2-d]pyrimidin-2-amine N-(2-methoxy-4-(2-(4-(morpholinomethyl)phenylamino)thieno[3,2-d]pyrimidin-7-yl)phenyl)acetamide 7-bromo-N-(3,4,5-trimethoxyphenyl)thieno[3,2-d]pyrimidin-2-amine (3-(2-(3,4,5-trimethoxyphenylamino)thieno[3,2-d]pyrimidin-7-yl)phenyl)methanol (4-(2-(3,4,5-trimethoxyphenylamino)thieno[3,2-d]pyrimidin-7-yl)phenyl)methanol (3-(2-(4-morpholinophenylamino)thieno[3,2-d]pyrimidin-7-yl)phenyl)methanol (4-(2-(4-morpholinophenylamino)thieno[3,2-d]pyrimidin-7-yl)phenyl)methanol N-(pyrrolidin-1-yl)ethoxy)phenylamino)thieno[3,2-d]pyrimidin-7-yl)benzyl)methanesulfonamide tert-butyl morpholinomethyl)phenylamino)thieno[3,2-d]pyrimidin-7-yl)benzylcarbamate N-(4-(morpholinomethyl)phenyl)-7-(3-(piperazin-1-yl)phenyl)thieno[3,2-d]pyrimidin-2-amine 7-(6-(2-morpholinoethylamino)pyridin-3-yl)-N-(3,4,5-trimethoxyphenyl)thieno[3,2-d]pyrimidin-2-amine 7-(2-ethylphenyl)-N-(4-(2-(pyrrolidin-1-yl)ethoxy)phenyl)thieno[3,2-d]pyrimidin-2-amine 7-(4-(aminomethyl)phenyl)-N-(4-(morpholinomethyl)phenyl)thieno[3,2-d]pyrimidin-2-amine N-(4-(1-ethylpiperidin-4-yloxy)phenyl)-7-(1H-pyrazol-4-yl)thieno[3,2-d]pyrimidin-2-amine N-(2,4-dimethoxyphenyl)-7-phenylthieno[3,2-d]pyrimidin-2-amine 7-bromo-N-(3,4-dimethoxyphenyl)thieno[3,2-d]pyrimidin-2-amine N-(3,4-dimethoxyphenyl)-7-phenylthieno[3,2-d]pyrimidin-2-amine R348 (Rigel) is defined in Velotta et al., "A novel JAK3 inhibitor, R348, attenuates chronic airway allograft rejection," Transplantation. 2009 Mar. 15; 87(5):653-9.

The present invention also relates to the pharmaceutically acceptable acid addition salts of compounds of Formulas A and B, as well as the additional JAK inhibitors described herein. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of Formulas A and B. The chemical bases that may be used as reagents to prepare pharmaceutically acceptable base salts of those compounds of Formulas A and B that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The compounds of this invention include all conformational isomers (e.g., cis and trans isomers. The compounds of the present invention have asymmetric centers and therefore exist in different enantiomeric and diastereomeric forms. This invention relates to the use of all optical isomers and stereoisomers of the compounds of the present invention, and mixtures thereof, and to all pharmaceutical compositions and methods of treatment that may employ or contain them. In this regard, the invention includes both the E and Z configurations. The compounds of Formulas A and B can also exist as tautomers. This invention relates to the use of all such tautomers and mixtures thereof.

This invention also encompasses pharmaceutical compositions containing prodrugs of compounds of the Formulas A and B, and their use in treating or preventing HIV. This invention also encompasses methods of treating or preventing viral infections that can be treated or prevented by protein kinase inhibitors, such as the enzyme Janus Kinase 1, 2, or 3, comprising administering prodrugs of compounds of the Formulas A and B. Compounds of Formulas A and B having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of Formulas A and B. The amino acid residues include the 20 naturally occurring amino acids commonly designated by three letter symbols and also include, 4-hydroxyproline, hydroxylysine, demosine, isodemosine, 3-methylhistidine, norvlin, beta-alanine, gamma-aminobutyric acid, citrulline, homocysteine, homoserine, ornithine and methioine sulfone. Prodrugs also include compounds wherein carbonates, carbamates, amides and alkyl esters that are covalently bonded to the above substituents of Formulas A and B through the carbonyl carbon prodrug sidechain.

III. Combinations of TREM-1 Inhibitors and Other Antiviral Agents

In one embodiment, the compositions include antiretroviral TREM-1 inhibitors as described herein and one or more additional antiviral agents.

In one aspect of this embodiment, the TREM-1 inhibitors and additional antiviral agents are administered in combination or alternation, and in one aspect, in a manner in which both agents act synergistically against the virus. The compositions and methods described herein can be used to treat patients infected with a drug resistant form of HIV, specifically, a form including the M184V/I, multidrug resistant viruses (e.g., Q151M), K65R mutation, Thymidine analog mutations (TAMS), and the like. TAMS include, but are not limited to, mutations at reverse transcriptase (RT) positions 41, 67, 70, 210, 215, and 219, which confer clinically significant resistance to each of the nucleoside RT inhibitors with the exception of 3TC.

While not wishing to be bound to a particular theory, it is believed that the TREM-1 inhibitors described herein function in a way not associated with heretofore known antiretroviral therapy, in that the compounds do not act in the same way as NRTI, NNRTI, protease inhibitors, integrase inhibitors, entry inhibitors, and the like, all of which interfere directly with a step in the viral replication cycle. Rather, they act in an intracellular manner, in a way that is not likely to provoke resistance. More specifically, the mechanism is independent and distinct from direct modulation or interference with the viral replication cycle itself, and therefore lacks a selective pressure to confer emergence of drug resistant virus.

Further, the combination of the TREM-1 inhibitors described herein, and one or more additional antiviral agents, can help prevent the development of viral resistance to other antiviral agents. Therefore, co-formulation of the TREM-1 inhibitors with these additional antiviral agents can function as a "resistance repellent" for the various mutations associated with conventional therapy, and provides better therapy than either alone.

In one aspect of this embodiment, a combination therapy is administered that has the capability of attacking HIV in a variety of mechanisms. That is, the combination therapy includes an effective amount of at least one adenine, cytosine, thymine, and guanosine nucleoside antiviral, as well as one or more additional agents other than NRTI that inhibit HIV viral loads via a different mechanism. Examples include reverse transcriptase inhibitors, protease inhibitors, fusion inhibitors, entry inhibitors, attachment inhibitors, polymerase inhibitors, and integrase inhibitors such as integrase inhibitors such as raltegravir (Isentress) or MK-0518, GS-9137 (Gilead Sciences), GS-8374 (Gilead Sciences), or GSK-364735.

It is believed that this therapy, particularly when administered at an early stage in the development of HIV infection, has the possibility of eliminating HIV infection in a patient. That is, the presence of the different nucleosides and additional agents minimizes the ability of the virus to adapt its reverse transcriptase and develop resistance to any class of nucleoside antiviral nucleosides (i.e., adenine, cytosine, thymidine, or guanine), because it would be susceptible to at least one of the other nucleoside antiviral agents that are present, and/or the additional non-NRTI therapeutic agent. In addition the lipophilic character of certain agents would allow them to penetrate certain compartments where virus could replicate (e.g., brain, testicles, gut).

Representative agents are described in more detail below.

Attachment and Fusion Inhibitors

Attachment and fusion inhibitors are anti-HIV drugs which are intended to protect cells from infection by HIV by preventing the virus from attaching to a new cell and breaking through the cell membrane. These drugs can prevent infection of a cell by either free virus (in the blood) or by contact with an infected cell. These agents are susceptible to digestive acids, so are commonly delivered by break them down, most of these drugs are given by injections or intravenous infusion.

Examples are shown in the table that follows:
Entry Inhibitors (Including Fusion Inhibitors)

| Brand Name | Generic Name | Abbreviation | Experimental Code | Pharmaceutical Company |
|---|---|---|---|---|
| Fuzeon™ | enfuvirtide | | T-20 | Trimeris |
| | | | T-1249 | Trimeris |
| | | | AMD-3100 | AnorMED, Inc. |
| | CD4-IgG2 | | PRO-542 | Progenics Pharmaceuticals |
| | | | BMS-488043 | Bristol-Myers Squibb |
| | aplaviroc | | GSK-873, 140 | GlaxoSmithKline |
| | Peptide T | | | Advanced Immuni T, Inc. |
| | | | TNX-355 | Tanox, Inc. |
| | maraviroc | | UK-427, 857 | Pfizer |
| CXCR4 Inhibitor | | | | |
| | AMD070 | | AMD11070 | AnorMED, Inc. |
| CCR5 antagonist | | | | |
| Vicriroc | | SCH-D | SCH-417690 | Schering-Plough |

Additional fusion and attachment inhibitors in human trials include AK602, AMD070, BMS-378806, HGS004, INCB9471, PRO 140, Schering C, SP01A, and TAK-652.

AK602 is a CCR5 blocker being developed by Kumamoto University in Japan.

AMD070 by AnorMed blocks the CXCR4 receptor on CD4 T-cells to inhibit HIV fusion.

BMS-378806 is an attachment inhibitor that attaches to gp120, a part of HIV.

HGS004 by Human Genome Sciences, is a monoclonal antibody CCR5 blocker.

INCB 9471 is sold by Incyte Corporation.

PRO 140 by Progenics blocks fusion by binding to a receptor protein on the surface of CD4 cells.

SP01A by Samaritan Pharmaceuticals is an HIV entry inhibitor.

TAK-652 by Takeda blocks binding to the CCR5 receptor.

Polymerase Inhibitors

The DNA polymerization activity of HIV-1 reverse transcriptase (RT) can be inhibited by at least three mechanistically distinct classes of compounds. Two of these are chain terminating nucleoside analogs (NRTIs) and allosteric non-nucleoside RT inhibitors (NNRTIs). The third class includes pyrophosphate mimetics such as foscarnet (phosphonoformic acid, PFA).

The reverse transcriptase has a second enzymatic activity, ribonuclease H (RNase H) activity, which maps to a second active site in the enzyme. RNase H activity can be inhibited by various small molecules (polymerase inhibitors).

Examples include diketo acids, which bind directly to the RNase H domain, or compounds like PFA, which are believed to bind in the polymerase domain.

Examples of these compounds are listed in the tables that follow.

HIV Therapies: Nucleoside/Nucleotide Reverse Transcriptase Inhibitors (NRTIs)

| Brand Name | Generic Name | Abbreviation | Experimental Code | Pharmaceutical Company |
|---|---|---|---|---|
| | Dapavir, 2,6-Dianinopurine dioxolane | DAPD | | RFS Pharma |
| Retrovir® | zidovudine | AZT or ZDV | | GlaxoSmithKline |
| Epivir® | lamivudine | 3TC | | GlaxoSmithKline |
| Combivir® | zidovudine + lamivudine | AZT + 3TC | | GlaxoSmithKline |

-continued

| Brand Name | Generic Name | Abbreviation | Experimental Code | Pharmaceutical Company |
|---|---|---|---|---|
| Trizivir ® | abacavir + zidovudine + lamivudine | ABC + AZT + 3TC | | GlaxoSmithKline |
| Ziagen ® | abacavir | ABC | 1592U89 | GlaxoSmithKline |
| Epzicom ™ | abacavir + lamivudine | ABC + 3TC | | GlaxoSmithKline |
| Hivid ® | lzalcitabine | ddC | | Hoffmann-La Roche |
| Videx ® | didanosine: buffered versions | ddI | BMY-40900 | Bristol-Myers Squibb |
| Entecavir | baraclude | | | Bristol-Myers Squibb |
| Videx ® EC | didanosine: delayed-release capsules | ddI | | Bristol-Myers Squibb |
| Zerit ® | stavudine | d4T | BMY-27857 | Bristol-Myers Squibb |
| Viread ™ | tenofovir disoproxil fumarate (DF) | TDF or Bis(POC) PMPA | | Gilead Sciences |
| GS-7340 | Tenofovir alafenamide fumarate (TAF) | TAF | | Gilead Sciences |
| Emtriva ® | emtricitabine | (−)-FTC | | Gilead Sciences |
| Truvada ® | Viread + Emtriva | TDF + (−)-FTC | | Gilead Sciences |
| EFdA 4'-ethynyl-2-fluoro-2'-deoxyadenosine | | | | Merck |
| Atripla ™ | | TDF + (−)-FTC + Sustiva ® | | Gilead/BMS/Merck |
| | Amdoxovir | DAPD, AMDX | | RFS Pharma LLC |
| Apricitabine | AVX754 | | SPD 754 | Avexa Ltd |
| | Alovudine | FLT | MIV-310 | Medivir |
| | Elvucitabine | L-FD4C | ACH-126443, SN1461, SN1212 | Achillion Koronis |
| | KP-1461 | | | |
| | Racivir | RCV | | Emory University |
| | | DOT | | Emory University |
| Dexelvucitabine | Reverset | D-D4FC, DFC | DPC 817 GS9148 and prodrugs thereof | Emory University Gilead Sciences |

HIV Therapies: Non-Nucleoside Reverse Transcriptase Inhibitors (NNRTIs)

| Brand Name | Generic Name | Abbreviation | Experimental Code | Pharmaceutical Company |
|---|---|---|---|---|
| Viramune ® | nevirapine | NVP | BI-RG-587 | Boehringer Ingelheim |
| Rescriptor ® | delavirdine | DLV | U-90152S/T | Pfizer |
| Sustiva ® | efavirenz | EFV | DMP-266 | Bristol-Myers Squibb |
| | (+)-calanolide A | | | Sarawak Medichem |
| | capravirine | CPV | AG-1549 or S-1153 | Pfizer |
| | | | DPC-083 | Bristol-Myers Squibb |
| | | | TMC-125 | Tibotec-Virco Group |
| | | | TMC-278 | Tibotec-Virco Group |
| | | | IDX12899 | Idenix |
| | | | IDX12989 | Idenix |
| RDEA806 | | | | Ardea Bioscience, Inc. |
| MK-4965 | | | | Merck |

Integrase Inhibitors

Representative integrase inhibitors include globoidnan A, L-000870812, S/GSK1349572, S/GSK1265744, Raltegravir and Elvitegravir with or without a pharmacokinetic (PK) booster such as ritonavir or Gilead's pharmacoenhancing agent (also referred to as a PK booster), GS 9350.

Suitable integrase inhibitors include those described in:

U.S. patent application Ser. No. 11/595,429, entitled "HIV INTEGRASE INHIBITORS" filed in the name of B. Narasimhulu Naidu, et al. on Nov. 10, 2006 and published on May 17, 2007 as U.S. Publication No. 20070111985 and assigned to Bristol-Meyers Squibb Company.

U.S. patent application Ser. No. 11/561,039, entitled "HIV INTEGRASE INHIBITORS" filed in the name of B. Narasimhulu Naidu, et al. on Nov. 17, 2006 and published on Jun. 7, 2007 as U.S. Publication No. 20070129379 and assigned to Bristol-Meyers Squibb Company.

U.S. patent application Ser. No. 11/599,580, entitled "HIV INTEGRASE INHIBITORS" filed in the name of B. Narasimhulu Naidu, et al. on Nov. 14, 2006 and published on May 17, 2007 as U.S. Publication No. 20070112190 and assigned to Bristol-Meyers Squibb Company.

U.S. patent application Ser. No. 11/754,462, entitled "HIV INTEGRASE INHIBITORS" filed in the name of B. Narasimhulu Naidu, et al. on May 29, 2007 and published on Dec. 6, 2007 as U.S. Publication No. 20070281917 and assigned to Bristol-Meyers Squibb Company.

U.S. patent application Ser. No. 11/768,458, entitled "HIV INTEGRASE INHIBITORS" filed in the name of Michael A. Walker, et al. on Jun. 26, 2007 and published Jan. 3, 2008 as U.S. Publication No. 20080004265 and assigned to Bristol-Meyers Squibb Company.

U.S. patent application Ser. No. 12/132,145, entitled "HIV INTEGRASE INHIBITORS" filed in the name of B. Narasimhulu Naidu, et al. on Jun. 3, 2008; published on Dec. 11, 2008 as U.S. Publication No. 20080306051 and assigned to Bristol-Meyers Squibb Company.

U.S. patent application Ser. No. 11/505,149, entitled "BICYCLIC HETEROCYCLES AS HIV INTEGRASE INHIBITORS" filed in the name of B. Narasimhulu Naidu, et al. on Aug. 16, 2006 and published on Dec. 7, 2006 as U.S. Publication No. 20060276466.

U.S. patent application Ser. No. 11/590,637, entitled "HIV INTEGRASE INHIBITORS" filed in the name of B. Narasimhulu Naidu, et al. on Oct. 31, 2006 and published on May 17, 2007 as U.S. Publication No. 20070111984 and assigned to Bristol-Meyers Squibb Company.

U.S. patent application Ser. No. 12/162,975, entitled "USE OF 6-(3-CHLORO-2-FLUOROBENZYL)-1-[(2S)-1-HYDROXY-3-METHYLBUTAN-2-YL]-7-METHOXY-4-OXO-1,4-DIHYDROQUINOLINE-3-CARBOXYLIC ACID OR SALT THEREOF FOR TREATING RETROVIRUS INFECTION" filed in the name of Yuji Matsuzaki, et al. on Feb. 1, 2007 and published on Jan. 15, 2009 as U.S. Publication No. 20090018162.

U.S. patent application Ser. No. 11/767,021, entitled "6-(HETEROCYCLYL-SUBSTITUTED BENZYL)-4-OXO-QUINOLINE COMPOUND AND USE THEREOF AS HIV INTEGRASE INHIBITOR" filed in the name of Motohid, Satoh, et al. on Jun. 22, 2007 and published on Aug. 28, 2008 as U.S. Publication No. 20080207618.

U.S. patent application Ser. No. 12/042,628, entitled "USE OF QUINOLINE DERIVATIVES WITH ANTI-INTEGRASE EFFECT AND APPLICATIONS THEREOF" filed in the name of Aurelia Mousnier, et al. on Mar. 5, 2008 and published on Jul. 3, 2008 as U.S. Publication No. 20080161350 and assigned to Bioalliance Pharma SA.

U.S. patent application Ser. No. 12/169,367, entitled "NOVEL PYRIMIDINECARBOXAMIDE DERIVATIVES" filed in the name of Scott L. Harbeson on Jul. 8, 2008 and published on Feb. 5, 2009 as U.S. Publication No. 20090035324.

U.S. patent application Ser. No. 10/587,857, entitled "NAPHTHYRIDINE DERIVATIVES HAVING INHIBITORY ACTIVITY AGAINST HIV INTEGRASE" filed in the name of Teruhiko Taishi, et al. on Feb. 2, 2005 and published on Sep. 10, 2009 as U.S. Publication No. 20090227621.

U.S. patent application Ser. No. 11/500,387, entitled "NITROGEN-CONTAINING HETEROARYL COMPOUNDS HAVING INHIBITORY ACTIVITY AGAINST HIV INTEGRASE" filed in the name of Masahiro Fuji, et al. on Aug. 8, 2006 and published on Dec. 28, 2006 as U.S. Publication No. 20060293334.

U.S. patent application Ser. No. 12/097,859, entitled "METHODS FOR IMPROVING THE PHARMACOKINETICS OF HIV INTEGRASE INHIBITORS" filed in the name of Brian P. Kearney, et al. on Dec. 29, 2006 and published on Sep. 17, 2009 as U.S. Publication No. 20090233964 and assigned to Gilead Sciences, Inc.

U.S. patent application Ser. No. 11/807,303, entitled "PRE-ORGANIZED TRICYCLIC INTEGRASE INHIBITOR COMPOUNDS" filed in the name of James M. Chen, et al. on May 25, 2007 and published on Jan. 29, 2009 as U.S. Publication No. 20090029939 and assigned to Gilead Sciences, Inc.

U.S. patent application Ser. No. 10/587,601, entitled "HIV INTEGRASE INHIBITORS" filed in the name of Philip Jones, et al. on Mar. 1, 2005 and published on Jul. 12, 2007 as U.S. Publication No. 20070161639 and assigned to Merck and Co., Inc.

U.S. patent application Ser. No. 10/592,222, entitled "HIV INTEGRASE INHIBITORS" filed in the name of Peter D. Jones, et al. on Mar. 4, 2005 and published on Jan. 10, 2008 as U.S. Publication No. 20080009490 and assigned to Merck and Co., Inc.

U.S. patent application Ser. No. 11/992,531, entitled "HIV INTEGRASE INHIBITORS" filed in the name of Vincenzo Summa, et al. on Sep. 26, 2006 and published on Sep. 3, 2009 as U.S. Publication No. 20090221571 and assigned to Merck and Co., Inc.

U.S. patent application Ser. No. 10/587,682, entitled "HIV INTEGRASE INHIBITORS" filed in the name of Wei Han, et al. on Mar. 9, 2005 and published on Aug. 2, 2007 as U.S. Publication No. 20070179196 and assigned to Merck and Co., Inc.

U.S. patent application Ser. No. 11/641,508, entitled "N-SUBSTITUTED HYDROXYPYRIMIDINONE CARBOXAMIDE INHIBITORS OF HIV INTEGRASE" filed in the name of Benedetta Crescenzi, et al. on Dec. 19, 2006 and published on May 31, 2007 as U.S. Publication No. 20070123524 and assigned to Merck and Co., Inc.

U.S. patent application Ser. No. 11/435,671, entitled "INTEGRASE INHIBITOR COMPOUNDS" filed in the name of Zhenhong R. Cai, et al. on May 16, 2006 and published on Mar. 29, 2007 as U.S. Publication No. 20070072831 and assigned to Gilead Sciences, Inc.

U.S. patent application Ser. No. 11/804,041, entitled "INTEGRASE INHIBITORS" filed in the name of Zhenhong R. Cai, et al. on May 16, 2007 and published on Mar. 6, 2008 as U.S. Publication No. 20080058315 and assigned to Gilead Sciences, Inc.

U.S. patent application Ser. No. 11/880,854, entitled "NOVEL HIV REVERSE TRANSCRIPTASE INHIBI- TORS" filed in the name of Hongyan Guo, et al. on Jul. 24, 2007 and published on Mar. 20, 2008 as U.S. Publication No. 20080070920 and assigned to Gilead Sciences, Inc.

U.S. patent application Ser. No. 10/585,504, entitled "PYRIMIDYL PHOSPHONATE ANTIVIRAL COMPOUNDS AND METHODS OF USE" filed in the name of Haolun Jin, et al. on Nov. 1, 2005 and published on Jun. 26, 2008 as U.S. Publication No. 20080153783 and assigned to Gilead Sciences, Inc.

U.S. patent application Ser. No. 11/579,772, entitled "HIV INTEGRASE INHIBITORS" filed in the name of John S. Wai, et al. on May 3, 2005 and published on Nov. 20, 2008 as U.S. Publication No. 20080287394 and assigned to Merck and Co., Inc.

U.S. patent application Ser. No. 10/591,914, entitled "HIV INTEGRASE INHIBITORS" filed in the name of Matthew M. Morrissette, et al. on Mar. 4, 2005 and published on Jun. 12, 2008 as U.S. Publication No. 20080139579 and assigned to Merck and Co., Inc.

U.S. patent application Ser. No. 11/629,153, entitled "HIV INTEGRASE INHIBITORS" filed in the name of John S. Wai, et al. on Jun. 3, 2005 and published on Jun. 18, 2008 as U.S. Publication No. 20080015187 and assigned to Merck and Co., Inc.

U.S. patent application Ser. No. 12/043,636, entitled "HIV INTEGRASE INHIBITORS, PHARMACEUTICAL COMPOSITIONS AND METHOD FOR THEIR USE" filed in the name of Qiyue Hu, et al. on Mar. 6, 2008 and published on Sep. 11, 2008 as U.S. Publication No. 20080221154 and assigned to Pfizer, Inc.

PCT WO 2007/019098, entitled "HIV INTEGRASE INHIBITORS," listing SmithKline Beecham Corporation, Shionogi & Co. Ltd., and Takashi Kawasuji as applicants, and Brian Johns as an inventor, published on Feb. 15, 2007.

U.S. patent application Ser. No. 12/306,198, entitled "MODULATORS OF PHARMACOKINETIC PROPERTIES OF THERAPEUTICS" filed in the name of Desai, Manoj C., et al. and was published on Nov. 26, 2009 as U.S. Publication No. 20090291952 and is assigned to Gilead Sciences, Inc.

U.S. patent application Ser. No. 12/274,107, entitled, "INTEGRASE INHIBITORS" filed Nov. 19, 2008 in the name of Jabri, Salman Y., et al. and was published on Nov. 26, 2009 as U.S. Publication No. 20090291921 and is assigned to Gilead Sciences, Inc.

U.S. patent application Ser. No. 12/215,605 "ANTIVIRAL COMPOUNDS" filed on Jun. 26, 2008 in the name of Cho, Aesop, et al., and was published on Oct. 15, 2009 as U.S. Publication No. 20090257978 and is assigned to Gilead Sciences, Inc.

U.S. patent application Ser. No. 12/097,859 METHODS FOR IMPROVING THE PHARMACOKINETICS OF HIV INTEGRASE INHIBITORS filed on Dec. 29, 2006 in the name of Kearney; Brian P., et al. and published on Sep. 17, 2009 as U.S. Publication No. 20090233964 and assigned to Gilead Sciences, Inc.

U.S. patent application Ser. No. 11/658,419, entitled "PHOSPHONATE ANALOGS OF HIV INHIBITOR COMPOUNDS" filed Jul. 26, 2005 in the name of Boojamra; Constantine G., et al. and was published on Aug. 13, 2009 as U.S. Publication No. 20090202470 and is assigned to Gilead Sciences, Inc.

U.S. patent application Ser. No. 12/215,601, entitled, "ANTIVIRAL COMPOUNDS" filed on Jun. 26, 2008 in the name of Cottell, Jeromy J., et al. and published on Jul. 23, 2009 as U.S. Publication No. 20090186869 and assigned to Gilead Sciences, Inc.

U.S. patent application Ser. No. 12/217,496 entitled "MODULATORS OF PHARMACOKINETIC PROPERTIES OF THERAPEUTICS" in the name of Desai, Manoj C., et al. and published on Jul. 16, 2009 as U.S. Publication No. 20090181902 and assigned to Gilead Sciences, Inc.

U.S. patent application Ser. No. 12/340,419 entitled "INHIBITORS OF CYTOCHROME P450" filed on Dec. 19, 2008 in the name of Desai, Manoj C. et al. and published on Jul. 9, 2009 as U.S. Publication No. 20090175820 and assigned to Gilead Sciences, Inc.

U.S. patent application Ser. No. 12/195,161 entitled "COMPOSITIONS AND METHODS FOR COMBINATION ANTIVIRAL THERAPY" filed on Aug. 20, 2008 in the name of Dahl, Terrence C. et al. and published on Jun. 4, 2009 as U.S. Publication No. 20090143314 and assigned to Gilead Sciences, Inc.

U.S. patent application Ser. No. 12/208,952 entitled "PROCESS AND INTERMEDIATES FOR PREPARING INTEGRASE INHIBITORS" filed on Sep. 11, 2008 in the name of Dowdy, Eric, et al. and published on Apr. 16, 2009 as U.S. Publication No. 20090099366 and assigned to Gilead Sciences, Inc.

U.S. patent application Ser. No. 12/147,220 entitled "THERAPEUTIC COMPOSITIONS AND METHODS" filed on Jun. 26, 2008 in the name of Kearney, Brian P. et al and published on Apr. 9, 2009 as U.S. Publication No. 20090093482 and assigned to Gilead Sciences, Inc.

U.S. patent application Ser. No. 12/147,041 entitled "THERAPEUTIC COMPOSITIONS AND METHODS" filed on Jun. 26, 2008 in the name of Kearney, Brian P. et al., published on Apr. 9, 2009 as U.S. Publication No. 20090093467 and assigned to Gilead Sciences, Inc.

U.S. patent application Ser. No. 12/215,266 entitled "ANTIVIRAL COMPOUNDS" filed on Jun. 26, 2008 in the name of Cai, Zhenhong R. et al., published Feb. 19, 2009 as U.S. Publication No. 20090047252 and assigned to Gilead Sciences, Inc.

U.S. patent application Ser. No. 12/204,174 entitled "COMPOSITIONS AND METHODS FOR COMBINATION ANTIVIRAL THERAPY" filed on Sep. 4, 2008 in the name of Dahl, Terrence C., et al., published on Feb. 5, 2009 as U.S. Publication No. 20090036408 and assigned to Gilead Sciences, Inc.

U.S. patent application Ser. No. 10/585,504 entitled "PYRIMIDYL PHOSPHONATE ANTIVIRAL COMPOUNDS AND METHODS OF USE" filed on Nov. 1, 2005 in the name of Jin, Haolun et al., published on Jun. 26, 2008 as U.S. Publication No. 20080153783 and assigned to Gilead Sciences, Inc.

U.S. patent application Ser. No. 11/853,606 entitled "PROCESS AND INTERMEDIATES FOR PREPARING INTEGRASE INHIBITORS" filed on Sep. 11, 2007 in the name of Dowdy, Eric, et al, published May 29, 2008 as U.S. Publication No. 20080125594 and assigned to Gilead Sciences, Inc.

U.S. patent application Ser. No. 11/644,811 entitled "PROCESSES AND INTERMEDIATES USEFUL FOR PREPARING INTEGRASE INHIBITOR COMPOUNDS" filed on Dec. 21, 2006 in the name of Evans, Jared W. et al., published on Feb. 14, 2008 as U.S. Publication No. 20080039487 and assigned to Gilead Sciences, Inc.

U.S. patent application Ser. No. 10/586,627 entitled "USE OF ADEFOVIR OR TENOFOVIR FOR INHIBITING MMTV-LIKE VIRUSES INVOLVED IN BREAST CANCER AND PRIMARY BILIARY CIRRHOSIS" filed on Jul. 20, 2007 in the name of Cihlar, Tomas, et al., published on Dec. 6, 2007 as U.S. Publication No. 20070281911 and assigned to Gilead Sciences, Inc.

U.S. patent application Ser. No. 11/435,671 entitled "INTEGRASE INHIBITOR COMPOUNDS" filed on May 16, 2006 in the name of Cai, Zhenhong R. et al., published on Mar. 29, 2007 as U.S. Publication No. 20070072831 and assigned to Gilead Sciences, Inc.

U.S. patent application Ser. No. 11/190,225 entitled "PHOSPHONATE ANALOGS OF HIV INHIBITOR COMPOUNDS" filed on Jul. 26, 2005 in the name of Boojamra, Constantine G. et al., published on Mar. 1, 2007 as U.S. Publication No. 20070049754 and assigned to Gilead Sciences, Inc.

U.S. patent application Ser. No. 10/511,182 entitled "NON NUCLEOSIDE REVERSE TRANSCRIPTASE INHIBITORS" filed on Feb. 28, 2005 in the name of Chen, James M. et al., published on Jun. 15, 2006 as U.S. Publication No. 20060128692 and assigned to Gilead Sciences, Inc.

U.S. patent application Ser. No. 11/033,422 entitled "PYRIMIDYL PHOSPHONATE ANTIVIRAL COMPOUNDS AND METHODS OF USE" filed on Jan. 11, 2005 in the name of Jin, Haolun et al., published on Dec. 22, 2005 as U.S. Publication No. 20050282839 and assigned to Gilead Sciences, Inc.

U.S. patent application Ser. No. 11/040,929 entitled "METHODS OF INHIBITION OF MMTV-LIKE VIRUSES" filed on Jan. 21, 2005 in the name of Cihlar, Tomas et al., published on Oct. 27, 2005 as U.S. Publication No. 20050239753 and assigned to Gilead Sciences, Inc.

U.S. patent application Ser. No. 10/423,496 entitled "CELLULAR ACCUMULATION OF PHOSPHONATE ANALOGS OF HIV PROTEASE INHIBITOR COMPOUNDS" filed on Apr. 25, 2003 in the name of Arimilli, Murty N. et al., published on Sep. 22, 2005 as U.S. Publication No. 20050209197 and assigned to Gilead Sciences, Inc.

U.S. patent application Ser. No. 10/424,130 entitled "NON NUCLEOSIDE REVERSE TRANSCRIPTASE INHIBITORS" filed on Apr. 25, 2003 in the name of Chen, James M. et al., published on Sep. 8, 2005 as U.S. Publication No. 20050197320 and assigned to Gilead Sciences, Inc.

U.S. patent application Ser. No. 10/944,118 entitled "AZA-QUINOLINOL PHOSPHONATE INTEGRASE INHIBITOR COMPOUNDS" filed on Sep. 17, 2004 in the name of Jin, Haolun et al., published on Jun. 23, 2005 as U.S. Publication No. 20050137199 and assigned to Gilead Sciences, Inc.

U.S. patent application Ser. No. 10/903,288 entitled "NUCLEOBASE PHOSPHONATE ANALOGS FOR ANTIVIRAL TREATMENT" filed on Jul. 30, 2004 in the name of Krawczyk, Steven H., published on Mar. 17, 2005 as U.S. Publication No. 20050059637 and assigned to Gilead Sciences, Inc.

U.S. patent application Ser. No. 10/757,141 entitled "COMPOSITIONS AND METHODS FOR COMBINATION ANTIVIRAL THERAPY" filed Jan. 13, 2004 Dahl, Terrance C. et al., published on Nov. 11, 2004 as U.S. Publication No. 20040224917 and assigned to Gilead Sciences, Inc.

U.S. patent application Ser. No. 10/757,122 entitled "COMPOSITIONS AND METHODS FOR COMBINATION ANTIVIRAL THERAPY" filed on Jan. 13, 2004 Dahl, Terrance C. et al., published on Nov. 11, 2004 as U.S. Publication No. 20040224916 and assigned to Gilead Sciences, Inc.

U.S. patent application Ser. No. 10/687,373 entitled "PRE-ORGANIZED TRICYCLIC INTEGRASE INHIBITOR COMPOUNDS" filed on Oct. 16, 2003 in the name of Chen, James M. et al., published on Aug. 26, 2004 as U.S. Publication No. 20040167124 and assigned to Gilead Sciences, Inc.

U.S. patent application Ser. No. 10/687,374 entitled "PRE-ORGANIZED TRICYCLIC INTEGRASE INHIBITOR COMPOUNDS" filed on Oct. 15, 2003 in the name of Chen, James M. et al., published on Aug. 12, 2004 as U.S. Publication No. 20040157804 and assigned to Gilead Sciences, Inc.

U.S. patent application Ser. No. 10/424,186 entitled "METHOD AND COMPOSITIONS FOR IDENTIFYING ANTI-HIV THERAPEUTIC COMPOUNDS" filed on Apr. 25, 2003 in the name of Birkus, Gabriel et al., published on Jun. 24, 2004 as U.S. Publication No. 20040121316 and assigned to Gilead Sciences, Inc.

U.S. patent application Ser. No. 11/820,444 entitled "DIKETO ACIDS WITH NUCLEOBASE SCAFFOLDS: ANTI-HIV REPLICATION INHIBITORS TARGETED AT HIV INTEGRASE" filed on Jun. 19, 2007 in the name of Nair, Vasu et al., published on Nov. 8, 2007 as U.S. Publication No. 20070259823 and assigned to the University of Georgia Research Foundation, Inc.

U.S. patent application Ser. No. 11/047,229 entitled "DIKETO ACIDS WITH NUCLEOBASE SCAFFOLDS: ANTI-HIV REPLICATION INHIBITORS TARGETED AT HIV INTEGRASE" filed on Jan. 31, 2005 in the name of Nair, Vasu et al., published on Aug. 3, 2006 as U.S. Publication No. 20060172973.

U.S. patent application Ser. No. 11/827,959 entitled "PYRIDINONE DIKETO ACIDS: INHIBITORS OF HIV REPLICATION" filed on Jul. 13, 2007 in the name of Nair, Vasu et al., published on Jan. 24, 2008 as U.S. Publication No. 20080020010 and assigned to the University of Georgia Research Foundation, Inc.

Additional integrase inhibitors include L-870,810 (Merck), INH-001 (Inhibitex), L870810 (Merck), PL-2500, composed of pryidoxal 1-5-phosphate derivatives (Procyon) monophores (Sunesis), V-165 (Rega Institute, Belgium), Mycelium integrasone (a fungal polyketide, Merck), GS 9224 (Gilead Sciences), AVX-1 (Avexa), IT1-367, an oxadiazol pre-integrase inhibitor (George Washington University), GSK364735 (GSK Shionogi), GS-9160 (GSK), S-1360 (Shionogi-GlaxoSmithKline Pharmaceuticals LLC), RSC 1838 (GSK/Shionogi), GS-9137 (taken alone or with Norvir) (Gilead), MK-2048 (Merck), S/GSK 1349572 and S/GSK 1265744 (no need for a PK booster) (GSK/Shionogi), 6-(3-chloro-2-fluorobenzyl)-1-[(2S)-1-hydroxy-3-methylbutan-2-yl]-7-methoxy-4-oxo-1,4-dihydroquinoline-3-carboxylic acid (U.S. Patent Application Publication No. 20090018162), S-1360, L-870810, Raltegravir, C-2507 (Merck), BMS 538158 (Bristol Myers Squibb), and L-900564 (Merck).

The structure of L-900564 is shown below:

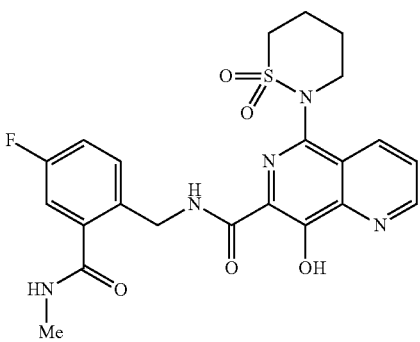 [SMILES: CNC(=O)c1cc(F)ccc1CNC(=O)c1nc(N2CCCCS2(=O)=O)c2cccnc2c1O]

Nair et al., J Med Chem. 2006 Jan. 26; 49(2): 445-447, discloses the following integrase inhibitors:

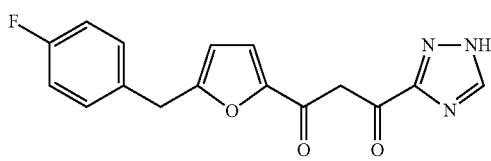

S-1360

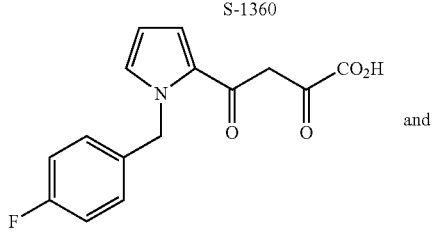

L-731988

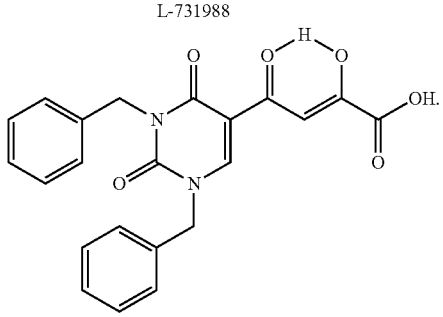

Additional integrase inhibitors are disclosed in Pais et al., J Med Chem. 2002 Jul. 18; 45(15):3184-94.

Several integrase inhibitors are peptides, including those disclosed in Divita et al., Antiviral Research, Volume 71, Issues 2-3, September 2006, Pages 260-267.

Another integrase inhibitor that can be used in the methods of treatment described herein include 118-D-24, which is disclosed, for example, in Vatakis, Journal of Virology, April 2009, p. 3374-3378, Vol. 83, No. 7.

Additional integrase inhibitors include those described in McKeel et al., "Dynamic Modulation of HIV-1 Integrase Structure and Function by Cellular LEDGF Protein, JBC Papers in Press. Published on Sep. 18, 2008 as Manuscript M805843200.

Other representative integrase inhibitors include dicaffeoylquinic acids (DCQAs), such as those disclosed in Zhu et al., "Irreversible Inhibition of Human Immunodeficiency Virus Type 1 Integrase by Dicaffeoylquinic Acids," Journal of Virology, April 1999, p. 3309-3316, Vol. 73, No. 4.

There are also various nucleoside compounds active as integrase inhibitors, including those disclosed in Mazumder, A., N. Neamati, J. P. Sommadossi, G. Gosselin, R. F. Schinazi, J. L. Imbach, and Y. Pommier. 1996. Effects of nucleotide analogues on human immunodeficiency virus type 1 integrase. Mol. Pharmacol. 49:621-628.

Protease Inhibitors

Protease inhibitors treat or prevent HIV infection by preventing viral replication. They act by inhibiting the activity of HIV protease, an enzyme that cleaves nascent proteins for final assembly of new virons. Examples are shown in the table that follows.

HIV Therapies: Protease Inhibitors (PIs)

| Brand Name | Generic Name | Abbreviation | Experimental Code | Pharmaceutical Company |
|---|---|---|---|---|
| Invirase ® | saquinavir (Hard Gel Cap) | SQV (HGC) | Ro-31-8959 | Hoffmann-La Roche |
| Fortovase ® | saquinavir (Soft Gel Cap) | SQV (SGC) | | Hoffmann-La Roche |
| Norvir ® | Ritonavir | RTV | ABT-538 | Abbott Laboratories |
| Crixivan ® | Indinavir | IDV | MK-639 | Merck & Co. |
| Viracept ® | Nelfinavir | NFV | AG-1343 | Pfizer |
| Agenerase ® | amprenavir | APV | 141W94 or VX-478 | GlaxoSmithKline |
| Kaletra ® | lopinavir + ritonavir | LPV | ABT-378/r | Abbott Laboratories |
| Lexiva ® | fosamprenavir | | GW-433908 or VX-175 | GlaxoSmithKline |
| Aptiyus ® | tripanavir | TPV | PNU-140690 | Boehringer Ingelheim |
| Reyataz ® | atazanavir | | BMS-232632 | Bristol-Myers Squibb |
| | brecanavir | | GW640385 | GlaxoSmithKline |
| Prezista ™ | darunavir | | TMC114 | Tibotec |

HIV Therapies: Other Classes of Drugs

| Brand Name | Generic Name | Abbreviation | Experimental Code | Pharmaceutical Company |
|---|---|---|---|---|
| Viread ™ | tenofovir disoproxil fumarate (DF) | | TDF or Bis(POC) PMPA | Gilead Sciences |
| GS-7340 | Tenofovir alafenamide fumarate | | TAF | Gilead Sciences |

Cellular Inhibitors

| Brand Name | Generic Name | Abbreviation | Experimental Code | Pharmaceutical Company |
|---|---|---|---|---|
| Droxia | hydroxyurea | HU | | Bristol-Myers Squibb |

HIV Therapies: Immune-Based Therapies

| Brand Name | Generic Name | Abbreviation | Experimental Code | Pharmaceutical Company |
|---|---|---|---|---|
| Proleukin ® | aldesleukin, or Interleukin-2 | IL-2 | | Chiron Corporation |

-continued

| Brand Name | Generic Name | Abbreviation | Experimental Code | Pharmaceutical Company |
|---|---|---|---|---|
| Remune ® | HIV-1 Immunogen, or Salk vaccine | | AG1661 | The Immune Response Corporation |
| | | | HE2000 | HollisEden Pharmaceuticals |

III. Combination or Alternation HIV-Agents

In general, during alternation therapy, an effective dosage of each agent is administered serially, whereas in combination therapy, an effective dosage of two or more agents is administered together. In alternation therapy, for example, one or more first agents can be administered in an effective amount for an effective time period to treat the viral infection, and then one or more second agents substituted for those first agents in the therapy routine and likewise given in an effective amount for an effective time period.

The dosages will depend on such factors as absorption, biodistribution, metabolism and excretion rates for each drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

Examples of suitable dosage ranges for anti-HIV compounds, including the JAK inhibitors described herein, can be found in the scientific literature and in the Physicians Desk Reference. Many examples of suitable dosage ranges for other compounds described herein are also found in public literature or can be identified using known procedures. These dosage ranges can be modified as desired to achieve a desired result.

IV. Pharmaceutical Compositions

Humans suffering from effects caused by HIV infection can be treated by administering to the patient an effective amount of the compositions described above, in the presence of a pharmaceutically acceptable carrier or diluent, for any of the indications or modes of administration as described in detail herein. The active materials can be administered by any appropriate route, for example, orally, parenterally, enterally, intravenously, intradermally, subcutaneously, transdermally, intranasally or topically, in liquid or solid form.

The active compounds are included in the pharmaceutically acceptable carrier or diluent in an amount sufficient to deliver to a patient a therapeutically effective amount of compound to inhibit viral propagation in vivo, especially HIV propagation, without causing serious toxic effects in the treated patient. While not wishing to be bound to a particular theory, it is believed that the TREM-1 inhibitors will inhibit HIV-1-induced activation of mature monocytes and macrophages, therein 1) reducing permissiveness of infection of bystander cells by reduction of autocrine and paracrine pro-inflammatory events in monocytes/macrophages, 2) reduce the amount of HIV-1 produced per infected macrophage, 3) prevent inflammatory and activation driven trafficking of $CD14^+/CD16^+$ monocytes across the blood-brain-barrier, 4) reduce reservoir size/purge myeloid-derived viral sanctuaries by inhibition of myeloid-driven inflammation that promotes reservoir maintenance, and 5) reduce or eliminate HIV-induced CNS infection and HIV-associated neurocognitive dysfunction by conferring potent, specific inhibition of perivascular macrophage localized HIV-induced activation.

HIV infection, which is similar in pathology to HIV-2 infection, induces a significant increase in TNF-α production in HIV-infected macrophages, for both acute and chronic HIV-1 infection. Increase in TNF-α production is associated with disease progression and viral persistence including maintenance of viral reservoirs, which prevents eradication of HIV-1. TREM-1 inhibitors inhibit TNF-α production. Thereby, TREM-1 inhibitors can be useful in inhibiting the HIV-induced TNF-α production, thereby treating, preventing, or eradicating HIV-1 or HIV-2 infection.

By "inhibitory amount" is meant an amount of active ingredient sufficient to exert an inhibitory effect as measured by, for example, an assay such as the ones described herein.

A preferred dose of the compound for all the above-mentioned conditions will be in the range from about 1 to 75 mg/kg, preferably 1 to 20 mg/kg, of body weight per day, more generally 0.1 to about 100 mg per kilogram body weight of the recipient per day. The effective dosage range of the pharmaceutically acceptable derivatives can be calculated based on the weight of the parent nucleoside or other agent to be delivered. If the derivative exhibits activity in itself, the effective dosage can be estimated as above using the weight of the derivative, or by other means known to those skilled in the art.

The compounds are conveniently administered in unit any suitable dosage form, including but not limited to one containing 7 to 3,000 mg, preferably 70 to 1,400 mg of active ingredient per unit dosage form. An oral dosage of 50 to 1,000 mg is usually convenient.

Ideally, the active ingredient should be administered to achieve peak plasma concentrations of the active compound of from about 0.02 to 70 micromolar, preferably about 0.5 to 10 micromolar. This may be achieved, for example, by the intravenous injection of a 0.1 to 25% solution of the active ingredient, optionally in saline, or administered as a bolus of the active ingredient.

The concentration of active compound in the drug composition will depend on absorption, distribution, metabolism and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible bind agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compounds can be administered as a component of an elixir, suspension, syrup, wafer, chewing gum or the like. A syrup may contain, in addition to the active compounds, sucrose as a sweetening agent and certain preservatives, dyes and colorings and flavors.

The compounds or their pharmaceutically acceptable derivative or salts thereof can also be mixed with other active materials that do not impair the desired action, or with materials that supplement the desired action, such as antibiotics, antifungals, anti inflammatories, protease inhibitors, or other nucleoside or non-nucleoside antiviral agents, as discussed in more detail above. Solutions or suspensions used for parental, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

Liposomal suspensions (including liposomes targeted to infected cells with monoclonal antibodies to viral antigens) are also preferred as pharmaceutically acceptable carriers, these may be prepared according to methods known to those skilled in the art, for example, as described in U.S. Pat. No. 4,522,811. For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

In one embodiment, the composition is a co-formulated pill, tablet, or other oral drug delivery vehicle including one or more of the JAK inhibitors described herein, and optionally including one or more additional antiviral agents.

In another embodiment, the JAK inhibitors described herein are co-formulated with ATRIPLA® (efavirenz 600 mg/emtricitabine [(−)-FTC] 200 mg/tenofovir disoproxil fumarate 300 mg), and, optionally, with a thymidine nRTI such as AZT and a guanine nRTI such as Abacavir (ABC) (or a compound such as DAPD which is deaminated in vivo to form a guanine nRTI, in this case, DXG). Because efavirenz is an NNRTI, tenofovir is an adenine nRTI, (−)-FTC is a cytosine nRTI, and AZT and d4T are thymidine nRTIs, and Abacavir is a guanine nRTI, the combination of the coformulated compounds will provide, in addition to the JAK inhibitors, all four bases (ACTG) plus an additional agent capable of interacting with HIV in a different mechanism.

Controlled Release Formulations

All of the U.S. patents cited in this section on controlled release formulations are incorporated by reference in their entirety.

In one embodiment, the TREM-inhibitors, and, optionally, other anti-HIV compounds, are loaded into liposomes, niosomes, and/or micelles, including but not limited to sterically stabilized phospholipid nanomicelles (SSM), sterically stabilized mixed micelles (SSMM), or sterically-stabilized liposomes (SSL), to achieve an improved biological effect in vivo relative to their being administered without being loaded into these micelles.

The field of biodegradable polymers has developed rapidly since the synthesis and biodegradability of polylactic acid was reported by Kulkarni et al., in 1966 ("Polylactic acid for surgical implants," Arch. Surg., 93:839). Examples of other polymers which have been reported as useful as a matrix material for delivery devices include polyanhydrides, polyesters such as polyglycolides and polylactide-co-glycolides, polyamino acids such as polylysine, polymers and copolymers of polyethylene oxide, acrylic terminated polyethylene oxide, polyamides, polyurethanes, polyorthoesters, polyacrylonitriles, and polyphosphazenes. See, for example, U.S. Pat. Nos. 4,891,225 and 4,906,474 to Langer (polyanhydrides), U.S. Pat. No. 4,767,628 to Hutchinson (polylactide, polylactide-co-glycolide acid), and U.S. Pat. No. 4,530,840 to Tice, et al. (polylactide, polyglycolide, and copolymers). See also U.S. Pat. No. 5,626,863 to Hubbell, et al which describes photopolymerizable biodegradable hydrogels as tissue contacting materials and controlled release carriers (hydrogels of polymerized and crosslinked macromers comprising hydrophilic oligomers having biodegradable monomeric or oligomeric extensions, which are end capped monomers or oligomers capable of polymerization and crosslinking); and PCT WO 97/05185 filed by Focal, Inc. directed to multiblock biodegradable hydrogels for use as controlled release agents for drug delivery and tissue treatment agents.

Degradable materials of biological origin are well known, for example, crosslinked gelatin. Hyaluronic acid has been crosslinked and used as a degradable swelling polymer for biomedical applications (U.S. Pat. No. 4,957,744 to Della Valle et. al.; (1991) "Surface modification of polymeric biomaterials for reduced thrombogenicity," Polym. Mater. Sci. Eng., 62:731 735]).

Many dispersion systems are currently in use as, or being explored for use as, carriers of substances, particularly biologically active compounds. Dispersion systems used for pharmaceutical and cosmetic formulations can be categorized as either suspensions or emulsions. Suspensions are defined as solid particles ranging in size from a few manometers up to hundreds of microns, dispersed in a liquid medium using suspending agents. Solid particles include microspheres, microcapsules, and nanospheres. Emulsions are defined as dispersions of one liquid in another, stabilized by an interfacial film of emulsifiers such as surfactants and lipids. Emulsion formulations include water in oil and oil in water emulsions, multiple emulsions, microemulsions, microdroplets, and liposomes. Microdroplets are unilamellar phospholipid vesicles that consist of a spherical lipid layer with an oil phase inside, as defined in U.S. Pat. Nos. 4,622,219 and 4,725,442 issued to Haynes. Liposomes are phospholipid vesicles prepared by mixing water-insoluble polar lipids with an aqueous solution. The unfavorable entropy caused by mixing the insoluble lipid in the water produces a highly ordered assembly of concentric closed membranes of phospholipid with entrapped aqueous solution.

U.S. Pat. No. 4,938,763 to Dunn, et al., discloses a method for forming an implant in situ by dissolving a nonreactive, water insoluble thermoplastic polymer in a biocompatible, water soluble solvent to form a liquid, placing the liquid within the body, and allowing the solvent to dissipate to produce a solid implant. The polymer solution can be placed in the body via syringe. The implant can assume the shape of its surrounding cavity. In an alternative embodiment, the implant is formed from reactive, liquid oligomeric polymers which contain no solvent and which cure in place to form solids, usually with the addition of a curing catalyst.

A number of patents disclose drug delivery systems that can be used to administer the combination of antiviral agents, or prodrugs thereof. U.S. Pat. No. 5,749,847 discloses a method for the delivery of nucleotides into organisms by electrophoration. U.S. Pat. No. 5,718,921 discloses microspheres comprising polymer and drug dispersed there within. U.S. Pat. No. 5,629,009 discloses a delivery system for the controlled release of bioactive factors. U.S. Pat. No. 5,578,325 discloses nanoparticles and microparticles of nonlinear hydrophilic hydrophobic multiblock copolymers. U.S. Pat. No. 5,545,409 discloses a delivery system for the controlled release of bioactive factors. U.S. Pat. No. 5,494,682 discloses ionically cross-linked polymeric microcapsules.

U.S. Pat. No. 5,728,402 to Andrx Pharmaceuticals, Inc. describes a controlled release formulation that includes an internal phase, which comprises the active drug, its salt or prodrug, in admixture with a hydrogel forming agent, and an external phase which comprises a coating which resists dissolution in the stomach. U.S. Pat. Nos. 5,736,159 and 5,558,879 to Andrx Pharmaceuticals, Inc. discloses a controlled release formulation for drugs with little water solubility in which a passageway is formed in situ. U.S. Pat. No. 5,567,441 to Andrx Pharmaceuticals, Inc. discloses a once-a-day controlled release formulation. U.S. Pat. No. 5,508,040 discloses a multiparticulate pulsatile drug delivery system. U.S. Pat. No. 5,472,708 discloses a pulsatile particle based drug delivery system. U.S. Pat. No. 5,458,888 describes a controlled release tablet formulation, which can be made using a blend having an internal drug containing phase and an external phase, which comprises a polyethylene glycol polymer, which has a weight average molecular weight of from 3,000 to 10,000. U.S. Pat. No. 5,419,917 discloses methods for the modification of the rate of release of a drug form a hydrogel which is based on the use of an effective amount of a pharmaceutically acceptable ionizable compound that is capable of providing a substantially zero-order release rate of drug from the hydrogel. U.S. Pat. No. 5,458,888 discloses a controlled release tablet formulation.

U.S. Pat. No. 5,641,745 to Elan Corporation, plc discloses a controlled release pharmaceutical formulation, which comprises the active drug in a biodegradable polymer to form microspheres or nanospheres. The biodegradable polymer is suitably poly-D,L-lactide or a blend of poly-D,L-lactide and poly-D,L-lactide-co-glycolide. U.S. Pat. No. 5,616,345 to Elan Corporation plc describes a controlled absorption formulation for once a day administration that includes the active compound in association with an organic acid, and a multi-layer membrane surrounding the core and containing a major proportion of a pharmaceutically acceptable film-forming, water insoluble synthetic polymer and a minor proportion of a pharmaceutically acceptable film-forming water soluble synthetic polymer. U.S. Pat. No. 5,641,515 discloses a controlled release formulation based on biodegradable nanoparticles. U.S. Pat. No. 5,637,320 discloses a controlled absorption formulation for once a day administration. U.S. Pat. Nos. 5,580,580 and 5,540,938 are directed to formulations and their use in the treatment of neurological diseases. U.S. Pat. No. 5,533,995 is directed to a passive transdermal device with controlled drug delivery. U.S. Pat. No. 5,505,962 describes a controlled release pharmaceutical formulation.

Prodrug Formulations

The TREM-1 inhibitors, as well as the nucleosides or other compounds which are described herein for use in combination or alternation therapy with the TREM-1 inhibitors or their related compounds, can be administered as an acylated prodrug or a nucleotide prodrug, as described in detail below. Nanoformulations of TREM-1 inhibitors, or flurochrome-conjugated TREM-1 inhibitors at any and all proteins within the TREM-1 inhibitors are within the scope of the invention described herein. Prodrugs designed to modify the peptide sequences described herein are also within the scope of the invention.

Any of the TREM-1 inhibitors, nucleosides, nucleotides or other compounds described herein that contain a hydroxyl or amine function can be administered as a nucleotide prodrug to increase the activity, bioavailability, stability or otherwise alter the properties of the nucleoside. A number of nucleotide prodrug ligands are known. In general, alkylation, acylation or other lipophilic modification of the hydroxyl group of the compound or of the mono, di or triphosphate of the nucleoside will increase the stability of the nucleotide. Examples of substituent groups that can replace one or more hydrogens on the phosphate moiety or hydroxyl are alkyl, aryl, steroids, carbohydrates, including sugars, 1,2-diacylglycerol and alcohols. Many are described in R. Jones and N. Bischofberger, Antiviral Research, 27 (1995) 1 17. Any of these can be used in combination with the disclosed nucleosides or other compounds to achieve a desire effect.

The active nucleoside or other hydroxyl containing compound can also be provided as an ether lipid (and particularly a 5'-ether lipid for a nucleoside), as disclosed in the following references, Kucera, L. S., N. Iyer, E. Leake, A. Raben, Modest E. K., D. L. W., and C. Piantadosi. 1990. "Novel membrane-interactive ether lipid analogs that inhibit infectious HIV-1 production and induce defective virus formation." AIDS Res. Hum. Retroviruses. 6:491 501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest. 1991. "Synthesis and evaluation of novel ether lipid nucleoside conjugates for anti-HIV activity." J. Med. Chem. 34:1408.1414; Hosteller, K. Y., D. D. Richrnan, D. A. Carson, L. M. Stuhmiller, G. M. T. van Wijk, and H. van den Bosch. 1992. "Greatly enhanced inhibition of human immunodeficiency virus type 1 replication in CEM and HT4-6C cells by 3'-deoxythymidine diphosphate dimyristoylglycerol, a lipid prodrug of 3'-deoxythymidine." Antimicrob. Agents Chemother. 36:2025.2029; Hostetler, K. Y., L. M. Stuhmiller, H. B. Lenting, H. van den Bosch, and D. D. Richman, 1990. "Synthesis and antiretroviral activity of phospholipid analogs of azidothymidine and other antiviral nucleosides." J. Biol. Chem. 265:61127.

Nonlimiting examples of U.S. patents that disclose suitable lipophilic substituents that can be covalently incorporated into the nucleoside or other hydroxyl or amine containing compound, preferably at the 5'-OH position of the nucleoside or lipophilic preparations, include U.S. Pat. No. 5,149,794 (Sep. 22, 1992, Yatvin et al.); U.S. Pat. No. 5,194,654 (Mar. 16, 1993, Hostetler et al., U.S. Pat. No. 5,223,263 (Jun. 29, 1993, Hostetler et al.); U.S. Pat. No. 5,256,641 (Oct. 26, 1993, Yatvin et al.); U.S. Pat. No. 5,411,947 (May 2, 1995, Hostetler et al.); U.S. Pat. No. 5,463,092 (Oct. 31, 1995, Hostetler et al.); U.S. Pat. No. 5,543,389 (Aug. 6, 1996, Yatvin et al.); U.S. Pat. No. 5,543,390 (Aug. 6, 1996, Yatvin et al.); U.S. Pat. No. 5,543,391 (Aug. 6, 1996, Yatvin et al.); and U.S. Pat. No. 5,554,728 (Sep. 10, 1996; Basava et-al.), Foreign patent applications that disclose lipophilic substituents that can be attached to the nucleosides of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

Nonlimiting examples of nucleotide prodrugs are described in the following references: Ho, D. H. W. (1973) "Distribution of Kinase and deaminase of 1-β-D-arabinofuranosylcytosine in tissues of man and muse." Cancer Res. 33, 2816 2820; Holy, A. (1993) Isopolar phosphorous-modified nucleotide analogues," In: De Clercq (Ed.), Advances in Antiviral Drug Design, Vol. I, JAI Press, pp. 179 231; Hong, C. I., Nechaev, A., and West, C. R. (1979a) "Synthesis and antitumor activity of 10-D-arabino-furanosylcytosine conjugates of cortisol and cortisone." Biochem. Biophys. Rs. Commun. 88, 1223 1229; Hong, C. I., Nechaev, A., Kirisits, A. J. Buchheit, D. J. and West, C. R. (1980) "Nucleoside conjugates as potential antitumor agents. 3. Synthesis and antitumor activity of 1-(β-D-arabinofuranosyl)cytosine conjugates of corticosteroids and selected lipophilic alcohols." J. Med. Chem. 28, 171 177; Hosteller, K. Y., Stuhmiller, L. M., Lenting, H. B. M. van den Bosch, H. and Richman J Biol. Chem. 265, 6112 6117; Hosteller, K. Y., Carson, D. A. and Richman, D. D. (1991); "Phosphatidylazidothymidine: mechanism of antiretroviral action in CEM cells." J. Biol Chem. 266, 11714 11717; Hosteller, K. Y., Korba, B. Sridhar, C., Gardener, M. (1994a) "Antiviral activity of phosphatidyl-dideoxycytidine in hepatitis B-infected cells and enhanced hepatic uptake in mice." Antiviral Res. 24, 59 67; Hosteller, K. Y., Richman, D. D., Sridhar. C. N. Felgner, P. L. Felgner, J., Ricci, J., Gardener, M. F. Selleseth, D. W. and Ellis, M. N. (1994b) "Phosphatidylazidothymidine and phosphatidyl-ddC: Assessment of uptake in mouse lymphoid tissues and antiviral activities in human immunodeficiency virus-infected cells and in rauscher leukemia virus-infected mice." Antimicrobial Agents Chemother. 38, 2792 2797; Hunston, R. N., Jones, A. A. McGuigan, C., Walker, R. T., Balzarini, J., and DeClercq, E. (1984) "Synthesis and biological properties of some cyclic phosphotriesters derived from 2'-deoxy-5-fluorouridine." J. Med. Chem. 27,440 444; Ji, Y. H., Moog, C., Schmitt, G., Bischoff, P. and Luu, B. (1990); "Monophosphoric acid esters of 7-β-hydroxycholesterol and of pyrimidine nucleoside as potential antitumor agents: synthesis and preliminary evaluation of antitumor activity." J. Med. Chem. 33 2264 2270; Jones, A. S., McGuigan, C., Walker, R. T., Balzarini, J. and DeClercq, E. (1984) "Synthesis, properties, and biological activity of some nucleoside cyclic phosphoramidates." J. Chem. Soc. Perkin Trans. I, 1471 1474; Juodka, B. A. and Smart, J. (1974) "Synthesis of diribonucleoside phosph (P.fwdarw.N) amino acid derivatives." Coll. Czech. Chem. Comm. 39, 363 968; Kataoka, S., Imai, J., Yamaji, N., Kato, M., Saito, M., Kawada, T. and Imai, S. (1989) "Alkylated cAMP derivatives; selective synthesis and biological activities." Nucleic Acids Res. Sym. Ser. 21, 1 2; Kataoka, S., Uchida, "(cAMP) benzyl and methyl triesters." Heterocycles 32, 1351 1356; Kinchington, D., Harvey, J. J., O'Connor, T. J., Jones, B. C. N. M., Devine, K. G., Taylor-Robinson D., Jeffries, D. J. and McGuigan, C. (1992) "Comparison of antiviral effects of zidovudine phosphoramidate and phosphorodiamidate derivatives against HIV and ULV in vitro." Antiviral Chem. Chemother. 3, 107 112; Kodama, K., Morozumi, M., Saithoh, K. I., Kuninaka, H., Yosino, H. and Saneyoshi, M. (1989) "Antitumor activity and pharmacology of 1-β-D-arabinofuranosylcytosine-5'-stearylphosphate; an orally active derivative of 1-β-Darabinofuranosylcytosine." Jpn. J. Cancer Res. 80, 679 685; Korty, M. and Engels, J. (1979) "The effects of adenosine- and guanosine 3',5' phosphoric and acid benzyl esters on guinea-pig ventricular myocardium." Naunyn-Schmiedeberg's Arch. Pharmacol. 310, 103 111; Kumar, A., Goe, P. L., Jones, A. S. Walker, R. T. Balzarini, J. and DeClercq, E. (1990) "Synthesis and biological evaluation of some cyclic phosphoramidate nucleoside derivatives." J. Med. Chem, 33, 2368 2375; LeBec, C., and Huynh-Dinh, T. (1991) "Synthesis of lipophilic phosphate triester derivatives of 5-fluorouridine an arabinocytidine as anticancer prodrugs." Tetrahedron Lett. 32, 6553 6556; Lichtenstein, J., Barner, H. D. and Cohen, S. S. (1960) "The metabolism of exogenously supplied nucleotides by *Escherichia coli*.," J. Biol. Chem. 235, 457 465; Lucthy, J., Von Daeniken, A., Friederich, J. Manthey, B., Zweifel, J., Schlatter, C. and Benn, M. H. (1981) "Synthesis and toxicological properties of three naturally occurring cyanoepithioalkanes". Mitt. Geg. Lebensmittelunters. Hyg. 72, 131 133 (Chem. Abstr. 95, 127093); McGigan, C. Tollerfield, S. M. and Riley, P. a. (1989) "Synthesis and biological evaluation of some phosphate triester derivatives of the anti-viral drug Ara." Nucleic Acids Res. 17, 6065 6075; McGuigan, C., Devine, K. G., O'Connor, T. J., Galpin, S. A., Jeffries, D. J. and Kinchington, D. (1990a) "Synthesis and evaluation of some novel phosphoramidate derivatives of 3'-azido-3'-deoxythymidine (AZT) as anti-HIV compounds." Antiviral Chem. Chemother. 1 107 113; McGuigan, C., O'Connor, T. J., Nicholls, S. R. Nickson, C. and Kinchington, D. (1990b) "Synthesis and anti-HIV activity of some novel substituted dialkyl phosphate derivatives of AZT and ddCyd." Antiviral Chem. Chemother. 1, 355 360; McGuigan, C., Nicholls, S. R., O'Connor, T. J., and Kinchington, D. (1990c) "Synthesis of some novel dialkyl phosphate derivative of 3'-modified nucleosides as potential anti-AIDS drugs." Antiviral Chem. Chemother. 1, 25 33; McGuigan, C., Devin, K. G., O'Connor, T. J., and Kinchington, D. (1991) "Synthesis and anti-HIV activity of some haloalkyl phosphoramidate derivatives of 3'-azido-3'-deoxythylmidine (AZT); potent activity of the trichloroethyl methoxyalaninyl compound." Antiviral Res. 15, 255 263; McGuigan, C., Pathirana, R. N., Balzarini, J. and DeClercq, E. (1993b) "Intracellular delivery of bioactive AZT nucleotides by aryl phosphate derivatives of AZT." J. Med. Chem. 36, 1048 1052.

Alkyl hydrogen phosphate derivatives of the anti-HIV agent AZT may be less toxic than the parent nucleoside analogue. Antiviral Chem. Chemother. 5, 271 277; Meyer, R. B., Jr., Shuman, D. A. and Robins, R. K. (1973) "Synthesis of purine nucleoside 3',5'-cyclic phosphoramidates." Tetrahedron Lett. 269 272; Nagyvary, J. Gohil, R. N., Kirchner, C. R. and Stevens, J. D. (1973) "Studies on neutral esters of cyclic AMP," Biochem. Biophys. Res. Commun.

55, 1072 1077; Namane, A. Gouyette, C., Fillion, M. P., Fillion, G. and Huynh-Dinh, T. (1992) "Improved brain delivery of AZT using a glycosyl phosphotriester prodrug." J. Med. Chem. 35, 3039 3044; Nargeot, J. Nerbonne, J. M. Engels, J. and Leser, H. A. (1983) Natl. Acad. Sci. U.S.A. 80, 2395 2399; Nelson, K. A., Bentrude, W. G. Stser, W. N. and Hutchinson, J. P. (1987) "The question of chair-twist equilibria for the phosphate rings of nucleoside cyclic 3',5'-monophosphates. $^1$HNMR and x-ray crystallographic study of the diastereomers of thymidine phenyl cyclic 3',5'-monophosphate." J. Am. Chem. Soc. 109, 4058 4064; Nerbonne, J. M., Richard, S., Nargeot, J. and Lester, H. A. (1984) "New photoactivatable cyclic nucleotides produce intracellular jumps in cyclic AMP and cyclic GMP concentrations." Nature 301, 74 76; Neumann, J. M., Herv_, M., Debouzy, J. C., Guerra, F. I., Gouyette, C., Dupraz, B. and Huyny-Dinh, T. (1989) "Synthesis and transmembrane transport studies by NMR of a glucosyl phospholipid of thymidine." J. Am. Chem. Soc. 111, 4270 4277; Ohno, R., Tatsumi, N., Hirano, M., Imai, K. Mizoguchi, H., Nakamura, T., Kosaka, M., Takatuski, K., Yamaya, T., Toyama K., Yoshida, T., Masaoka, T., Hashimoto, S., Ohshima, T., Kimura, T., Yamada, K. and Kimura, J. (1991) "Treatment of myelodysplastic syndromes with orally administered 1-β-D-arabinouranosylcytosine-5' stearylphosphate." Oncology 48, 451 455. Palomino, E., Kessle, D. and Horwitz, J. P. (1989) "A dihydropyridine carrier system for sustained delivery of 2',3' dideoxynucleosides to the brain." J. Med. Chem. 32, 22 625; Perkins, R. M., Barney, S. Wittrock, R., Clark, P. H., Levin, R. Lambert, D. M., Petteway, S. R., Serafinowska, H. T., Bailey, S. M., Jackson, S., Harnden, M. R. Ashton, R., Sutton, D., Harvey, J. J. and Brown, A. G. (1993) "Activity of BRL47923 and its oral prodrug, SB203657A against a rauscher murine leukemia virus infection in mice." Antiviral Res. 20 (Suppl. 1). 84; Piantadosi, C., Marasco, C. J., Jr., Norris-Natschke, S. L., Meyer, K. L., Gumus, F., Surles, J. R., lshaq, K. S., Kucera, L. S. Iyer, N., Wallen, C. A., Piantadosi, S. and Modest, E. J. (1991) "Synthesis and evaluation of novel ether lipid nucleoside conjugates for anti-HIV-1 activity." J. Med. Chem. 34, 1408 1414; Pompon, A., Lefebvre, I., Imbach, J. L., Kahn, S. and Farquhar, D. (1994). "Decomposition pathways of the mono- and bis(pivaloyloxymethyl) esters of azidothymidine-5'-monophosphate in cell extract and in tissue culture medium; an application of the 'on-line ISRP-cleaning HPLC technique." Antiviral Chem Chemother. 5, 91 98; Postemark, T. (1974) "Cyclic AMP and cyclic GMP." Annu. Rev. Pharmacol. 14, 23 33; Prisbe, E. J., Martin, J. C. M., McGhee, D. P. C., Barker, M. F., Smee, D. F. Duke, A. E., Matthews, T. R. and Verheyden, J. P. J. (1986) "Synthesis and antiherpes virus activity of phosphate an phosphonate derivatives of 9-[(1, 3-dihydroxy-2-propoxy)methyl]guanine." J. Med. Chem. 29, 671 675; Pucch, F., Gosselin, G., Lefebvre, I., Pompon, a., Aubertin, A. M. Dim, and Imbach, J. L. (1993) "Intracellular delivery of nucleoside monophosphate through a reductase-mediated activation process." Antiviral Res. 22, 155 174; Pugaeva, V. P., Klochkeva, S. I., Mashbits, F. D. and Eizengart, R. S. (1969). "Toxicological assessment and health standard ratings for ethylene sulfide in the industrial atmosphere." Gig. Trf. Prof. Zabol. 14, 47 48 (Chem. Abstr. 72, 212); Robins, R. K. (1984) "The potential of nucleotide analogs as inhibitors of Retro viruses and tumors." Pharm. Res. 11 18; Rosowsky, A., Kim. S. H., Ross and J. Wick, M. M. (1982) "Lipophilic 5'-(alkylphosphate) esters of 1-β-D-arabinofiiranosylcytosine and its N[4]-acyl and 2.2'-anhydro-3'-O-acyl derivatives as potential prodrugs." J. Med. Chem. 25, 171 178; Ross, W. (1961) "Increased sensitivity of the walker turnout towards aromatic nitrogen mustards carrying basic side chains following glucose pretreatment." Biochem. Pharm. 8, 235 240; Ryu, E. K., Ross, R. J. Matsushita, T., MacCoss, M., Hong, C. I. and West, C. R. (1982). "Phospholipid-nucleoside conjugates. 3. Synthesis and preliminary biological evaluation of 1-β-D-arabinofuranosylcytosine 5'diphosphate [−], 2-diacylglycerols." J. Med. Chem. 25, 1322 1329; Saffhill, R. and Hume, W. J. (1986) "The degradation of 5-iododeoxyuridine and 5-bromoethoxyuridine by serum from different sources and its consequences for the use of these compounds for incorporation into DNA." Chem. Biol. Interact. 57, 347 355; Saneyoshi, M., Morozumi, M., Kodama, K., Machida, J., Kuninaka, A. and Yoshino, H. (1980) "Synthetic nucleosides and nucleotides. XVI. Synthesis and biological evaluations of a series of 1-β-D-arabinofuranosylcytosine 5'-alky or arylphosphates." Chem Pharm. Bull. 28, 2915 2923; Sastry, J. K., Nehete, P. N., Khan, S., Nowak, B. J., Plunkett, W., Arlinghaus, R. B. and Farquhar, D. (1992) "Membrane-permeable dideoxyuridine 5'-monophosphate analogue inhibits human immunodeficiency virus infection." Mol. Pharmacol. 41, 441 445; Shaw, J. P., Jones, R. J. Arimilli, M. N., Louie, M. S., Lee, W. A. and Cundy, K. C. (1994) "Oral bioavailability of PMEA from PMEA prodrugs in male Sprague-Dawley rats." 9th Annual AAPS Meeting. San Diego, Calif. (Abstract). Shuto, S., Ueda, S., Imamura, S., Fukukawa, K. Matsuda, A. and Ueda, T. (1987) "A facile one-step synthesis of 5' phosphatidiylnucleosides by an enzymatic two-phase reaction." Tetrahedron Lett. 28, 199 202; Shuto, S. Itoh, H., Ueda, S., Imamura, S., Kukukawa, K., Tsujino, M., Matsuda, A. and Ueda, T. (1988) Pharm. Bull. 36, 209 217. An example of a useful phosphate prodrug group is the S-acyl-2-thioethyl group, also referred to as "SATE". Such compounds can be used in the methods described herein.

As used herein, Chikungunya virus is an RNA virus of the genus Alphavirus, and can also be treated using the compounds described herein.

As used herein, Dengue virus includes the Dengue virus group (Dengue virus, Dengue virus type 1, Dengue virus type 2, Dengue virus type 3, and Dengue virus type 4).

VI. Methods of Treatment

The compositions described herein can be used to treat patients infected with HIV-1 and HIV-2, Dengue virus, and Chikungunya virus, to prevent an infection by these viruses, or to eradicate an infection by these viruses.

When the treatment of HIV-1 or HIV-2 involves co-administration of the TREM-1 inhibitors described herein and nucleoside antiviral agents and/or non-thymidine nucleoside antiviral agents, the HIV-1 may already have developed one or more mutations, such as the M184V, K65R mutation or TAMS. In such a case, the second agent will ideally be selected to be active against HIV-1 that has these mutations. Methods for selecting appropriate antiretroviral therapy for patients with various mutations in their HIV-1 are known to those of skill in the art.

When the treatment involves the co-administration of an adenine, cytosine, thymidine, and guanine nucleoside antiviral agent, as well as the additional antiviral agent(s), ideally the administration is to a patient who has not yet developed any resistance to these antiviral agents or has been off therapy for at least three months. In that case, it may be possible to actually cure an infected patient if the therapy can treat substantially all of the virus, substantially everywhere it resides in the patient. However, even in the case of infection by a resistant virus, the combination therapy should be effective against all known resistant viral strains, because there is at least one agent capable of inhibiting such a virus in this combination therapy, and because the TREM-1 inhibitors do not function in the same manner as the conventional NRTI, NNRTI, protease inhibitors, entry inhibitors, integrase inhibitors, and the like, and thus remain effective against strains that have mutated following exposure to these agents.

The compounds can be used in different ways to treat or prevent HIV, and, in one embodiment, to cure an HIV infection. In one embodiment, a combination of a TREM-1 inhibitor as described herein, a macrophage depleting agent (e.g., clodronate-loaded or bis-phosphonate-loaded liposomes, gadolinium chloride (GdCl)), plus HAART therapy is used. The strategy involves reducing viral loads with traditional HAART and TREM-1 inhibitor therapy. Then, macrophages are systemically depleted (typically without discrimination for infected versus infected macrophages). HAART and TREM-1 inhibitor therapy would be maintained during macrophage depletion. Then, treatment with the macrophage depleting agent is withdrawn, while treatment with HAART and the TREM-1 inhibitor is maintained.

In one aspect of this embodiment, HAART is then withdrawn, while TREM-1 inhibitor therapy is maintained, optionally while monitoring viral rebound.

In another aspect of this embodiment, both HAART and TREM-1 inhibitor therapy are then withdrawn, optionally while monitoring viral rebound.

In another embodiment, viral loads are reduced with traditional HAART+TREM-1 inhibitors, specifically one or both of Tofacitinib and Jakafi, as described herein. Then, macrophages are systemically depleted (typically without discrimination for infected versus infected macrophages) with Boniva or Fosamax (both of these drugs are potent macrophage depleting agents). HAART+TREM-1 inhibitor therapy is maintained during macrophage depletion. Then, treatment with the macrophage depleting agent is withdrawn, while treatment with HAART and the TREM-1 inhibitor is maintained.

In one aspect of this embodiment, HAART is then withdrawn, while TREM-1 inhibitor therapy with one or both of Tofacitinib and Jakafi is maintained, optionally while monitoring viral rebound.

In another aspect of this embodiment, both HAART and TREM-1 inhibitor therapy with one or both of Tofacitinib and Jakafi are then withdrawn, optionally while monitoring viral rebound.

In another embodiment, a combination of a histone deacetylase inhibitor (HDAC inhibitor) or interleukin 7 (IL-7) and HAART and a TREM-1 inhibitor is used. One limitation associated with treating HIV is that while it is not fully understood how HIV-1 evades the immune response and establishes latency in resting cells, it is believed that a variety of signalling molecules and transcription factors appear to play a role, and thus offer potential targets for intervention. Thus, in this embodiment, IL-7 is used to confer reactivation of resting cells, effectively flushing HIV-1 out of hiding, and histone deacetylase (HDAC) inhibitors are used to confer reactivation by up regulation of pro-HIV genes, effectively coaxing virus out from previously resting cells. In this manner, latent HIV is eradicated. An example of a reactivation agent that could be used in this manner is panobinostate, which is described, for example, in Lewin, et al., "HIV cure and eradication: how will we get from the laboratory to effective clinical trials?" AIDS: 24 Apr. 2011. Representative HDAC inhibitors include Vorinostat, Romidepsin (trade name Istodax), Panobinostat (LBH589), Valproic acid (including Mg valproate and other salt forms), Belinostat (PXD101), Mocetinostat (MGCD0103), PCI-24781, Entinostat (MS-275), SB939, Resminostat (4SC-201), Givinostat (ITF2357), CUDC-101, AR-42, CHR-2845, CHR-3996, 4SC-202, sulforaphane, suberoylanilide hydroxamic acid (SAHA), BML-210, M344, CI-994; CI-994 (Tacedinaline); BML-210; M344; MGCD0103 (Mocetinostat); and Tubastatin A. Additional HDAC inhibitors are described in U.S. Pat. No. 7,399,787.

The strategy involves reducing viral loads with traditional HAART and TREM-1 inhibitor therapy. Then, the patient is treated with a reactivation agent (as defined in Lewin et al., supra), such as panobinostat.

In one aspect of this embodiment, both HAART and TREM-1 inhibitor therapy are maintained during reactivation, and in another aspect of this embodiment, HAART, but not TREM-1 inhibitor therapy, is maintained during reactivation.

Treatment with the reactivation agent is then withdrawn, while continuing treatment with HAART and one or more TREM-1 inhibitors, such as Tofacitinib and Jakafi as defined herein.

In one aspect of this embodiment, HAART is then withdrawn, while TREM-1 inhibitor therapy is maintained, optionally while monitoring viral rebound.

In another aspect of this embodiment, both HAART and TREM-1 inhibitor therapy are then withdrawn, optionally while monitoring viral rebound.

In another embodiment, the TREM-1 inhibitors are administered to a patient before, during, or after administration of a vaccine and/or an immunostimulant. The use of immunostimulants can provide an optimal antiretroviral regimen. The immunostimulatory treatments include, but are not limited to, therapies from two functional classes: 1) agents that target actively replicating cells and 2) agents activating latently infected cells.

In addition to the TREM-1 inhibitors and immunomodulatory agents, HAART can also be provided. The TREM-1 inhibitors, optionally with co-administered HAART, can suppress virus to undetectable or virtually undetectable levels. The addition of an immunomodulatory therapy that specifically targets viral reservoirs can, ideally, lead to a cure, or at least remove virus from one or more viral reservoirs.

Immunostimulants

The term "immunostimulant" is used herein to describe a substance which evokes, increases and/or prolongs an immune response to an antigen. While the present application distinguishes between an "antigen" and an "immunostimulant" it should be noted that this is merely for reasons of clarity and ease of description. It should be understood that the immunostimulant could have, and in many cases preferably has, antigenic potential itself.

Immunomodulatory agents modulate the immune system, and, as used herein, immunostimulants are also referred to as immunomodulatory agents, where it is understood that the desired modulation is to stimulate the immune system.

There are two main categories of immunostimulants, specific and non-specific. Specific immunostimulants provide antigenic specificity in immune response, such as vaccines or any antigen, and non-specific immunostimulants act irrespective of antigenic specificity to augment immune response of other antigen or stimulate components of the immune system without antigenic specificity, such as adjuvants and non-specific immunostimulators.

Examples of immunostimulants include levamisole, thalidomide, erythema nodosum leprosum, BCG, cytokines such as interleukins or interferons, including recombinant cytokines and interleukin 2 (aldeslukin), 3D-MPL, QS21, CpG ODN 7909, miltefosine, anti-PD-1 or PD-1 targeting drugs, and acid (DCA, a macrophage stimulator), imiquimod and resiquimod (which activate immune cells through the toll-like receptor 7), chlorooxygen compounds such as tetrachlorodecaoxide (TCDO), agonistic CD40 antibodies, soluble CD40L, 4-1BB:4-1BBL agonists, OX40 agonists, TLR agonists, moieties that deplete regulatory T cells, arabinitol-ceramide, glycerol-ceramide, 6-deoxy and 6-sulfono-myo-insitolceramide, iNKT agonists, TLR agonists.

WF 10 [Immunokine, Macrokine] is a 1:10 dilution of tetrachlorodecaoxide (TCDO) formulated for intravenous injection. WF 10 specifically targets macrophages, and modulates disease-related up-regulation of immune responses in vivo.

3D-MPL is an immunostimulant derived from the lipopolysaccharide (LPS) of the Gram-negative bacterium *Salmonella minnesota*. MPL has been deacylated and is lacking a phosphate group on the lipid A moiety. This chemical treatment dramatically reduces toxicity while preserving the immunostimulant properties (Ribi, 1986). Ribi Immunochemistry produces and supplies MPL to GSK-Biologicals.

QS21: is a natural saponin molecule extracted from the bark of the South American tree *Quillaja saponaria molina*. A purification technique developed to separate the individual saponins from the crude extracts of the bark, permitted the isolation of the particular saponin, QS21, which is a triterpene glycoside demonstrating stronger adjuvant activity and lower toxicity as compared with the parent component. QS21 has been shown to activate MHC class I restricted CTLs to several subunit Ags, as well as to stimulate Ag specific lymphocytic proliferation (Kensil, 1992). Aquila (formally Cambridge Biotech Corporation) produces and supplies QS21 to GSK-Biologicals.

CpG ODN 7909 is a synthetic single-stranded phosphorothioate oligodeoxy-nucleotide (ODN) of 24 bases length. Its base sequence, which is 5'-TCGTCGTTTTG-TCGTTTTGTCGTT-3', has been optimized for stimulation of the human immune system. CpG DNA or synthetic ODN containing CpG motifs are known to activate dendritic cells, monocytes and macrophages to secrete TH1-like cytokines and to induce TH1 T cell responses including the generation of cytolytic T cells, stimulate NK cells to secrete IFNg and increase their lytic activity, they also activate B cells to proliferate (Krieg A et al. 1995 Nature 374: 546, Chu R et al. 1997 J. Exp. Med. 186: 1623). CpG 7909 is not antisense to any known sequence of the human genome. CpG 7909 is a proprietary adjuvant developed by and produced on behalf of Coley Pharmaceutical Group, Inc., Mass., US.

iNKT Agonists

A subset of T cells known as iNKT (invariant natural killer T) cells are defined by their expression of a restricted TCR repertoire, consisting of a canonical V-alpha-14-J-alpha-18 or V-alpha-24-J-alpha-18-alpha chain in mice and humans respectively. iNKT cells recognize and become activated in response to self or foreign antigenic lipids presented by non-polymorphic CD1d molecules expressed on the surface of APCs. iNKT cells are activated in response to a variety of infections, and during inflammatory and autoimmune diseases. iNKT cells provide a means of linking and coordinating innate and adaptive immune responses, as their stimulation can induce the downstream activation of DCs, NK cells, B and T cells. It has been demonstrated in vitro that iNKT cells stimulate B cell proliferation and antibody production.

NKT cells can be activated by alpha-galactosyl-ceramide (alpha-GalCer) or its synthetic analog KRN 7000 (U.S. 2003/0157135). Alpha-GalCer can stimulate NK activity and cytokine production by NKT cells (U.S. 2003/0157135). Alpha-GalCer and related glycosylceramides not only function as antigens, but can also be used as soluble adjuvants capable of enhancing and/or extending the duration of the protective immune responses induced by other antigens.

Thus, in some embodiments of the present invention the immunostimulant may be an iNKT cell agonist. The agonist may be an exogenous or endogenous agonist. It may be a glycosidic agonist (such as alpha-galactasylceramide) or a non-glycosidic agonist (such as threitolceramide).

Immunostimulatory Lipids or Glycolipids

In some embodiments, the immunostimulant may be a lipid or a glycolipid. Glycolipids presented by CD1 can be grouped into different classes including for example diacylglycerolipids, sphingolipids, mycolates and phosphomycoketides (Zajonc and Krenenberg, Current Opinion in Structural Biology, 2007, 17:521-529). Microbial antigens from pathogenic mycobacteria, such as glucose monomycolates (GMM), mannosyl phosphomycoketides and phosphatidylinositol mannosides are known to be potent ligands for human T cells when presented by group I CD1 molecules (Zajonc an Kronenberg, supra). The immunostimulant can be a glycosylceramide, for example alpha-galactosylceramide (KRN 7000, US2003/0157135) or an analogue thereof, such as for example threitolceramide (IMM47) or other non-glycosidic iNKT cell agonists (as described in Silk et al. Cutting Edge J. Immunol, 2008). Further analogues which may be used in accordance with the invention and methods of producing such analogues are disclosed in WO2007/050668, which is incorporated herein by reference.

TLR Agonists

Intracellular TLRs such as TLRs 3, 7, 8 and 9 recognize nucleic acids. As such, synthetic oligodeoxynucleotides (ODN) such as the TLR9 agonist CpG have previously been used as immunostimulants. These TLR immunostimulants operate by a different mechanism than that employed by lipids such as alphaGalCer. These immunostimulants directly activate the cell that they are taken up by, culminating in, for example, the secretion of cytokines and chemokines that result in the further stimulation of immune responses.

The TLR expression pattern is specific for each cell type (Chiron et al, 2009). TLR expression in human B cells is characterized by high expression of TLR 1, 6, 7, 9 and 10, with the expression pattern varying during B-cell differentiation.

Soluble CpG ODNs are rapidly internalized by immune cells and interact with TLR9 that is present in endocytic vesicles. Cellular activation by most members of the TLR family (including TLR9) involves a signaling cascade that proceeds through myeloid differentiation primary response gene 88 (MYD88), interleukin-1 (IL-1), receptor-activated kinase (IRAK) and tumor-necrosis factor receptor (TNFR)-associated factor 6 (TRAF6), and culminates in the activation of several transcription factors, including nuclear factor-kappaB (NF-kappaB), activating protein 1 (AP1), CCAAT-enhancer binding protein (CEBP) and cAMP-responsive element binding protein (CREB). These transcription factors directly upregulate cytokine/chemokine gene expression. B cells and plasmacytoid dendritic cells (pDCs) are the main human cell types that express TLR9 and respond directly to CpG stimulation. Activation of these cells by CpG DNA initiates an immunostimulatory cascade that culminates in the indirect maturation, differentiation and proliferation of natural killer (NK) cells, T cells and monocytes/macrophages. Together, these cells secrete cytokines and chemokines that create a pro-inflammatory (IL-1-α/β, IL-6, IL-18 and TNF) and $T_{H1}$-biased (interferon-gamma, IFN-gamma, and IL-12) immune milieu (Klinman, 2004, Nature Reviews, 4:249).

Thus, in some embodiments the immunostimulant is a TRL agonist. For example, it is an endosomal TLR agonist, in particular a nucleic acid, such as for example DNA, RNA (either double or single stranded). The immunostimulant may, for example comprise a CpG oligodeoxynucleotide or a poly-U nucleic acid.

Saponins Saponins are taught in: Lacaille-Dubois, M and Wagner H. (1996. A review of the biological and pharmacological activities of saponins. Phytomedicine vol 2 pp 363-386). Saponins are steroid or triterpene glycosides widely distributed in the plant and marine animal kingdoms.

Saponins are known as adjuvants in vaccines for systemic administration. The adjuvant and haemolytic activity of individual saponins has been extensively studied in the art (Lacaille-Dubois and Wagner, supra). For example, Quil A (derived from the bark of the South American tree *Quillaja saponaria molina*), and fractions thereof, are described in U.S. Pat. No. 5,057,540 and "Saponins as vaccine adjuvants", Kensil, C. R., Crit Rev Ther Drug Carrier Syst, 1996, 12 (1-2):1-55; and EP 0 362 279 B1. Particulate structures, termed Immune Stimulating Complexes (ISCOMS), comprising Quil A or fractions thereof, have been used in the manufacture of vaccines (Morein, B., EP 0 109 942 B1). These structures have been reported to have adjuvant activity (EP 0 109 942 B1; WO 96/11711). The hemolytic saponins QS21 and QS17 (HPLC purified fractions of Quil A) have been described as potent systemic adjuvants, and the method of their production is disclosed in U.S. Pat. No. 5,057,540 and EP 0 362 279 B1. Also described in these references is the use of QS7 (a non-haemolytic fraction of Quil-A) which acts as a potent adjuvant for systemic vaccines. Use of QS21 is further described in Kensil et al. (1991. J. Immunology vol 146, 431-437). Combinations of QS21 and polysorbate or cyclodextrin are also known (WO 99/10008). Particulate adjuvant systems comprising fractions of QuilA, such as QS21 and QS7 are described in WO 96/33739 and WO 96/11711.

Other saponins which have been used in systemic vaccination studies include those derived from other plant species such as *Gypsophila* and *Saponaria* (Bomford et al., Vaccine, 10(9):572-577, 1992).

Cytokines

TH-1 type cytokines, e.g., IFN-gamma, TNF-α, IL-2, IL-12, IL-18, etc, tend to favor the induction of cell mediated immune responses to an administered antigen. In contrast, high levels of Th2-type cytokines (e.g., IL4, IL-5, IL-6 and IL-10) tend to favor the induction of humoral immune responses. Interleukin-18 (IL-18), also known as interferon-gamma (IFNg) inducing factor, has been described as an pleotropic cytokine with immunomodulatory effects that stimulates patient's own immune system against disease. IL-18 has several bioactivities, including the ability to promote the differentiation of naive CD4 T cells into Th1 cells, to stimulate natural killer (NK) cells, natural killer T (NKT) cells, and to induce the proliferation of activated T cells, predominantly cytotoxic T cells (CD8+phenotype) to secrete gamma interferon (IFN-gamma) (Okamura H. et al. 1998, Adv. Immunol. 70: 281-312). IL-18 also mediates Fas-induced tumor death, promotes the production of IL-1-α/β and GMCSF, and has anti-angiogenic activity. IFN-α 2a, including pegylated versions thereof (Pegasys), can also be used. Recombinant human Interleukin-7 (r-hIL-7/CYT107) can also be used.

Vaccines

As used herein, "vaccine" includes all prophylactic and therapeutic vaccines.

A vaccine includes an antigen or immunogenic derivative, and an adjuvant. As used herein, the vaccines can be any vaccine that inhibits any of the viruses described herein, including anti-HIV vaccines which inhibit HIV through any mechanism.

Where the vaccine is an anti-HIV vaccine, it ideally inhibits or stops the HIV virion replication cycle at any one of the following phases of the HIV virion cycle:

Phase I. Free State
Phase II. Attachment
Phase III. Penetration
Phase IV. Uncoating
Phase V. Replication
Phase VI. Assembling
Phase VII. Releasing While many antiviral vaccines use live viruses, with respect to HIV vaccines, it is not advisable to use live viruses, due to the risk of infection. However, it is known that deletion of the HIV nef gene attenuates the virus. Desrosiers and his associates have demonstrated that vaccination of macaques with nef-deleted SIV protected wild-type SIV challenge (Daniels, M. D. et al. Science 258:1938 (1992); Desrosiers, R. C., et al. Proc. Natl. Acad. Sci. USA 86:6353 (1989)) and others have demonstrated that nef gene is dispensable for SIV and HIV replication (Daniels, M. D. et al. Science 258:1938 (1992); Gibbs, J. S., et al. AIDS Res. and Human Retroviruses 10:343 (1994); Igarashi, T., et al. J. Gen. Virol. 78:985 (1997); Kestler III, H. W., et al. Cell 65:651 (1991)). Furthermore, deletion of nef gene renders the virus to be non-pathogenic in the normally susceptible host (Daniels, M. D. et al. Science 258:1938 (1992)).

In terms of antigens, subunit vaccines can be used (Cooney E L, et al., Proc Natl Acad Sci USA 1993; 90; 1882-86; McElrath M J, et al. J Infect Dis. 169: 41-47 (1994); Graham B S, et al. J Infect Dis 166: 244-52 (1992); and Graham B S, et al. J Infect Dis 167: 533-37 (1993)). HIV-derived antigens include HIV-1 antigen gp120, tat, nef, reverse transcriptase, gag, gp120 and gp160, and various targets in pol One examples of an HIV vaccine is the DermaVir therapeutic HIV vaccine, currently in Phase II clinical studies.

The vaccines of the present invention may additionally contain suitable diluents, adjuvants and/or carriers. In some embodiments, the vaccines contain an adjuvant which can enhance the immunogenicity of the vaccine in vivo. The adjuvant may be selected from many known adjuvants in the art, including the lipid-A portion of gram negative bacteria endotoxin, trehalose dimycolate of mycobacteria, the phospholipid lysolecithin, dimethyldictadecyl ammonium bromide (DDA), certain linear polyoxypropylene-polyoxyethylene (POP-POE) block polymers, aluminum hydroxide, and liposomes. The vaccines may also include cytokines that are known to enhance the immune response including GM-CSF, IL-2, IL-12, TNF-α and IFNγ.

The dose of the vaccine may vary according to factors such as the disease state, age, sex, and weight of the individual, and the ability of antibody to elicit a desired response in the individual. Dosage regime may be adjusted to provide the optimum therapeutic response. For example, several divided doses may be administered daily or the dose may be proportionally reduced as indicated by the exigencies of the therapeutic situation. The dose of the vaccine may also be varied to provide optimum preventative dose response depending upon the circumstances.

The vaccines may be administered in a convenient manner such as by injection (subcutaneous, intravenous, intramuscular, etc.), oral administration, inhalation, transdermal administration (such as topical cream or ointment, etc.), or suppository applications.

Recombinant Retrovirus

The recombinant retrovirus of the present invention can be any retrovirus, including HIV-1, HIV-2, SIV, HTLV-1. Preferably the retrovirus is a human immunodeficiency virus selected from HIV-1 and HIV-2, more preferably, the retrovirus is HIV-1.

The vaccine can be an essentially non-cytolytic retrovirus, wherein the term "essentially non-cytolytic" means that the retrovirus does not significantly damage or kill the cells it infects. In one embodiment, the natural signal sequence of HIV-1 envelope glycoprotein gp120 (NSS) is modified to be essentially non-cytolytic, or is replaced with an essentially non-cytolytic signal sequence.

In one embodiment, the present invention provides an essentially non-cytolytic recombinant HIV-1 capable of highly efficient replication wherein the NSS of the virus' envelope glycoprotein is modified sufficiently to prevent cell damage by the virus, preferably by eliminating positively charged amino acids, even more preferably, such elimination or modification resulting in no more than one (1) and preferably zero (0) positively charged amino acids. The positively charged amino acids which may be modified or replaced include lysine and arginine.

In another embodiment, replacement of the natural signal sequence results in a more efficient replication of HIV. Accordingly the present invention provides an essentially non-cytolytic recombinant HIV-1 capable of highly efficient replication wherein the NSS of the virus' envelope glycoprotein is replaced with an essentially non-cytolytic and more efficient signal sequence. In a preferred embodiment, replacement of the NSS of the envelope glycoprotein of HIV-1 with either the mellitin or IL-3 signal sequence decreases the cytotoxicity of the retrovirus. As such, the present invention includes within its scope replacement of NSS with any signal sequence which renders the retrovirus essentially non-cytolytic. The inventors have also shown that replacement of the NSS with mellitin or IL-3 signal sequences results in a greater level of production and secretion of gp120, in addition to the reduced cytotoxicity. The inventors have also shown that replacement of the NSS results in partial deletion the vpu gene. Studies have shown the vpu gene can be completely deleted without any measurable impact on the virus' ability to replicate (James et al. AIDS Res. Human Retrovirus 10:343-350, 1994).

In another embodiment, the retrovirus is rendered avirulent. In a preferred embodiment, the virus is rendered avirulent by deleting the nef gene. Accordingly, the present invention provides an avirulent, essentially non-cytolytic retrovirus which contains a sufficient deletion of the nef gene to render the virus non-pathogenic and wherein the virus' envelope glycoprotein gp120 coding sequence is replaced with a more efficient signal sequence. As used herein, "sufficient deletion" means deletion of enough of the sequence to prevent transcription and thereby production of the nef protein product.

In a further embodiment, the retrovirus is rendered avirulent, essentially non-cytolytic, and contains a sufficient deletion of the nef gene and the vpu gene to render the virus non-pathogenic.

Recombinant retroviruses be prepared using techniques known in the art. In one embodiment, the retrovirus can be introduced in a host cell under conditions suitable for the replication and expression of the retrovirus in the host.

The essentially non-cytolytic and avirulent retroviruses can typically be produced in large quantities and in a form that is non-pathogenic to the patient. The viruses can be used, in combination with the JAK inhibitors and, optionally, with HAART, for preventing or treating a retroviral infection. In this use, an effective amount of a killed recombinant essentially non-cytolytic avirulent retrovirus is administered to a patient in need of treatment or prophylaxis of a retroviral infection. The term "effective amount" as used herein means an amount effective and at dosages and for periods of time necessary to achieve the desired result.

In one embodiment, the natural signal sequence of the virus' envelope glycoprotein, such as gp120, is modified to provide an essentially non-cytolytic signal sequence, and/or the virus is rendered avirulent by deleting the nef gene. In one aspect of this embodiment, the modification to provide a non-cytolytic NSS results in no more than one positively charged amino acid in the NSS sequence, more preferably zero positively charged amino acids.

In another aspect of this embodiment, the natural signal sequence of the virus' envelope glycoprotein, preferably gp120, is replaced with an essentially non-cytolytic signal sequence, and, optionally, the virus is rendered avirulent by deleting the nef gene.

In another aspect of this embodiment, where the NSS is replaced, the non-cytolytic signal sequence is selected from the group consisting of the mellitin sequence and the IL-3 signal sequence.

Chimaeric Antigens The vaccines can comprise chimaeric antigens, for example, a chimaeric influenza-HIV vaccine. In one embodiment, the vaccine comprises the A-antigenic loop of influenza haemagglutinin (HA-A), modified to resemble the principle neutralizing determinant (PND) of HIV envelope glycoprotein gp120. The Chimaeric antigens can be presented as killed or attenuated virus.

Vaccine Production

To produce a vaccine, the antigen is typically combined with a pharmaceutically acceptable carrier, and, typically, an adjuvant, to make a composition comprising a vaccine. This vaccine composition is optionally combined with an immunostimulant and administered to a patient in need of treatment or prevention of a viral infection.

In one embodiment, the vaccine includes antigens selected for more than one virus, particularly where co-infection rates are known to be high. One example is HIV and HBV or HCV, or HIV and influenza.

A variety of adjuvants known to one of ordinary skill in the art may be administered in conjunction with the protein in the vaccine composition. Such adjuvants include, but are not limited to the following: polymers, co-polymers such as polyoxyethylene-polyoxypropylene copolymers, including block co-polymers; polymer P1005; monotide ISA72; Freund's complete adjuvant (for animals); Freund's incomplete adjuvant; sorbitan monooleate; squalene; CRL-8300 adjuvant; alum; QS 21, muramyl dipeptide; trehalose; bacterial extracts, including mycobacterial extracts; detoxified endotoxins; membrane lipids; or combinations thereof.

The vaccine formulations can be presented in unit dosage form, and can be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers. Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets commonly used by one of ordinary skill in the art.

Preferred unit dosage formulations are those containing a dose or unit, or an appropriate fraction thereof, of the administered ingredient. It should be understood that in addition to the ingredients, particularly mentioned above, the formulations of the present invention may include other agents commonly used by one of ordinary skill in the art.

The vaccine may be administered through different routes, such as oral, including buccal and sublingual, rectal, parenteral, aerosol, nasal, intramuscular, subcutaneous, intradermal, and topical. The vaccine of the present invention may be administered in different forms, including but not limited to solutions, emulsions and suspensions, microspheres, particles, microparticles, nanoparticles, and liposomes. It is expected that from about 1 to 5 dosages may be required per immunization regimen. Initial injections may range from about 1 mg to 1 gram, with a preferred range of about 10 mg to 800 mg, and a more preferred range of from approximately 25 mg to 500 mg. Booster injections may range from 1 mg to 1 gram, with a preferred range of approximately 10 mg to 750 mg, and a more preferred range of about 50 mg to 500 mg.

The volume of administration will vary depending on the route of administration. Intramuscular injections may range from about 0.1 ml to 1.0 ml.

The vaccines can be administered before, during or after an infection. An infected individual can receive a vaccine directed to the virus infecting the individual, even though the levels are reduced via treatment with the TREM-1 inhibitors and/or HAART, stimulating the immune system to fight the virus that remains in the individual.

The vaccine may be stored at temperatures of from about 4 C to −100 C. The vaccine may also be stored in a lyophilized state at different temperatures including room temperature. The vaccine may be sterilized through conventional means known to one of ordinary skill in the art. Such means include, but are not limited to filtration, radiation and heat. The vaccine of the present invention may also be combined with bacteriostatic agents, such as thimerosal, to inhibit bacterial growth.

Those of skill in the art can effectively follow the administration of these therapies, and the development of side effects and/or resistant viral strains, without undue experimentation.

The present invention will be better understood with reference to the following non-limiting examples.

Example 1: Representative Screening Procedures for Determining the Effectiveness of a Potential TREM-1 Inhibitor Compounds can be screened for their ability to inhibit TREM-1, for example, using the screening methods disclosed in EP 2555789 A1. These methods can be used for antibodies, peptides, aptamers, small molecules, and the like. The methods involve measuring, or qualitatively or quantitatively detecting, the competition of binding of a candidate compound to the receptor with a labeled competitor (e.g., an antagonist).

In one particular embodiment, the screening method involves:
a) providing a plurality of cells expressing the TREM-1 ligand protein and cells expressing the TREM-1 protein:
b) incubating these cells with a candidate compound (including proteins, peptides, antibodies, aptamers, and small molecules);
c) determining whether the candidate compound binds to the TREM-1 ligand protein; and
d) selecting those candidate compounds that inhibit the TREM-1/TREM-1 ligand interaction.

An additional screening method involving reactive oxygen species is described in EP 2555789A1. Neutrophils produce reactive oxygen species ("ROS") in presence of LPS (lipopolysaccharides), anti-TREM-1 mAbs (monoclonal antibodies), or platelets (that constitutively express the TREM-1 ligand) with a synergistic effect of these different inducers that is mediated by neutrophils membrane-bound TREM-1.

ROS production can be quantified using a fluoregenic substrate (DCFDA: 5-(and -6)-carboxy-2',7'-dichlorodihydro fluorescein diacetate (carboxy-H2DCFDA) *mixed isomers*). For example, $2.5 \times 10^5$ isolated human neutrophils can be incubated 2 hours at 37° C./5% $CO_2$ with 5 M of DCFDA, in presence of 20 g/mL anti-TREM-1 mAb with or without 100 ng/mL LPS. ROS production by TREM-1 activation and its modulations by polypeptides can then be quantified by flow cytometry. If the studied peptide inhibits TREM-1, mean fluorescence intensity (MFI) decrease as compared to conditions without TREM-1 mAb. This rapid assay allows one to quickly determine which are the most active peptides at inhibiting TREM-1. In general, such screening methods involve providing appropriate cells which express the TREM-1 protein, or its orthologs or derivatives thereof, on their surface.

In one aspect of this embodiment, a nucleic acid encoding the TREM-1 protein can be used to transfect cells to express the TREM-1 protein. Such a transfection can be achieved by methods well known in the art.

Example 2: Comparison of TREM-1 Inhibitors to Conventional Antiretroviral Therapy Current first line highly active antiretroviral therapy (HAART) for the treatment of human immunodeficiency virus (HIV-1) infections combines two nucleoside reverse transcriptase inhibitors (NRTI) together with either a protease inhibitor (PI) or non-nucleoside reverse transcriptase inhibitor (NNRTI). These drug combinations have markedly decreased mortality and morbidity from HIV-1 infections in the developed world.

Existing therapies cannot eradicate HIV-1 infection because of the compartmentalization of the virus and its latent properties. Therefore, chronic therapy remains the standard of care for the foreseeable future. Although HAART regimens are selected in part to minimize cross resistance, and thereby delay the emergence of resistant viruses, all regimens eventually fail, due primarily to lack of adherence to strict regimens, delayed toxicities and/or the emergence of drug-resistant HIV-1 strains, making it a major imperative to develop regimens that delay, prevent or attenuate the onset of resistance for second line treatments for infected individuals who have already demonstrated mutations. The occurrence of common resistance mutations, including thymidine analog mutations (TAM), K65R and M184V, need to be a continued focus in the rational design of HIV-1 NRTI drug development.

The objectives of this study were to evaluate TREM-1 inhibitors that do not appear to function in the same manner as NRTI, NNRTI, protease inhibitors, entry inhibitors, integrase inhibitors, and the like. In this example, TREM-1 inhibitors were combined with JAK inhibitors, such as Jakafi (Incyte) and Tofacitinib (Pfizer).

PBM Cell and Mφ Protocol for Antiviral Potency

Macrophages can be isolated as follows: Monocytes can be isolated from buffy coats of HIV-1 negative, HBV/HCV-negative donors with density gradient centrifugation coupled with enrichment for CD14+ monocytes with Rosette Sep antibody cocktail (Stem Cell Technologies, Vancouver, British Columbia). Cells can be seeded at a concentration of $1.0 \times 10^6$ cells/well for 1 hr at 37° C. and 5% $CO_2$ to confer plastic adherence prior to repeated washes with 1×PBS. Macrophages can be maintained in medium containing 100 U/ml macrophage colony-stimulating factor (m-CSF, R&D Systems, Minneapolis, MN), supplemented with 20% fetal calf serum (Atlanta Biologicals, Lawrenceville, GA) and 1% penicillin/streptomyocin (Invitrogen, Carlsbad, CA) for 7 days (37° C., 5% $CO_2$) prior to testing.

Macrophage infections: Macrophages can be cultured as described above for 7 days. For acute infection, macrophages can be serum starved for 8 hrs prior to infection and cultured for 2 hr in medium containing various concentrations of AZT (positive control) or Tofacitinib or Jakafi for 2 hr prior to removal of drug-containing medium and 4 hr infection with HIV-1$_{BaL}$ at 0.1 MOI in the absence of drug. Four hr after infection, virus can be removed and drug-containing medium returned to the cultures. Supernatants can be collected on day 7 post-infection and HIV-1 p24 can be quantified via ELISA (Zeptometrix Corporation, Buffalo, NY). $EC_{50}$ analysis can be performed using CalcuSyn software (BioSoft Corporation, Cambridge, UK).

Figure 1:
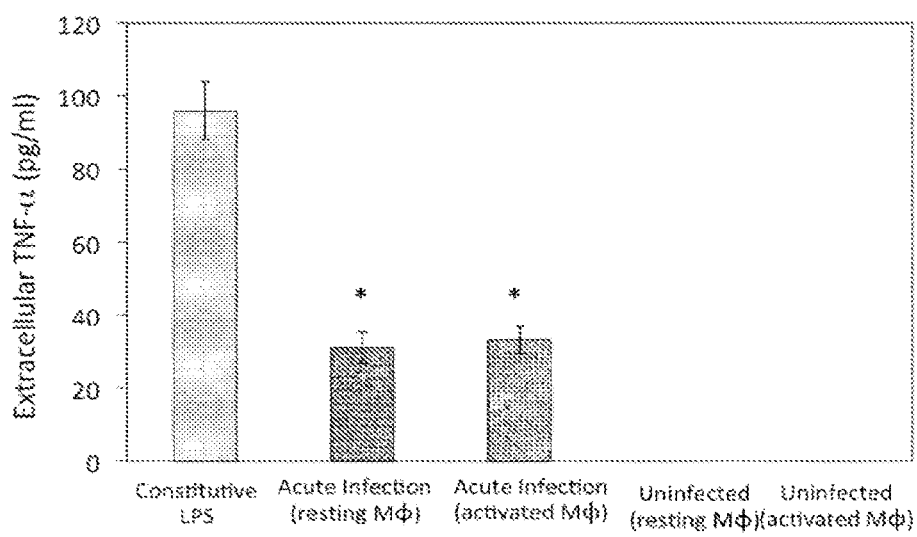
FIG. 1 is a chart showing extracellular tissue necrosis factor-alpha (TNF-α) production in acutely infected resting or activated macrophages or constitutively exposed to lipopolysaccharide (LPS), shown in terms of pg/ml extracellular TNF-α.

FIG. 1 shows that extracellular TNF-α production is significantly increased in HIV-infected primary human macrophages. Primary human macrophages were exposed to 5 µg/ml LPS (positive control) or acute HIV-1 infection in resting or activated macrophages (absence or presence of constitutive 5 ng/ml GM-CSF). Acute HIV-1 infection significantly increases TNF-α production in both resting and activated macrophages (blue and brown bars) versus uninfected controls (right panels) (p<0.01, student's t-test). All time points were assessed at 48 hours post virus or LPS exposure. Data are mean and standard deviation from three donors performed in replicates. * indicates significant increase versus uninfected controls.

Human PBM cells can be isolated as follows: Lymphocytes can be isolated from buffy coats derived from healthy donors. Activated lymphocytes can be maintained for 72 hr in medium supplemented with 6 µg/ml phytohemagglutinin (PHA) (Cape Cod associates, East Falmouth, MA). Media can be comprised of RPMI media supplemented with 20% fetal calf serum, 1% penicillin/streptomyocin and 2% L-glutamine (Sigma Aldrich, San Jose, CA).

Human PBM cell infections: Testing can be performed in duplicate with at least 3 independent assays. Cells can be incubated in RPMI medium (HyClone, Logan, Utah) containing HR-IL2 (26.5 units/ml) and 20% fetal calf serum. Infections can be performed by adding HIV-1$_{LAI}$ followed by a further incubation at 37° C., 5% C02, 1 hr prior to addition of drugs. Assays can be performed in 24 well plates (BD Biosciences, Franklin Lakes, New Jersey). One ml of supernatant can be collected after 5 days in culture and then centrifuged at 12,000 rpm for 2 hr at 4° C. in a Jouan Br43i (Thermo Electron Corp., Marietta, OH). The product of the RT assay can be quantified using a Packard harvester and direct beta counter and the data can be analyzed as previously described (Schinazi et al., 1990).

Cytotoxicity Assay

The toxicity of the compounds was assessed in Vero, human PBM, CEM (human lymphoblastoid), as described previously (see Schinazi R. F., Sommadossi J.-P., Saalmann V., Cannon D. L., Xie M.-Y., Hart G. C., Smith G. A. & Hahn E. F. Antimicrob. Agents Chemother. 1990, 34, 1061-67), and also in MØ cells. Cycloheximide was included as positive cytotoxic control, and untreated cells exposed to cell culture medium were included as negative controls.

The cytotoxicity $IC_{50}$ was obtained from the concentration-response curve using the median effective method described previously (see Chou T.-C. & Talalay P. Adv. Enzyme Regul. 1984, 22, 27-55; Belen'kii M. S. & Schinazi R. F. Antiviral Res. 1994, 25, 1-11).

The potency and toxicity of JAK inhibitors Tofacitinib and Jakafi versus FDA approved controls AZT and 3TC was evaluated in acutely infected activated MØ, as well as in PBM cells. The $EC_{50}$ data (µM) is shown in FIG. 2. Also shown in FIG. 2 are the $IC_{50}$ values (µM) for these compounds in PBM, MØ cells, CEM cells, and Vero cells.

Primary human macrophages were exposed to 5 µg/ml LPS (positive control) or acute HIV-1 infection in resting or activated macrophages (absence or presence of constitutive 5 ng/ml GM-CSF). Acute HIV-1 infection significantly increases TNF-α production in both resting and activated macrophages (blue and brown bars) versus uninfected controls (right panels) (p<0.01, student's t-test). All time points were assessed at 48 hours post virus or LPS exposure. Data are mean and standard deviation from three donors performed in replicates.

The data show a very large therapeutic window (ratio of toxicity/potency), and that the JAK inhibitor compounds have substantially the same $EC_{50}$ and substantially lower $IC_{50}$ values than AZT.

Cell proliferation was evaluated in activated PBM cells incubated for 5 days with various concentrations of Tofacitinib and Jakafi, with cycloheximide as a positive control, and a "cells plus media" control used as well. The data is shown in FIG. 2, in terms of total cell number ($10^6$ cells) versus µM drug in medium. The data shows that Tofacitinib and Jakafi do not affect total cell proliferation at antiviral concentrations.

Cell viability was evaluated in activated PBM cells incubated for 5 days with various concentrations of Tofacitinib and Jakafi, with cycloheximide as a positive control, and a "cells plus media" control used as well.

Figure 3A:
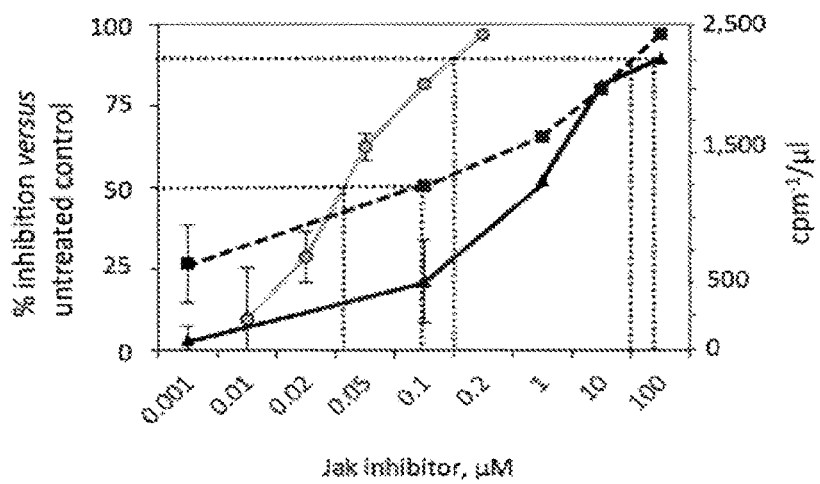
FIGS. 3A and 3B show the antiviral potency for co-administration of ruxolitinib and tofacitinib in primary human lymphocytes (FIG. 3A) and macrophages (FIG. 3B, in terms of cell viability (%) versus μM drug in medium.
Figure 3B:
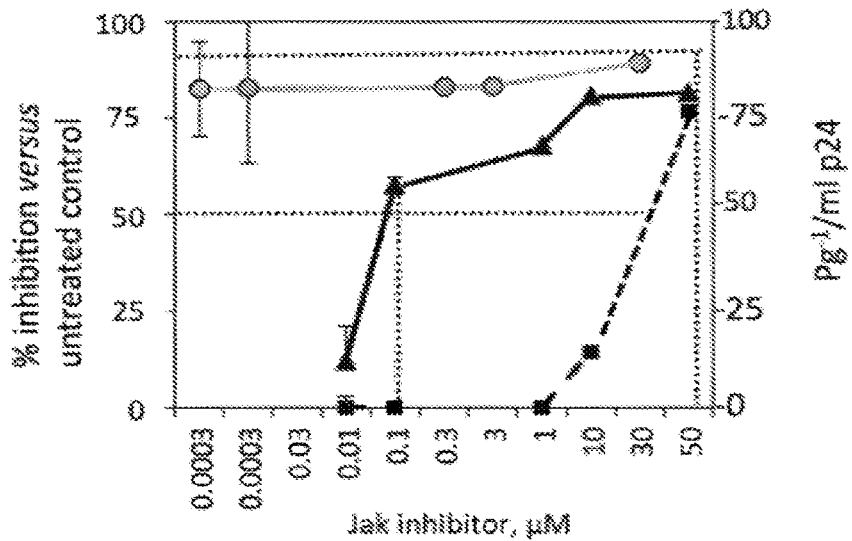

FIGS. 3A and 3B show the antiviral potency for co-administration of ruxolitinib and tofacitinib in primary human lymphocytes (FIG. 3A) and macrophages (FIG. 3B, in terms of cell viability (%) versus µM drug in medium.

Co-treatment of ruxolitinib and tofacitinib (dotted line) at a ratio of 1:4 (lymphocytes, FIG. 3A) or 1:1 (macrophages, FIG. 3B) demonstrated synergistic antiviral potency as calculated by CalcuSyn (Biosoft, Inc., Cambridge, Great Britain). Triangles, tofacitinib alone; squares, Ruxolitinib alone; dotted line with circles, ruxolitinib+tofacitinib. Data are mean and standard deviations for at least three independent experiments conducted with at least 4 pooled donors, and duplicates within each experiment. Numerical values on left Y axes represent percent inhibition versus no drug control. Numerical values on right Y axes represent $cpm^{-1}/\mu l$ (RT values) or $pg^{-1}/ml$ p24 for PBM cells and macrophages, respectively.

The data also show that Tofacitinib and Jakafi do not affect total cell viability at antiviral concentrations. The effect of Jak inhibitors on the proliferation and viability of PHA or PHA+IL-2 stimulated primary human lymphocytes is shown in FIGS. 4A-D. For PHA stimulated lymphocytes, viability and proliferation were not significantly different than that of cells exposed to media alone for all concentrations of either ruxolitinib or tofacitinib (FIG. 4A, FIG. 4C). For PHA+IL-2 stimulated lymphocytes, viability was not significantly different than that of cells exposed to media alone for all concentrations of either ruxolitinib (dotted line with squares) or tofacitinib (light gray line with diamonds) (FIG. 4B), however proliferation was significantly inhibited by 1 µM of ruxolitinib or tofacitinib (FIG. 4D). For all experiments, cells were incubated with media alone or drug-containing medium for 5 days prior to assessment of cell count and viability. The positive control of cycloheximide (solid line, diamonds) was toxic in a dose dependent manner as expected. Data are mean and standard deviations for at least three independent experiments conducted with at least four pooled donors, and duplicates within each experiment. Dotted bar represents mean cell count or viability for cells maintained in drug-free medium.

The TREM-1 peptide significantly reduces HIV-induced monocyte activation. Primary human monocytes were exposed to replication competent M-R5 HIV-1 BaL for 5 days prior to quantification of HIV-induced activation ($CD14^+/CD16^+$ monocytes; tandem two color FACS). Data is shown in FIGS. 5A and 5B. FIG. 5A shows that HIV infection is associated with an increase in the number of activated monocytes. FIG. 5B shows that following administration of TREM-1 peptide, the number of activated monocytes was lower.

Assay represents three independent donors conducted with duplicates. Data are mean and standard deviations, * indicates significant reduction versus BaL infected, no drug control (one-way ANOVA).

TREM-1 peptide significantly reduced HIV-induced activation in primary human macrophages without altering CD4 expression. Primary human macrophages were treated with replication competent M-R5 HIV-1 BaL for 5 days in the presence or absence of various concentrations of TREM-1 peptide. TREM-1 peptide significantly reduces HIV-1 induced activation markers HLA-DR (FIG. 6A), CCR5 (FIG. 6B), and CD163 (FIG. 6C); * one way ANOVA). TREM-1 peptide does not reduce CD4 expression (FIG. 6D), demonstrating that CD4 receptor expression-mediated innate and adaptive immunity is not altered. HIV-1 BaL significantly increases activation markers CD163, CCR5, and CD163 versus no virus control (**; one-way ANOVA). Data are mean and standard deviation for three independent donors conducted in duplicates.

These assays can be repeated with the TREM-1 inhibitors described herein.

Conclusion

In conclusion, Tofacitinib and Jakafi are potent, submicromolar inhibitors of HIV-1 replication in both PBM cells and MØ cells. The compounds do not affect viability or proliferation for PBM cells and MØ cells, or total cell number, up to around 10 µM (2-3 logs above $EC_{50}$). The therapeutic window (ratio of toxicity:potency) is wide for both cell types (24→100).

Example 3: Mitochondrial Toxicity Assays in HepG2 Cells i) Effect of the TREM-1 Inhibitors described herein on Cell Growth and Lactic Acid Production: The effect on the growth of HepG2 cells can be determined by incubating cells in the presence of 0 µM, 0.1 µM, 1 µM, 10 µM and 100 µM drug. Cells ($5 \times 10^4$ per well) were plated into 12-well cell culture clusters in minimum essential medium with nonessential amino acids supplemented with 10% fetal bovine serum, 1% sodium pyruvate, and 1% penicillin/streptomycin and incubated for 4 days at 37° C. At the end of the incubation period the cell number was determined using a hemocytometer. Also taught by Pan-Zhou X-R, Cui L, Zhou X-J, Sommadossi J-P, Darley-Usmer V M. "Differential effects of antiretroviral nucleoside analogs on mitochondrial function in HepG2 cells" Antimicrob. Agents Chemother. 2000; 44: 496-503. To measure the effects of the compounds on lactic acid production, HepG2 cells from a stock culture can be diluted and plated in 12-well culture plates at $2.5 \times 10^4$ cells per well. Various concentrations (0 µM, 0.1 µM, 1 µM, 10 µM and 100 µM) of the compounds can be added, and the cultures incubated at 37° C. in a humidified 5% $CO_2$ atmosphere for 4 days. At day 4 the number of cells in each well can be determined and the culture medium collected. The culture medium was filtered, and the lactic acid content in the medium determined using a colorimetric lactic acid assay (Sigma-Aldrich). Since lactic acid product can be considered a marker for impaired mitochondrial function, elevated levels of lactic acid production detected in cells grown in the presence of the compounds would indicate a drug-induced cytotoxic effect.

ii) Effect on the compounds on Mitochondrial DNA Synthesis: a real-time PCR assay to accurately quantify mitochondrial DNA content has been developed (see Stuyver L J, Lostia S, Adams M, Mathew J S, Pai B S, Grier J, Tharnish P M, Choi Y, Chong Y, Choo H, Chu C K, Otto M J, Schinazi R F. Antiviral activities and cellular toxicities of modified 2',3'-dideoxy-2',3'-didehydrocytidine analogs. Antimicrob. Agents Chemother. 2002; 46: 3854-60). This assay can be used to determine the effect of the compounds on mitochondrial DNA content. In this assay, low-passage-number HepG2 cells are seeded at 5,000 cells/well in collagen-coated 96-well plates. The compounds are added to the medium to obtain final concentrations of 0 µM, 0.1 µM, 10 µM and 100 µM. On culture day 7, cellular nucleic acids are prepared by using commercially available columns (RNeasy 96 kit; Qiagen). These kits co-purify RNA and DNA, and hence, total nucleic acids were eluted from the columns. The mitochondrial cytochrome c oxidase subunit II (COXII) gene and the β-actin or rRNA gene were amplified from 5 µl of the eluted nucleic acids using a multiplex Q-PCR protocol with suitable primers and probes for both target and reference amplifications. For COXII the following sense, probe and antisense primers are used, respectively: 5'-TGCCCGCCATCATCCTA-3' (SEQ ID NO. 8), 5'-tetrachloro-6-carboxyfluorescein-TCCTCATCGCCCT-CCCATCCC-TAMRA-3' (SEQ ID NO. 9) and 5'-CGT-CTGTTATGTAAAGGATGCGT-3' (SEQ ID NO. 10). For exon 3 of the β-actin gene (GenBank accession number E01094) the sense, probe, and antisense primers are 5'-GCGCGGCTACAGCTTCA-3' (SEQ ID NO. 11), 5'-6-FAMCACCACGGCCGAGCGGGATAMRA-3' (SEQ ID NO. 12) and 5'-TCTCCTTAATGTCACGCACGAT-3' (SEQ ID NO. 13), respectively. The primers and probes for the rRNA gene are commercially available from Applied Biosystems. Since equal amplification efficiencies are obtained for all genes, the comparative CT method can be used to investigate potential inhibition of mitochondrial DNA synthesis. The comparative CT method uses arithmetic formulas in which the amount of target (COXII gene) is normalized to the amount of an endogenous reference (the β-actin or rRNA gene) and is relative to a calibrator (a control with no drug at day 7). The arithmetic formula for this approach is given by 2-ΔΔCT, where ΔΔCT is (CT for average target test sample–CT for target control)–(CT for average reference test–CT for reference control) (see Johnson M R, K Wang, J B Smith, M J Heslin, R B Diasio. Quantitation of dihydropyrimidine dehydrogenase expression by real-time reverse transcription polymerase chain reaction. Anal. Biochem. 2000; 278:175-184). A decrease in mitochondrial DNA content in cells grown in the presence of drug would indicate mitochondrial toxicity.

iii) Electron Microscopic Morphologic Evaluation: NRTI induced toxicity has been shown to cause morphological changes in mitochondria (e.g., loss of cristae, matrix dissolution and swelling, and lipid droplet formation) that can be observed with ultrastructural analysis using transmission electron microscopy (see Cui L, Schinazi R F, Gosselin G, Imbach J L. Chu C K, Rando R F, Revankar G R, Sommadossi J P. Effect of enantiomeric and racemic nucleoside analogs on mitochondrial functions in HepG2 cells. Biochem. Pharmacol. 1996, 52, 1577-1584; Lewis W, Levine E S, Griniuviene B, Tankersley K O, Colacino J M, Sommadossi J P, Watanabe K A, Perrino F W. Fialuridine and its metabolites inhibit DNA polymerase gamma at sites of multiple adjacent analog incorporation, decrease mtDNA abundance, and cause mitochondrial structural defects in cultured hepatoblasts. Proc Natl Acad Sci USA. 1996; 93: 3592-7; Pan-Zhou X R, L Cui, X J Zhou, J P Sommadossi, V M Darley-Usmar. Differential effects of antiretroviral nucleoside analogs on mitochondrial function in HepG2 cells. *Antimicrob. Agents Chemother.* 2000, 44, 496-503). For example, electron micrographs of HepG2 cells incubated with 10 μM fialuridine (FIAU; 1,2'-deoxy-2'-fluoro-1-D-arabinofuranosly-5-iodo-uracil) showed the presence of enlarged mitochondria with morphological changes consistent with mitochondrial dysfunction. To determine if the JAK inhibitor compounds promote morphological changes in mitochondria, HepG2 cells ($2.5 \times 10^4$ cells/mL) can be seeded into tissue cultures dishes (35 by 10 mm) in the presence of 0 μM, 0.1 μM, 1 μM, 10 μM and 100 M nucleoside analog. At day 8, the cells can be fixed, dehydrated, and embedded in Eponas described previously. Thin sections can be prepared, stained with uranyl acetate and lead citrate, and then examined using transmission electron microscopy.

Example 4: Mitochondrial Toxicity Assays in Neuro2A Cells

To estimate the potential of the TREM-1 inhibitor compounds to cause neuronal toxicity, mouse Neuro2A cells (American Type Culture Collection 131) can be used as a model system (see Ray A S, Hernandez-Santiago B I, Mathew J S, Murakami E, Bozeman C, Xie M Y, Dutschman G E, Gullen E, Yang Z, Hurwitz S, Cheng Y C, Chu C K, McClure H, Schinazi R F, Anderson K S. Mechanism of anti-human immunodeficiency virus activity of beta-D-6-cyclopropylamino-2',3'-didehydro-2',3'-dideoxyguanosine. *Antimnicrob. Agents Chemother.* 2005, 49, 1994-2001). The concentrations necessary to inhibit cell growth by 50% ($CC_{50}$) can be measured using the 3-(4,5-dimethyl-thiazol-2-yl)-2,5-diphenyltetrazolium bromide dye-based assay, as described. Perturbations in cellular lactic acid and mitochondrial DNA levels at defined concentrations of drug can be carried out as described above.

Example 5: Assay for Bone Marrow Cytotoxicity

Primary human bone marrow mononuclear cells can be obtained commercially from Cambrex Bioscience (Walkersville, MD). CFU-GM assays can be carried out using a bilayer soft agar in the presence of 50 units/mL human recombinant granulocyte/macrophage colony-stimulating factor, while BFU-E assays used a methylcellulose matrix containing 1 unit/mL erythropoietin (see Sommadossi J-P, Carlisle R. Toxicity of 3'-azido-3'-deoxythymidine and 9-(1, 3-dihydroxy-2-propoxymethyl) guanine for normal human hepatopoietic progenitor cells in vitro. Antimicrob. Agents Chemother. 1987; 31: 452-454; Sommadossi, J P, Schinazi, R F, Chu, C K, and Xie, M Y. Comparison of Cytotoxicity of the (−) and (+) enantiomer of 2',3'-dideoxy-3'-thiacytidine in normal human bone marrow progenitor cells. Biochem. Pharmacol. 1992; 44:1921-1925). Each experiment can be performed in duplicate in cells from three different donors. AZT can be used as a positive control. Cells can be incubated in the presence of a TREM-1 inhibitor compound for 14-18 days at 37° C. with 5% $CO_2$, and colonies of greater than 50 cells can be counted using an inverted microscope to determine $IC_{50}$. The 50% inhibitory concentration ($IC_{50}$) can be obtained by least-squares linear regression analysis of the logarithm of drug concentration versus BFU-E survival fractions. Statistical analysis can be performed with Student's t test for independent non-paired samples.

Example 6: Cytotoxicity Assay

The toxicity of the compounds can be assessed in Vero, human PBM, CEM (human lymphoblastoid), MT-2, and HepG2 cells, as described previously (see Schinazi R. F., Sommadossi J.-P., Saalmann V., Cannon D. L., Xie M.-Y., Hart G. C., Smith G. A. & Hahn E. F. *Antimicrob. Agents Chemother.* 1990, 34, 1061-67). Cycloheximide can be included as positive cytotoxic control, and untreated cells exposed to solvent can be included as negative controls. The cytotoxicity $IC_{50}$ can be obtained from the concentration-response curve using the median effective method described previously (see Chou T.-C. & Talalay P. *Adv. Enzyme Regul.* 1984, 22, 27-55; Belen'kii M. S. & Schinazi R. F. Antiviral Res. 1994, 25, 1-11).

Example 7: Bioavailability Assay in Cynomolgus Monkeys

The following procedure can be used to determine whether the compounds are bioavailable. Within 1 week prior to the study initiation, a cynomolgus monkey can be surgically implanted with a chronic venous catheter and subcutaneous venous access port (VAP) to facilitate blood collection and can undergo a physical examination including hematology and serum chemistry evaluations and the body weight recording. Each monkey (six total) receives approximately 250 μCi of $^3H$ activity with each dose of active compound at a dose level of 10 mg/kg at a dose concentration of 5 mg/mL, either via an intravenous bolus (3 monkeys, IV), or via oral gavage (3 monkeys, PO). Each dosing syringe is weighed before dosing to gravimetrically determine the quantity of formulation administered. Urine samples are collected via pan catch at the designated intervals (approximately 18-0 hours pre-dose, 0-4, 4-8 and 8-12 hours post-dosage) and processed. Blood samples are collected as well (pre-dose, 0.25, 0.5, 1, 2, 3, 6, 8, 12 and 24 hours post-dosage) via the chronic venous catheter and VAP or from a peripheral vessel if the chronic venous catheter procedure should not be possible. The blood and urine samples are analyzed for the maximum concentration (Cmax), time when the maximum concentration is achieved (TmaX), area under the curve (AUC), half life of the dosage concentration (TV,), clearance (CL), steady state volume and distribution (Vss) and bioavailability (F).

Example 8: Cell Protection Assay (CPA)

The assay can be performed essentially as described by Baginski, S. G.; Pevear, D. C.; Seipel, M.; Sun, S. C. C.; Benetatos, C. A.; Chunduru, S. K.; Rice, C. M. and M. S. Collett "Mechanism of action of a pestivirus antiviral compound" PNAS USA 2000, 97 (14), 7981-7986. MDBK cells (ATCC) are seeded onto 96-well culture plates (4,000 cells per well) 24 hours before use. After infection with BVDV (strain NADL, ATCC) at a multiplicity of infection (MOI) of 0.02 plaque forming units (PFU) per cell, serial dilutions of test compounds are added to both infected and uninfected cells in a final concentration of 0.5% DMSO in growth medium. Each dilution is tested in quadruplicate.

Cell densities and virus inocula are adjusted to ensure continuous cell growth throughout the experiment and to achieve more than 90% virus-induced cell destruction in the untreated controls after four days post-infection. After four days, plates are fixed with 50% TCA and stained with sulforhodamine B. The optical density of the wells is read in a microplate reader at 550 nm.

The 50% effective concentration ($EC_{50}$) values are defined as the compound concentration that achieved 50% reduction of cytopathic effect of the virus.

Example 9: Plaque Reduction Assay

For a compound, the effective concentration is determined in duplicate 24-well plates by plaque reduction assays. Cell monolayers are infected with 100 PFU/well of virus. Then, serial dilutions of test compounds in MEM supplemented with 2% inactivated serum and 0.75% of methyl cellulose are added to the monolayers. Cultures are further incubated at 37° C. for 3 days, then fixed with 50% ethanol and 0.8% Crystal Violet, washed and air-dried. Then plaques are counted to determine the concentration to obtain 90% virus suppression.

Example 10: Yield Reduction Assay

For a compound, the concentration to obtain a 6-log reduction in viral load is determined in duplicate 24-well plates by yield reduction assays. The assay is performed as described by Baginski, S. G.; Pevear, D. C.; Seipel, M.; Sun, S. C. C.; Benetatos, C. A.; Chunduru, S. K.; Rice, C. M. and M. S. Collett "Mechanism of action of a pestivirus antiviral compound" PNAS USA 2000, 97 (14), 7981-7986, with minor modifications.

Briefly, MDBK cells are seeded onto 24-well plates ($2 \times 10^5$ cells per well) 24 hours before infection with BVDV (NADL strain) at a multiplicity of infection (MOI) of 0.1 PFU per cell. Serial dilutions of test compounds are added to cells in a final concentration of 0.5% DMSO in growth medium. Each dilution is tested in triplicate. After three days, cell cultures (cell monolayers and supernatants) are lysed by three freeze-thaw cycles, and virus yield is quantified by plaque assay. Briefly, MDBK cells are seeded onto 6-well plates ($5 \times 10^5$ cells per well) 24 h before use. Cells are inoculated with 0.2 mL of test lysates for 1 hour, washed and overlaid with 0.5% agarose in growth medium. After 3 days, cell monolayers are fixed with 3.5% formaldehyde and stained with 1% crystal violet (w/v in 50% ethanol) to visualize plaques. The plaques are counted to determine the concentration to obtain a 6-log reduction in viral load.

Example 11: Assay for Effectiveness Against Dengue

One representative high throughput assay for identifying compounds useful for treating Dengue is described in Lim et al., A scintillation proximity assay for dengue virus NS5 2'-O-methyltransferase kinetic and inhibition analyses, Antiviral Research, Volume 80, Issue 3, December 2008, Pages 360-369.

Dengue virus (DENV) NS5 possesses methyltransferase (MTase) activity at its N-terminal amino acid sequence and is responsible for formation of a type 1 cap structure, m7GpppAm2'-O in the viral genomic RNA. Optimal in vitro conditions for DENV2 2'-O-MTase activity can be characterized using purified recombinant protein and a short biotinylated GTP-capped RNA template. Steady-state kinetics parameters derived from initial velocities can be used to establish a robust scintillation proximity assay for compound testing. Pre-incubation studies by Lim et al., Antiviral Research, Volume 80, Issue 3, December 2008, Pages 360-369, showed that MTase-AdoMet and MTase-RNA complexes were equally catalytically competent and the enzyme supports a random bi bi kinetic mechanism. Lim validated the assay with competitive inhibitory agents, S-adenosylhomocysteine and two homologues, sinefungin and dehydrosinefungin. A GTP-binding pocket present at the N-terminal of DENV2 MTase was previously postulated to be the cap-binding site. This assay allows rapid and highly sensitive detection of 2'-O-MTase activity and can be readily adapted for high-throughput screening for inhibitory compounds. It is suitable for determination of enzymatic activities of a wide variety of RNA capping MTases.

Example 12: Evaluation of Antiviral Activity Against Chikungunya

One representative assay for identifying therapies useful for treating the Chikungunya virus is described in Couderc T, et al, PLoS Pathogens, A Mouse Model for Chikungunya: Young Age and Inefficient Type-I Interferon Signaling Are Risk Factors for Severe Disease, 2008 Feb. 8; 4(2):e29. In this assay, the effect of TREM-1 inhibitors, alone or in combination, can be assessed. Live, replication competent Chikungunya virus is used to confer systemic infection in the murine model, wherein infection is in monocytes, macrophages and other permissive cell types. In the presence of TREM-1 inhibitors, alone or in combination, and their impact on Chikungunya virus-driven inflammation, activation, conference of rheumatoid arthritis and other systemic effects, can be quantified. Cellular events such as Chikungunya virus-induced monocyte/macrophage activation, systemic inflammation including IL-6, TNF-α, IL-1α/β, or other cytokine levels, can be quantified.

Another assay which can be used to measure the effect of TREM-1 inhibitors on Chikungunya infection, alone or in combination, is a primary human or murine macrophages, also described by the above reference above. Human or murine macrophages can be infected in vitro or ex vivo and measures of secreted inflammatory cytokines such as IL-6, TNF-α, IL-1α/ρ, or GM-CSF can be quantified in supernatants as can down-regulation of TREM-1 inhibitor-induced activation markers such as sCD163, HLA-DR, CD163, or IL-6R.

There are now many replicon systems available for Dengue and Chikungunya in the literature. Examples include those disclosed in PCT WO2008030220 and Gläsker et al., "Virus replicon particle based Chikungunya virus neutralization assay using *Gaussia* luciferase as readout," Virology Journal 2013, 10:235. Gläsker discloses that Chikungunya virus (CHIKV) has been responsible for large epidemic outbreaks causing fever, headache, rash and severe arthralgia. As nucleic acid amplification can only be used during the viremic phase of the disease, serological tests like neutralization assays are necessary for CHIKV diagnosis and for determination of the immune status of a patient. Furthermore, neutralization assays represent a useful tool to validate the efficacy of potential vaccines. As CHIKV is a BSL3 agent, neutralization assays with infectious virus need to be performed under BSL3 conditions. The following is a neutralization assay based on non-infectious virus replicon particles (VRPs).

Methods:
VRPs can be produced by co-transfecting baby hamster kidney-21 cells with a CHIKV replicon expressing *Gaussia* luciferase (Gluc) and two helper RNAs expressing the CHIKV capsid protein or the remaining structural proteins, respectively. The resulting single round infectious particles can be used in CHIKV neutralization assays using secreted Glue as readout.

Results:
Upon co-transfection of a CHIKV replicon expressing Gluc and the helper RNAs, VRPs can be produced efficiently under optimized conditions at 32° C. Infection with VRPs can be measured via Gluc secreted into the supernatant. The successful use of VRPs in CHIKV neutralization assays can be demonstrated using a CHIKV neutralizing monoclonal antibody or sera from CHIKV infected patients. In the 96-well format, a high multiplicity of infection is favored, while in the 24-well format reliable results are also obtained using lower infection rates.

Evaluation of the neutralization assay is already possible at the same day of infection.

Conclusions:
The VRP based CHIKV neutralization assay using Gluc as readout represents a fast and useful method to determine CHIKV neutralizing antibodies without the need of using infectious CHIKV.

Example 13: Extrapolation of the Data from Example 2 Relative to a Cure for HIV, as Well as Other Viruses The data shown in FIGS. 5A-B and 6A-D demonstrate that blockade of TREM-1 at the receptor level results in potent inhibition of viral replication and virally-induced activation. These data demonstrate that TREM-1 inhibition represents a novel, potent mechanism to inhibit viral replication in cells expressing TREM-1. Inhibition of viral replication with the TREM-1 inhibitor represents a proof of principle wherein inhibition of this receptor down-regulates the cellular activation that is critical to allow for the virus to replicate in these cells. This mechanism, which has been reduced to practice with HIV, is also applicable to other viruses that infected cells expressing TREM-1, or interact with cells expressing TREM-1, including but not limited to Chikungunya, West Nile, Dengue, Influenza, and other viruses. These data also demonstrate that virus-induced activation allows for the virus to replicate in TREM-1 expressing cells, and that inhibition of virus-induced activation prevents the virus from replicating. This application also applies to other viruses that rely on cellular activation to replicate in host cells, including but not limited to Chikungunya, West Nile, Dengue, Influenza, and other viruses.

To demonstrate this, primary human macrophages were infected with an M-R5 replication competent HIV-1 (BaL) in the presence of various concentrations of AZT (control) or TREM-1 peptide. Extracellular virus was quantified 7 days after infection (HIV-1 p24 ELISA). The TREM-1 peptide demonstrates nanomolar inhibition of HIV-1 replication in primary human macrophages. As expected, AZT control demonstrated nanomolar inhibition of viral replication. The TREM-1 peptide did not demonstrate any apparent toxicity (quantified by zombie violet live/dead dye, Violet channel, FACS). The TREM-1 peptide did not demonstrate antiviral potency up to 50 μM in primary human peripheral blood mononuclear (PBM) cells (data not shown). The data is shown below in Table 2.

TABLE 2

Antiviral potency of the TREM-1 peptide in primary human macrophages.

| Drug | Class | Antiviral potency in primary human macrophages ($EC_{50}$, μM) | Antiviral potency in primary human macrophages ($EC_{90}$, μM) | Toxicity in primary human macrophages ($IC_{50}$, μM) | Therapeutic index |
|---|---|---|---|---|---|
| TREM-1 peptide | TREM-1 inhibitor | 0.14<br>≤0.01 (43.1)<br><0.01 (73.6)<br>0.15<br>0.10 | 3.4<br>7.6<br>6.4 | >100<br>>100 | >100 |
| AZT | Nucleoside analog | 0.01 ± 0.02 | 0.7 ± 0.2 | >100 | >100 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents. All references cited herein are incorporated by reference in their entirety for all purposes.

The invention claimed is:

1. A method for treating an AIDS-related neurological disorder, comprising administering to a patient in need thereof an effective antiviral amount of a TREM-1 inhibitor.

2. The method of claim 1, wherein the TREM-1 inhibitor is selected from the group consisting of TLT-1, -CDR2 (SAVDRRAPAGRR, SEQ ID NO 1), TLT-1-CDR3 (CMVDGARGPQILHR, SEQ ID NO 2), LR17 (LQEED-AGEYGCMVDGAR, SEQ ID NO 3), LR6-1 (LQEEDA, SEQ ID NO 4), LR6-2 (EDAGEY, SEQ ID NO 5), LR6-3 (GEYGCM, SEQ ID NO 6), LR12 (LQEEDAGEYGCM, SEQ ID NO 7), prodrugs thereof, conjugated versions thereof, deuterated variations thereof, analogs thereof comprising non-naturally occurring amino-acids, functional variations thereof including a different sequence of amino acids but which retain TREM-1 inhibitory activity, analogs thereof in which each amino acid can be, individually, a D or L isomer, and combinations of L-isoforms with D-isoforms thereof, wherein the peptides can optionally be stabilized by micelles.

3. The method of claim 1, wherein the TREM-1 inhibitor is selected from the group consisting of MicroRNA 294, human cathelicidin LL-37, the F-c portion of human IgG (AdTREM-1Ig), antibodies directed to the TREM-1 and/or sTREM-1 or TREM-1 and/or sTREM-1 ligands, and fragments thereof which also inhibit TREM-1, small molecules inhibiting the function, activity or expression of TREM-1, siRNAs directed to TREM-1, shRNAs directed to TREM-1, antisense oligonucleotides directed to TREM-1, ribozymes directed to TREM-1, aptamers which bind to and inhibit TREM-1, fusion proteins between human IgG1 constant region and the extracellular domain of mouse TREM-1 or that of human TREM-1.

4. The method of claim 1, wherein the TREM-1 inhibitor is administered in combination or alternation with a JAK inhibitor.

5. The method of claim 4, wherein the JAK inhibitor is selected from the group consisting of CEP-701 (Lestaurtinib), AZD1480, LY3009104/INCB28050 Pacritinib/SB1518, VX-509, GLPG0634, INC424, R-348, CYT387, TG 10138, AEG 3482, 7-iodo-N-(4-morpholinophenyl)thieno[3,2-d]pyrimidin-2-amine, 7-(4-aminophenyl)-N-(4-morpholinophenyl)thieno[3,2-d]pyrimidin-2-amine, N-(4-(2-(4-morpholinophenylamino)thieno [3,2-d]pyrimidin-7-yl)phenyl)acrylamide, 7-.beta.-aminophenyl)-N-(4-morpholinophenyl)thieno [3,2-d]pyrimidin-2amine, N-(3-(2-(4-morpholinophenylamino)thieno[3,2-d]pyrimidin-7-yl)phenyl)acrylamide, N-(4-morpholinophenyl)thieno [3,2-d]pyrimidin-2-amine, methyl 2-(4-morpholinophenylamino)thieno [3,2-d]pyrimidine-7-carboxylate, N-(4-morpholinophenyl)-5H-pyrrolo[3,2-d]pyrimidin-2-amine, morpholinophenyl)thieno[3,2-d]pyrimidin-2-amine, 7-(4-amino-3-methoxyphenyl)-N-(4-4-(2-(4-morpholinophenylamino)thieno[3,2-d]pyrimidin-7-yl)benzene-sulfonamide, N,N-dimethyl-3-(2-(4-morpholinophenylamino)thieno[3,2-d]pyrimidin-7-yl)benzenesulfonamide, 1-ethyl-3-(2-methoxy-4-(2-(4-morpholinophenylamino)thieno[3,2-d] pyrimidin-7-yl)phenyl)urea, N-(4-(2-(4-morpholinophenylamino)thieno [3,2-d]pyrimidin-7-yl)phenyl)methanesulfonamide, 2-methoxy-4-(2-(4-morpholinophenylamino)thieno[3,2-d]pyrimidin-7-yl)phenol, 2-cyano-N-(3-(2-(4-morpholinophenylamino)thieno[3,2-d]pyrimidin-7-yl-)phenyl) acetamide, N-(cyanomethyl)-2-(4-morpholinophenylamino)thieno[3,2-d]pyrimidine-7-carboxamide, N-(3-(2-(4-morpholinophenylamino)thieno[3,2-d]pyrimidin-7-yl)phenyl)methanesulfonamide, 1-ethyl-3-(4-(2-(4-morpholinophenylamino)thieno[3,2-d]pyrimidin-7-yl)-2-(trifluoromethoxy)phenyl)urea, N-(3-nitrophenyl)-7-phenylthieno[3,2-d]pyrimidin-2-amine, 7-iodo-N-(3-nitrophenyl)thieno [3,2-d]pyrimidin-2-amine, N1-(7-(2-ethylphenyl)thieno[3,2-d]pyrimidin-2-yl)benzene-1,3-diamine, N-tert-butyl-3-(2-(4-morpholinophenylamino)thieno[3,2-d]pyrimidin-7-yl)benzenesulfonamide, N1-(7-iodothieno [3,2-d]pyrimidin-2-yl)benzene-1,3-diamine, 7-(4-amino-3-(trifluoromethoxy)phenyl)-N-(4-morpholinophenyl)thieno [3,2-d]pyrimidin-2-amine, 7-(2-ethylphenyl)-N-(4-morpholinophenyl)thieno [3,2-d]pyrimidin-2-amine, N-(3-(2-(4-morpholinophenylamino)thieno [3,2-d]pyrimidin-7-yl)phenyl) acetamide, N-(cyanomethyl)-N-(3-(2-(4-morpholinophenylamino)thieno[3,2-d]pyrimidin-7-yl)phenyl)methanesulfonamide, N-(cyanomethyl)-N-(4-(2-(4-morpholinophenylamino)thieno[3,2-d]pyrimidin-7-yl)phenyl)methanesulfonamide, N-(3-(5-methyl-2-(4-morpholinophenylamino)-5H-pyrrolo[3,2-d]pyrimidin-7-yl)phenyl)methanesulfonamide, 4-(5-methyl-2-(4-morpholinophenylamino)-5H-pyrrolo[3,2-d]pyrimidin-7-yl)benzenesulfonamide, N-(4-(5-methyl-2-(4-morpholinophenylamino)-5H-pyrrolo[3,2-d]pyrimidin-7-yl)phenyl)methanesulfonamide, 7-iodo-N-(4-morpholinophenyl)-5H-pyrrolo [3,2-d]pyrimidin-2-amine, 7-(2-isopropylphenyl)-N-(4-morpholinophenyl)thieno [3,2-d]pyrimidin-2-amine, 7-bromo-N-(4-morpholinophenyl)thieno[3,2-d]pyrimidin-2-amine, N7-(2-isopropylphenyl)-N2-(4-morpholinophenyl)thieno[3,2-d]pyrimidine-2,7-diamine, N7-(4-isopropylphenyl)-N2-(4-morpholinophenyl)thieno[3,2-d]pyrimidine-2,7-diamine, 7-(5-amino-2-methylphenyl)-N-(4-morpholinophenyl)thieno[3,2-d]pyrimidin-2-amine, N-(cyanomethyl)-4-(2-(4-morpholinophenylamino)thieno [3,2-d]pyrimidin-7-yl)benzamide, 7-iodo-N-(3-morpholinophenyl)thieno[3,2-d]pyrimidin-2-amine, 7-(4-amino-3-nitrophenyl)-N-(4-morpholinophenyl)thieno [3,2-d]pyrimidin-2-amine, 7-(2-methoxypyridin-3-yl)-N-(4-morpholinophenyl)thieno [3,2-d]pyrimidin-2-amine, (3-(7-iodothieno[3,2-d]pyrimidin-2-yl amino)phenyl)methanol, N-tert-butyl-3-(2-(3-morpholinophenyl amino)thieno[3,2-d]pyrimidin-7-yl)benzenesulfonamide, N-tert-butyl-3-(2-(3-(hydroxymethyl)phenylamino)thieno [3,2-d]pyrimidin-7-yl)-benzenesulfonamide, N-(4-morpholinophenyl)-7-(4-nitrophenylthio)-5H-pyrrolo[3,2-d]pyrimidin-2-amine, N-tert-butyl-3-(2-(3,4,5-trimethoxy phenyl amino)thieno[3,2-d]pyrimidin-7-yl)benzenesulfonamide, 7-(4-amino-3-nitrophenyl)-N-(3,4-dimethoxy phenyl)thieno[3,2-d]pyrimidin-2-amine, N-(3,4-dimethoxyphenyl)-7-(2-methoxypyridin-3-yl)thieno[3,2-d]pyrimidin-2-amine, N-tert-butyl-3-(2-(3,4-dimethoxy phenylamino)thieno[3,2-d]pyrimidin-7-yl)benzenesulfonamide, 7-(2-aminopyrimidin-5-yl)-N-(3,4-dimethoxyphenyl)thieno [3,2-d]pyrimidin-2-amine, N-(3,4-dimethoxyphenyl)-7-(2,6-dimethoxypyridin-3-yl)thieno [3,2-d]-pyrimidin-2-amine, N-(3,4-dimethoxyphenyl)-7-(2,4-dimethoxypyrimidin-5-yl)thieno [3,2-d]pyrimidin-2-amine, 7-iodo-N-(4-(morpholinomethyl)phenyl)thieno[3,2-d]pyrimidin-2-amine, N-tert-butyl-3-(244-(morpholinomethyl)phenyl amino)thieno [3,2-d]pyrimidin-7-yl)benzenesulfonamide, 2-cyano-N-(4-methyl-3-(2-(4-morpholinophenylamino)thieno [3,2-d]pyrimidin-7-yl)phenyl)acetamide, ethyl 3-(2-(4-morpholinophenylamino) thieno [3,2-d]pyrimidin-7-yl)benzoate, 7-bromo-N-(4-(2-(pyrrolidin-1-yl)ethoxy)phenyl)thieno[3,2-d]pyrimidin-2-amine, N-(3-(2-(4-(2-(pyrrolidin-1-yl)ethoxy)phenylamino)thieno[3,2-d]pyrimidin-7-yl)phenyl)acetamide, N-(cyanomethyl)-3-(2-(4-morpholinophenylamino)thieno[3,2-d]pyrimidin-7-yl)benzamide, N-tert-butyl-3-(2-(4-morpholinophenylamino)thieno[3,2-d]pyrimidin-7-yl)benzamide, N-tert-butyl-3-(2-(4-(1-ethylpiperidin-4-yloxy)phenylamino)thieno-[3,2-d]pyrimidin-7-yl)benzenesulfonamide, tert-butyl-4-(2-(4-(morpholinomethyl)phenyl amino)thieno [3,2-d]pyrimidin-7-yl)-1H-pyrazole-1-carboxylate, 7-bromo-N-(4-((4-ethylpiperazin-1-yl)methyl)phenyl)thieno[3,2-d]pyrimidin-2-amine, N-tert-butyl-3-(2-(4-((4-ethylpiperazin-1-yl)methyl)phenylamino)-thieno[3,2-d]pyrimidin-7-yl)benzenesulfonamide, N-(4-((4-ethylpiperazin-1-yl)methyl)phenyl)-7-(1H-pyrazol-4-yl)thieno[3,2-d]pyrimidin-2-amine, N-(cyanomethyl)-3-(2-(4-(morpholinomethyl)phenylamino)thieno[3,2-d]pyrimidin-7-yl)benzamide, N-tert-butyl-3-(2-(4-(2-(pyrrolidin-1-yl) ethoxy)phenylamino)thieno[3,2-d]-pyrimidin-7-yl)benzenesulfonamide, tert-butyl pyrrolidin-1-yl)ethoxy)phenylamino)thieno[3,2-d]pyrimidin-7-yl)benzylcarbamate, 3-(2-(4-(2-(pyrrolidin-1-yl) ethoxy)phenylamino)thieno[3,2-d]pyrimidin-7-yl)benzenesulfonamide, 7-(3-chloro-4-fluorophenyl)-N-(4-(2-(pyrrolidin-1-yl)ethoxy)phenyl)thieno-[3,2-d]pyrimidin-2-amine, tert-butyl 4-(2-(4-(1-ethylpiperidin-4-yloxy)phenylamino)thieno[3,2-d]pyrimidin-7-yl-)-1H-pyrazole-1-carboxylate, 7-(benzo[d][1,3]dioxol-5-yl)-N-(4-(morpholinomethyl)phenyl)thieno [3,2-d]pyrimidin-2-amine, tert-butyl 5-(2-(4-(morpholinomethyl)phenylamino)thieno[3,2-d]pyrimidin-7-yl)-1H-indole-1-carboxylate, 7-(2-aminopyrimidin-5-yl)-N-(4-(morpholinomethyl)phenyl)thieno[3,2-d]pyrimidin-2-amine, tert-butyl 4-(2-(4-(morpholinomethyl)phenylamino)thieno[3,2-d]pyrimidin-7-yl)-5,6-dihydropyridine-1 (2H)-carboxylate, tert-butyl morpholinomethyl)phenylamino)thieno[3,2-d]pyrimidin-7-yl)benzylcarbamate, N-(3-(2-(4-(morpholinomethyl)phenylamino)thieno[3,2-d]pyrimidin-7-yl)-phenyl) acetamide, N-(4-(2-(4-(morpholinomethyl)phenylamino)thieno[3,2-d]pyrimidin-7-yl)phenyl) acetamide, N-(3-(2-(4-(morpholinomethyl)phenylamino)thieno[3,2-d]pyrimidin-7-yl)phenyl)methanesulfonamide, 7-(4-(4-methylpiperazin-1-yl)phenyl)-N-(4-(morpholinomethyl)phenyl)thieno-[3,2-d]pyrimidin-2-amine, N-(2- methoxy-4-(2-(4-(morpholinomethyl)phenylamino)thieno[3,2-d]pyrimidin-7-yl)phenyl) acetamide, 7-bromo-N-(3,4,5-trimethoxy phenyl)thieno[3,2-d]pyrimidin-2-amine, (3-(2-(3,4,5-trimethoxyphenylamino)thieno[3,2-d]pyrimidin-7-yl)phenyl)methanol, (4-(2-(3,4,5-trimethoxyphenylamino)thieno[3,2-d]pyrimidin-7-yl)phenyl)methanol, (3-(2-(4-morpholinophenylamino)thieno[3,2-d]pyrimidin-7-yl)phenyl)methanol, (4-(2-(4-morpholinophenylamino)thieno[3,2-d]pyrimidin-7-yl)phenyl)methanol, N-(pyrrolidin-1-yl) ethoxy)phenylamino)thieno[3,2-d]pyrimidin-7-yl)benzyl)methanesulfonamide, tert-butyl morpholinomethyl)phenylamino)thieno[3,2-d]pyrimidin-7-yl)benzylcarbamate, N-(4-(morpholinomethyl)phenyl)-7-(3-(piperazin-1-yl)phenyl)thieno[3,2-d]pyrimidin-2-amine, 7-(6-(2-morpholinoethylamino)pyridin-3-yl)-N-(3,4,5-trimethoxy phenyl)thieno[3,2-d]pyrimidin-2-amine, 7-(2-ethylphenyl)-N-(4-(2-(pyrrolidin-1-yl)ethoxy)phenyl)thieno[3,2-d]pyrimidin-2-amine, 7-(4-(aminomethyl)phenyl)-N-(4-(morpholinomethyl)phenyl)thieno[3,2-d]pyrimidin-2-amine, N-(4-(1-ethylpiperidin-4-yloxy)phenyl)-7-(1H-pyrazol-4-yl) thieno[3,2-d]pyrimidin-2-amine, N-(2,4-dimethoxyphenyl)-7-phenylthieno[3,2-d]pyrimidin-2-amine, 7-bromo-N-(3,4-dimethoxyphenyl)thieno[3,2-d]pyrimidin-2-amine, N-(3,4-dimethoxyphenyl)-7-phenylthieno[3,2-d]pyrimidin-2-amine, and pharmaceutically acceptable salts and prodrugs thereof.

6. The method of claim 1, further comprising the co-administration of a) at least one each of an adenine, cytosine, thymidine, and guanine nucleoside antiviral agent, or b) at least one additional antiviral agent selected from the group consisting of non-nucleoside reverse transcriptase inhibitors (NNRTI), protease inhibitors, fusion inhibitors, entry inhibitors, attachment inhibitors, and integrase inhibitors.

7. The method of claim 6, wherein the nucleoside antiretroviral agents comprise two or more of: a) (−)-FTC or 3TC, b) TDF or TAF, c) ABC or EFdA, and d) a NNRTI, a protease inhibitor (PI), or an integrase inhibitor (IN), e) a fusion inhibitor with two nucleosides or and PI or IN.

8. The method of claim 7, wherein the NNRTI is Sustiva, the protease inhibitor is Kaletra, or the integrase inhibitor is Raltegravir or Elvitegravir.

9. The method of claim 6, wherein the TREM-1 inhibitor, and the at least one each of an adenine, cytosine, thymidine, and guanine nucleoside antiviral agent, or at least one additional antiviral agent selected from the group consisting of non-nucleoside reverse transcriptase inhibitors (NNRTI), protease inhibitors, fusion inhibitors, entry inhibitors, attachment inhibitors, and integrase inhibitors, are administered in combination.

10. The method of claim 6, wherein the TREM-1 inhibitor, and the at least one each of an adenine, cytosine, thymidine, and guanine nucleoside antiviral agent, or at least one additional antiviral agent selected from the group consisting of non-nucleoside reverse transcriptase inhibitors (NNRTI), protease inhibitors, fusion inhibitors, entry inhibitors, attachment inhibitors, and integrase inhibitors, are administered in alternation.

11. The method of claim 3, wherein the JAK inhibitor is

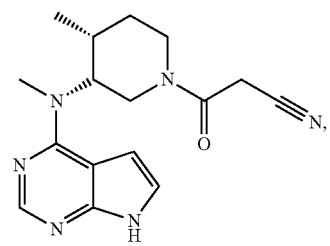

or a pharmaceutically acceptable salt or prodrug thereof.

12. The method of claim 3, wherein the JAK Inhibitor is

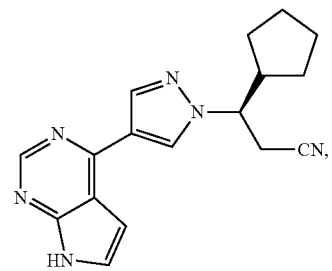 [SMILES: N#CC[C@H](C1CCCC1)n1cc(-c2ncnc3[nH]ccc23)cn1]

or a pharmaceutically acceptable salt or prodrug thereof.

13. The method of claim 1, further comprising the co-administration of a macrophage depleting agent.

14. The method of claim 1, further comprising administration of HAART along with the TREM-1 inhibitor.

15. A method for treating AIDS-related complex (ARC), persistent generalized lymphadenopathy (PGL), anti-HIV antibody positive and HIV-positive conditions, Kaposi's sarcoma, thrombocytopenia purpurea and HIV-related opportunistic infections, comprising administering to a patient in need thereof an effective amount of a TREM-1 inhibitor.

16. A method for preventing or retarding the progression of clinical illness in individuals who are anti-HIV antibody or HIV-antigen positive or who have been exposed to HIV, comprising administering to a patient in need thereof an effective amount of a TREM-1 inhibitor.

* * * * *